(12) United States Patent
Desgroseillers et al.

(10) Patent No.: US 6,987,003 B1
(45) Date of Patent: Jan. 17, 2006

(54) MAMMALIAN STAUFFEN AND USE THEREOF

(75) Inventors: Luc Desgroseillers, St-Basile Le Grand (CA); Andrew J. Mouland, Montreal (CA); Eric A. Cohen, Montreal (CA); Louise Wickham, Montreal (CA); Ming Luo, Montreal (CA); Thomas Duchaîne, Montreal (CA)

(73) Assignee: Université de Montréal, Montreal (CA)

( * ) Notice: Subject to any disclaimer, the term of this patent is extended or adjusted under 35 U.S.C. 154(b) by 0 days.

(21) Appl. No.: 09/316,048

(22) Filed: May 21, 1999

(30) Foreign Application Priority Data

May 22, 1998 (CA) .................................. 2238656

(51) Int. Cl.
  C12P 21/06 (2006.01)
  C07H 21/02 (2006.01)
  C12N 15/00 (2006.01)
  C12N 5/00 (2006.01)

(52) U.S. Cl. .................. 435/69.1; 536/23.1; 435/320.1; 435/325

(58) Field of Classification Search ................ 536/23.1, 536/23.5; 435/320.1, 325, 69.1, 320
  See application file for complete search history.

(56) References Cited

OTHER PUBLICATIONS

Rudinger; Characteristics of the amino as components of a peptide hormone sequence, 1976, Peptide Hormones; 1-7.*
Johnston et al.; Accession No. M69111.1, 1993.*
Marra et al.; Accession No. AA122533, 1997.*
Banfi et al.; Accession No. G30939, 1998.*
Ainger et al. 1993, J. Cell. Biol. 123:431-441.
Aloyz et al. 1995, Peptides 16:331-338.
Arya et al. 1985, Science 229:69-73.
Bassell et al. 1997, Curr. Opin. Cell Biol. 9:109-115.
Benkirane et al. 1997, EBMO J. 16:611-624.
Bergeron et al. 1991, J. Virol. 65:7-15.
Berkowitz et al. 1995, Virology 212:718-723.
Berlioz et al. 1995, J. Virol. 69:2214-2222.
Bertrand et al. 1998, Mol. Cell 2:437-445.
Breitwieser et al. 1996, Genes & Dev. 10:2179-2188.

(Continued)

*Primary Examiner*—Ram R. Shukla
*Assistant Examiner*—Joanne Hama
(74) *Attorney, Agent, or Firm*—Goudreau Gage Dubuc

(57) ABSTRACT

The present invention relates to mammalian staufen, a double-stranded RNA-binding protein involved in mRNA transport and localization. The invention further relates to the demonstration of the association of a RNA-binding protein with the rough endoplasmic reticulum (RER), implicating staufen and related proteins in the transport of RNA to its site of translation. Broadly, the invention therefore relates to transport and translation of RNA. More specifically, the present invention relates to human and mouse staufen proteins and to the modulation of transport of RNA to the RER by these proteins. The present invention also relates to isolated nucleic acid molecules encoding mammalian staufen, as well as vectors and host cells harboring same. In addition, the present invention relates to screening assays for identifying modulators of staufen activity and to the identification of mutants thereof which abrogate their interaction with RER. Furthermore, the present invention relates to the use of the double-stranded RNA binding activity of staufen as a means to target proteins into virions. The invention in addition relates to the incorporation of staufen into RNA viruses and the use of overexpression of staufen to significantly decrease the infectivity thereof. More particularly, the present invention relates to a novel and broad class of molecules which can be used as carriers to target molecules into virions of RNA viruses and to decrease infectivity of a wide variety of RNA viruses including retroviruses.

10 Claims, 17 Drawing Sheets

OTHER PUBLICATIONS

Broadus et al. 1998, Nature 391:792-795.
Circle et al. 1997, RNA 3:438-448.
Cogniaux et al. 1990, J. Immunol. Meth. 128:165-175.
Cosentino et al. 1995, Proc. Natl. Acad. Sci USA 92:9445-9449.
Crino et al. 1996, Neuron 17:1173-1187.
Dannull et al. 1994, EMBO J. 13:1525-1533.
Davis et al. 1987, Nature 330:447-479.
Dayton et al. 1986, Cell 44:941-947.
De Guzman et al. 1998, Science 279:384-388.
DesGroseillers et al. 1996, Genomics 36:527-529.
Deshler et al. 1997, Science 276:1128-1131.
Deshler et al. 1998, Curr. Biol. 8:489-496.
Donzeau et al. 1997, J. Virol. 71:2628-2635.
Dorfman et al. 1993, J. Virol. 67:6159-6169.
Eckmann et al. 1997, J. Cell Biol. 138:239-253.
Elisha et al. 1995, EMBO J. 14:5109-5114.
Ephrussi et al. 1991, Cell 66:37-50.
Erdélyl et al. 1995, Nature 377:524-527.
Falcón et al. 1999, Nucleic Acids Research 27:2241-2247.
Ferrandon et al. 1994, Cell 79:1221-1232.
Ferrandon et al. 1997, EMBO J. 16:1751-1758.
Forristall et al. 1995, Development 121:201-208.
Fortin et al. 1998, J. Virol. 72:2105-2112.
Fortin et al. 1997, J. Virol. 71:3588-3596.
Gatignol et al. 1993, Mol. Cell. Biol. 13:2193-2202.
Gatignol et al. 1991, Science 251:1597-1600.
Gazzaley et al. 1997, J. Neurosci. 17:2006-2017.
Gorelick et al. 1993, J. Virol. 67:4027-4036.
Gorelick et al. 1990, J. Virol. 64:3207-3211.
Harrison et al. 1995, J. Virol. 69:2175-2186.
Havin et al. 1998, Genes & Development 12:1593-1598.
Hochstenbach et al. 1992, Proc. Natl. Acad. Sci. 89:4734-4738.
Huang et al. 1997, J. Virol. 71:4378-4384.
Jockers et al. 1996, J. Biol. Chem. 271:9355-9362.
Kang et al. 1996, Science 273:1402-1406.
Kiebler et al. 1999, J. Neuroscience 19:1-10.
Kim-Ha et al. 1991, Cell 66:23-35.
Kim-Ha et al. 1995, Cell 81:403-412.
Kimpton et al. 1992, J. Virol. 66:2232-2239.
Kislauskis et al. 1997, J. Cell Biol. 136:1263-1270.
Kloc et al. 1994, Science 265:1101-1103.
Knowles et al. 1996, J. Neuroscience 16:7812-7820.
Kraut et al. 1996, Dev. Biol. 174:65-81.
Krovat et al. 1996, J. Biol. Chem. 271:28112-28119.
Laughrea et al. 1997, J. Virol. 71:3397-3406.
Lever et al. 1989, J. Virol. 63:4085-4087.
Li et al. 1997, Cell 90:437-447.
Long et al. 1997, Science 277:383-387.
Marión et al. 1999, Mol. Cell. Biol. 19:2212-2219.
Martin et al. 1997, Cell 91:927-938.
McBride et al. 1997, J. Virol. 71:4544-4554.
McCormack et al. 1994, Virology 198:92-99.
Miele et al. 1996, J. Virol. 70:944-951.
Mizuno et al. 1996, AIDS Res. Hum. Retrov. 12:793-800.
Mouland et al. 1992, Mol. Endocrinol. 6:1781-1788.
Nakielny et al. 1997, Annu. Rev. Neurosci. 20:269-301.
Okita et al. 1994, Trends Cell Biol. 4:91-96.
Ott et al. 1995, AIDS Res. Hum. Retrov. 11:1003-1006.
Ott et al. 1996, J. Virol. 70:7734-7743.
Pachter, J.S. 1992, Crit. Rev. Euk. Gene Exp. 2:1-18.
Palker et al. 1989, J. Immunol. 142:3612-3619.
Park et al. 1994, Proc. Natl. Acad. Sci USA 91:4713-4717.
Pokrywka et al. 1995, Dev. Biol. 167:363-370.
Poon et al. 1998, J. Virol. 72:1983-1993.
Rings et al. 1994, Eur. J. Cell. Biol. 63:161-171.
Ross et al. 1997, Mol. Cell. Biol. 17:2158-2165.
Schmedt et al. 1995, J. Mol. Biol. 249:29-44.
Schumacher et al. 1995, J. Cell Biol. 129:1023-1032.
Schwartz et al. 1992, Proc. Natl. Acad. Sci. USA 89:11895-11899.
St Johnston et al. 1992, Proc. Natl. Acad. Sci. USA 89: 10979-10983.
St Johnston et al. 1991, Cell 66:51-63.
St Johnston et al. 1995, Cell 81:161-170.
St Johnston et al. 1989, Dev. (Suppl.) 107:13-19.
Steimer et al. 1986, Virology 150:283-290.
Steward, O. 1997, Neuron 18:9-12.
Takizawa et al. 1997, Nature 389:90-93.
Terasaki et al. 1986, J. Cell. Biol. 103:1557-1568.
Tetzlaff et al. 1996, The EMBO Journal 15:1247-1254.
Tiedge et al. 1993, J. Neurosci. 13:4214-4219.
Tiedge et al. 1991, Proc. Natl. Sci. USA 88:2093-2097.
Tongiorgi et al. 1997, J. Neurosci. 17:9492-9505.
Wickham et al. 1999, Mol. Cell. Biol. 19:2220-2230.
Wickham et al. 1991, DNA and Cell Biol. 10:249-258.
Wilheim et al. 1993, J. Cell Biol. 123:269-274.
Wilsch-Bräuninger et al. 1997, J. Cell Biol. 139:817-829.
Zauner et al. 1992, Eur. J. Cell Biol. 57:66-74.
Zhu et al. 1997, J. Biol. Chem. 272:14434-14441.

\* cited by examiner

Comparison of human (HUM) and mouse (MUS) staufen sequences

```
                                                                    →RBD1
HUM   MKLGKKPMYKPVDPYSRMQSTYNYNMRGGAYPPRYFYPFPVPPLLYQVELSVGGQQFNGK    60
      ::::::::.::::::.,::::::::::::::::::::::::::::::::::::
MUS         MYKPVDPHSRMQSTYSYGMRGGAYPPRYFYPFPVPPLLYQVELSVGGQQFNGK

RBD1←                   →RBD2
HUM   GKTRQAAKHDAAAKALRILQNEPLPERLEVNGRESEEENLNKSEISQVFEIALKRNLPVN   120
      ::  :....::::.,::.:.::::::::::::::::::.:::::::::::::::::::::
MUS   GKMRPPVKHDAPARALRTLQSEPLPERLEVNGREAEEENLNKSEISQVFEIALKRNLPVN

RBD2←
HUM   FEVARESGPPHMKNFVTKVSVGEFVGEGEGKSKKISKKNAAIAVLEELKKLPPLPAVERV   180
      ::::::::::::::::::::.:::::::::::::::::::::  ::::.,..:::::::
MUS   FEVARESGPPHMKNFVTRVSVGEFVGEGEGKSKKISKKNAARAVLEQLRRLPPLPAVERV

→RBD3
HUM   KPRIKKKTKPIVKPQTSPEYGQGINPISRLAQIQQAKKEKEPEYTLLTERGLPRRREFVM   240
      ::::::::.,:. :   :.:.::::,:::::::::::::::::::: ::::::::::::
MUS   KPRIKKKSQPTCK--TAPDYGQGMNPISRLAQIQQAKKEKEPEYMLLTERGLPRRREFVM

RBD3←            →TBD
HUM   QVKVGNHTAEGTGTNKKVAKRNAAENMLEILGFKVPQRQPTKPALKSEEKTPIKKPGDGR   300
      :::::  :::::.::::::::::::::::::::::::  ::.::::::::::.:::::::
MUS   QVKVGHHTAEGVGTNKKVAKRNAAENMLEILGFKVPQAQPAKPALKSEEKTPVKKPGDGR

HUM   KVTFFDPGSGDENGTSNKEDEFRMPYLSHQQLPAGILPMVPEVAQAVGVSQGHHTKDFTR   360
      :::::.::.::::::::::.::::::::::::::::::::::::::::::::::::::::
MUS   KVTFFEPSPGDENGTSNKDEEFRMPYLSHQQLPAGILPMVPEVAQAVGVSQGHHTKDFTR

TBD←
HUM   AAPNPAKATVTAMIARELLYGGTSPTAETILKNNISSGHVPHGPLTRPSEQLDYLSRVQG   420
      :::::::::::::::::::::::::::::::.:::::::::::: :::::: ::::.::
MUS   AAPNPAKATVTAMIARELLYGGTSPTAETILKSNISSGHVPHGPRTRPSEQLYYLSRAQG

→RBD4         RBD4←
HUM   FQVEYKDFPKNNKNEFVSLINCSSQPPLISHGIGKDVESCHDMAALNILKLLSELDQQST   480
      :::::::::::::::::: :::::::::::.:::::::::::::::::::::::::::::
MUS   FQVEYKDFPKNNKNECVSLINCSSQPPLVSHGIGKDVESCHDMAALNILKLLSELDQQST

HUM   EMPRTGNGPMSVCGRC*                                             496
      ::::::::::..,.:: :
MUS   EMPRTGNGPVSACGTC*
```

```
                 1
Drosophila  DRO  mqhnvhaarpaphirsahhhshahmhlhpgmeqhlgpelqcvtqDPPPPqcqpphrdlhsrlnhhhlheqqqqqtsnqsaaavsasgasayhhgnlsnsnsngsnismqkirqqh
               121
            DRO  qhlssengllgmqppppqafnplsqnpsslsynqlppphphmsshlgryssppphyymsqskpskymhygsnsnsnysapksllqntyrnqkvvvppvqsvtpvpqpp
C. elegans CEL                                                                                                      mqsvfat
(nematodes)
               241
            DRO  vttnnsttnstnstvlsssypvtqsdtssqkpsetrqspsssdhvstqmidstqslsnsdtsssqrggktdktpmolvnslsrynkitthqyrltssrgpshcktftvtlmlgd--ssysssdgf
                                                                                          >RBD1
               360
            DRO  kikksqhlssskslsstmykthpppkirrssqqgpmrthitptvslnslsmklqqrtfyl-ldptqippdtsivppsfsqqhlltspqpqmpqpppppsyslsqrlqnqfvpipsqpmhph
       human HUM                                                                                                      RBD1<
            CEL  sikrsqqssssslkqtklpiptskptkkrindttkphvvlqmvcrtlqyqmpnylscnppvvpdpqcplpshilpiseme
               479                                                                           >RBD2           RBD2<
            DRO  fhqpqqrptppkfpsrfslppplgshvhqpnqpfpsvtpppsktltlfvqkqktvqlqrtlqssskhdsssrslqvlk----tqslssessls-dsmdsgdkkspisqvhelqikrnmtv
            HUM                                                                        MRGGAYPPRKYFFD-VPPLLYQVILSVGCGQQFNGKGNKTRQAAKHDAAVAKALRILQ-----NEPLPFRLEVNGRESEEENLNKSEISQVFEIALKRNLPV
            CEL                                                                        lyspptlplpsrpqqpkiqsvlvnlngststqigqstyplskqssssksisvlspilrshqmqsdnqfqksnipvhkqksvlsdihskayqlkvnv
                                                                                                        PI    V   E    K
               595                                                                                                       >RBD3
            DRO  hfrvlrssgpshmkntflts---civgslv---tsgsqngktvsktrsssknlvslqktlppltpckqtplkrilvv-------ktpqksqsssrsgsvvsgtdqtmqtgkpsrrkrln
            HUM                   :::                                                                                   KTKPIVKPQT-SPEY
            CEL  vfsvlkssgpphdrqyvvrcsfvtsgnvvksssvqkqkkkssqqssctqllstvshltpsnnpvslstnvcktqkklsssmrspkrktlvkdktmdply----
                                                                                                      PI V E   K
            C   consensus       F V         GP H K F F        V   VG    :::         G G   SKK AK  AA  AL  L
                                Y L         R     F F         M                     G G   SKK AK  AA  AL  L
                                                  R
```

FIGURE 1' (cont'd)

```
                                                                                    >RBD4<
     698
DRO  ppkdxiidmdsdnpitkliqlqqtrtkekeplfellakhqnetarrrsfvmevaasgstarqtqnskiiakrmasqalfelleavqvtptnetqsssecctestmsavtapavaataegk
HUM  ----------GQGINPISRLAQIQQAKKEPEYTLLTERGLP--RREEFVMQVKVGNHTAEGTGTNKKVAKRNAAENRLEILGFRKVPQRQPTKPALKEEKTPIKKPGDGRKVTFFDPGS
CEL  ghqinpvariiqvtqakekehptfelvaehgvs--kykefiiqvtkygddvqegkqpnkiiakraseeaniesiqfvkiplpppqkeliikkmidcdpslpelshvtqppptav
C              P I V E  K      P F V  GP  H K F F V VG                           G G SKK AK AA AL   L
                L           R    Y L                                                        R M 818                                                                                                    >RBD5      RBD5<
DRO  vpmvatpvgpmpgililrqmkpakkrdqivivkenveeskeseankevavaseeensnsgdseneegdsqateeseslntstqsentsgvsensenvgantdqnnhaeskntes
HUM  ----------------YLSHQQLPAGILPMVPEVAQAVGVSQGHHTRDFTRAAPNP-AKATVTAMIARELLYGGTSP----TAFTILKQN-------ISSGHVPHGPLTRPS---
CEL  avstsepdtseaaqlspeqtdiseakrelspdtekirrvtfneqvhacpppqdqdypnsivqslkkdaivsqkirrikrskenrralteeqivelseraqeylqtkntiqsesqessah--
C                                                                                             G G SKK AK AA AL    L 938
DRO  senstentqesqvhmkeqllylskiidfevnfsdypkgnhnsflitivtlsethppdichgvqktsesessqmdaesenalkilskiqlnnamk*
HUM  ----------------EQLDYLSRVGFQVEYKDFPKNNRNEFVSLINCSSQPPLISHGIGKDVESCHDMAALNILKLLSELDQQSTEMPPRTGNGPMSVCGRC*
CEL  ----------hhleqlsdrfkfslqvtsfpqvdidqhftlvstqlsaplvghqtqcstteaadsnaaldaiaktikelsaekt*
C                               G G SKK AK AA AL    L B)
              230                                                                                         323
STAUFEN  GFKVPQRQPTKPALKEEKTPIKKPGDGDGRKVTFFDPGSGDENGTSNKEDEFRLPYLSHQQLPAGILPMVPEVAQAVGVSQGHHTRDFTRAAPNPDAKATVTA
MAP1B    XEKTKTKKPGTKTKSBSPVKKSDGKSKPLAASPKCPAGLKESSDKVSRVASPKKKESVEKAAKPTTTPEVKAARGEIKDKETKNANASASKSAKTATA
              2247                                                                                       2337
```

A

| Probe: | Bicoid | Bicoid | Bicoid | p(rI)-p(rC) | p(rI)-p(rC) | DNA |
| --- | --- | --- | --- | --- | --- | --- |
| Competitors: | | p(rI)-p(rC) | p(rC) | - | p(rC) | - |

B

Probe: p(rA)-p(U)   p(dA)-p(U)   p(dA)   p(U)   p(rC)   p(rA)

SEQUENCE LISTING

<160> NUMBER OF SEQ ID NOS: 27

<210> SEQ ID NO 1
<211> LENGTH: 3506
<212> TYPE: DNA
<213> ORGANISM: Homo sapiens
<220> FEATURE:
<221> NAME/KEY: CDS
<222> LOCATION: (409)..(2139)
<223> OTHER INFORMATION:

<400> SEQUENCE: 1

```
acttcctgcc gggctgcggg cgcctgagcg ctcttcagcg tttgcgcggc ggctgcgcgt      60
ctctctcggc tcccgcttcc tttgaccgcc tccccccccc ggcccggcgg cgcccgcctc     120
ctccacggcc actccgcctc ttccctccct tcgtcccttc ttcctctccc ttttttcctt     180
cttccttccc ctcctcgccg ccaccgccca ggaccgccgg ccgggggacg agtccggagc     240
agcagccaga gtttattaac cacttaacct ctcagaactg aacaaagaca acattgttcc     300
tggaacgccc tcttttttaaa aaaggtagaa ctttagactt catagcactg aattaacctg     360
cactgaaagc tgtttacctg catttgttca cttttgttga aagtgacc atg tct caa       417
                                                     Met Ser Gln
                                                       1
```

```
gtt caa gtg caa gtt cag aac cca tct gct gct ctc tca ggg agc caa       465
Val Gln Val Gln Val Gln Asn Pro Ser Ala Ala Leu Ser Gly Ser Gln
     5                  10                  15 ata ctg aac aag aac cag tct ctt ctc tca cag cct ttg atg agt att       513
Ile Leu Asn Lys Asn Gln Ser Leu Leu Ser Gln Pro Leu Met Ser Ile
 20                  25                  30                  35 cct tct act act agc tct ctg ccc tct gaa aat gca ggt aga ccc att       561
Pro Ser Thr Thr Ser Ser Leu Pro Ser Glu Asn Ala Gly Arg Pro Ile
             40                  45                  50 caa aac tct gct tta ccc tct gca tct att aca tcc acc agt gca gct       609
Gln Asn Ser Ala Leu Pro Ser Ala Ser Ile Thr Ser Thr Ser Ala Ala
         55                  60                  65 gca gaa agc ata acc cct act gta gaa cta aat gca ctg tgc atg aaa       657
Ala Glu Ser Ile Thr Pro Thr Val Glu Leu Asn Ala Leu Cys Met Lys
     70                  75                  80 ctt gga aaa aaa cca atg tat aag cct gtt gac cct tac tct cgg atg       705
Leu Gly Lys Lys Pro Met Tyr Lys Pro Val Asp Pro Tyr Ser Arg Met
 85                  90                  95 cag tcc acc tat aac tac aac atg aga gga ggt gct tat ccc ccg agg       753
Gln Ser Thr Tyr Asn Tyr Asn Met Arg Gly Gly Ala Tyr Pro Pro Arg
100                 105                 110                 115 tac ttt tac cca ttt cca gtt cca cct tta ctt tat caa gtg gaa ctt       801
Tyr Phe Tyr Pro Phe Pro Val Pro Pro Leu Leu Tyr Gln Val Glu Leu
             120                 125                 130 tct gtg gga gga cag caa ttt aat ggc aaa gga aag aca aga cag gct       849
Ser Val Gly Gly Gln Gln Phe Asn Gly Lys Gly Lys Thr Arg Gln Ala
         135                 140                 145 gcg aaa cac gat gct gct gcc aaa gcg ttg agg atc ctg cag aat gag       897
Ala Lys His Asp Ala Ala Ala Lys Ala Leu Arg Ile Leu Gln Asn Glu
     150                 155                 160 ccc ctg cca gag agg ctg gag gtg aat gga aga gaa tcc gaa gaa gaa       945
Pro Leu Pro Glu Arg Leu Glu Val Asn Gly Arg Glu Ser Glu Glu Glu
 165                 170                 175 aat ctc aat aaa tct gaa ata agt caa gtg ttt gag att gca ctt aaa       993
Asn Leu Asn Lys Ser Glu Ile Ser Gln Val Phe Glu Ile Ala Leu Lys
180                 185                 190                 195
```

-continued

| | |
|---|---|
| cgg aac ttg cct gtg aat ttc gag gtg gcc cgg gag agt ggc cca ccc<br>Arg Asn Leu Pro Val Asn Phe Glu Val Ala Arg Glu Ser Gly Pro Pro<br>200 205 210 | 1041 |
| cac atg aag aac ttt gtg acc aag gtt tcg gtt ggg gag ttt gtg ggg<br>His Met Lys Asn Phe Val Thr Lys Val Ser Val Gly Glu Phe Val Gly<br>215 220 225 | 1089 |
| gaa ggt gaa ggg aaa agc aag aag att tca aag aaa aat gcc gcc ata<br>Glu Gly Glu Gly Lys Ser Lys Lys Ile Ser Lys Lys Asn Ala Ala Ile<br>230 235 240 | 1137 |
| gct gtt ctt gag gag ctg aag aag tta ccg ccc ctg cct gca gtt gaa<br>Ala Val Leu Glu Glu Leu Lys Lys Leu Pro Pro Leu Pro Ala Val Glu<br>245 250 255 | 1185 |
| cga gta aag cct aga atc aaa aag aaa aca aaa ccc ata gtc aag cca<br>Arg Val Lys Pro Arg Ile Lys Lys Lys Thr Lys Pro Ile Val Lys Pro<br>260 265 270 275 | 1233 |
| cag aca agc cca gaa tat ggc cag ggg atc aat ccg att agc cga ctg<br>Gln Thr Ser Pro Glu Tyr Gly Gln Gly Ile Asn Pro Ile Ser Arg Leu<br>280 285 290 | 1281 |
| gcc cag atc cag cag gca aaa aag gag aag gag cca gag tac acg ctc<br>Ala Gln Ile Gln Gln Ala Lys Lys Glu Lys Glu Pro Glu Tyr Thr Leu<br>295 300 305 | 1329 |
| ctc aca gag cga ggc ctc ccg cgc cgc agg gag ttt gtg atg cag gtg<br>Leu Thr Glu Arg Gly Leu Pro Arg Arg Arg Glu Phe Val Met Gln Val<br>310 315 320 | 1377 |
| aag gtt gga aac cac act gca gaa gga acg ggc acc aac aag aag gtg<br>Lys Val Gly Asn His Thr Ala Glu Gly Thr Gly Thr Asn Lys Lys Val<br>325 330 335 | 1425 |
| gcc aag cgc aat gca gcc gag aac atg ctg gag atc ctt ggt ttc aaa<br>Ala Lys Arg Asn Ala Ala Glu Asn Met Leu Glu Ile Leu Gly Phe Lys<br>340 345 350 355 | 1473 |
| gtc ccg cag cgg cag ccc acc aaa ccc gca ctc aag tca gag gag aag<br>Val Pro Gln Arg Gln Pro Thr Lys Pro Ala Leu Lys Ser Glu Glu Lys<br>360 365 370 | 1521 |
| aca ccc ata aag aaa cca ggg gat gga aga aaa gta acc ttt ttt gaa<br>Thr Pro Ile Lys Lys Pro Gly Asp Gly Arg Lys Val Thr Phe Phe Glu<br>375 380 385 | 1569 |
| cct ggc tct ggg gat gaa aat ggg act agt aat aaa gag gat gag ttc<br>Pro Gly Ser Gly Asp Glu Asn Gly Thr Ser Asn Lys Glu Asp Glu Phe<br>390 395 400 | 1617 |
| agg atg cct tat cta agt cat cag cag ctg cct gct gga att ctt ccc<br>Arg Met Pro Tyr Leu Ser His Gln Gln Leu Pro Ala Gly Ile Leu Pro<br>405 410 415 | 1665 |
| atg gtg ccc gag gtc gcc cag gct gta gga gtt agt caa gga cat cac<br>Met Val Pro Glu Val Ala Gln Ala Val Gly Val Ser Gln Gly His His<br>420 425 430 435 | 1713 |
| acc aaa gat ttt acc agg gca gct ccg aat cct gcc aag gcc acg gta<br>Thr Lys Asp Phe Thr Arg Ala Ala Pro Asn Pro Ala Lys Ala Thr Val<br>440 445 450 | 1761 |
| act gcc atg ata gcc cga gag ttg ttg tat ggg ggc acc tcg ccc aca<br>Thr Ala Met Ile Ala Arg Glu Leu Leu Tyr Gly Gly Thr Ser Pro Thr<br>455 460 465 | 1809 |
| gcc gag acc att tta aag aat aac atc tct tca ggc cac gta ccc cat<br>Ala Glu Thr Ile Leu Lys Asn Asn Ile Ser Ser Gly His Val Pro His<br>470 475 480 | 1857 |
| gga cct ctc acg aga ccc tct gag caa ctg gac tat ctt tcc aga gtc<br>Gly Pro Leu Thr Arg Pro Ser Glu Gln Leu Asp Tyr Leu Ser Arg Val<br>485 490 495 | 1905 |
| cag gga ttc cag gtt gaa tac aaa gac ttc ccc aaa aac aac aag aac<br>Gln Gly Phe Gln Val Glu Tyr Lys Asp Phe Pro Lys Asn Asn Lys Asn | 1953 |

-continued

| | | | |
|---|---|---|---|
| | 500 | 505 | 510 | 515 | | |
| gaa ttt gta tct ctt atc aat tgc tcc tct cag cca cct ctg atc agc<br>Glu Phe Val Ser Leu Ile Asn Cys Ser Ser Gln Pro Pro Leu Ile Ser<br>520                 525               530 | 2001 |
| cat ggt atc ggc aag gat gtg gag tcc tgc cat gat atg gct gcg ctg<br>His Gly Ile Gly Lys Asp Val Glu Ser Cys His Asp Met Ala Ala Leu<br>535                 540               545 | 2049 |
| aac atc tta aag ttg ctg tct gag ttg gac caa caa agt aca gag atg<br>Asn Ile Leu Lys Leu Leu Ser Glu Leu Asp Gln Gln Ser Thr Glu Met<br>550                 555               560 | 2097 |
| cca aga aca gga aac gga cca atg tct gtg tgt ggg agg tgc<br>Pro Arg Thr Gly Asn Gly Pro Met Ser Val Cys Gly Arg Cys<br>565                 570               575 | 2139 |
| tgaaccttt ctggccatga accattataa aatcccaaca tatatactga aaatactgaa | 2199 |
| actgctttga aaatttggaa tttctgatac ctccagtggg ccgagagaca cggtgggtaa | 2259 |
| aggatgtggg cagcagcagg gaagacaaca gaaacacaag gaggcggctg tggccggctg | 2319 |
| gactgtgctg gggtttgttg tgatggccac tcggtgacct ggcggtccct acgcaatagc | 2379 |
| agctgcctgt ggggaagaag ggctgcccag ccagctggtt ctcccgggac cagcagat | 2439 |
| ccacaccctg gcacctccg tgtttggtct ttttttttccc ctgtgtgaaa gaagaaacgg | 2499 |
| cacgacccct tctcaagctg gctcactcag acacattggg acaaaccctg acagccatg | 2559 |
| ccagagagag gcctttgacc ggccccagag ctaaaagcac cagagaaaat caaatgcttc | 2619 |
| ctactcagcg tgacccaact tttcagtgt gccacggccc caccacctcc tgcagtaccc | 2679 |
| acaccatcac cactgctttc tcttccaaca gtgatctgta ttcttagttt cattattttc | 2739 |
| ttttgattga tatgcacta tataaaattt tcatttgaga atttctcaat tgtatctagt | 2799 |
| taaatagcac agtttggaaa cttgtctgag actgacttta tcaataatct aaccgacaaa | 2859 |
| gatcatatcc atgtgtatgt ggttagacat ttttatttca ttgactaacc caggacagtt | 2919 |
| tcagtgatgc aaattgtgtg ccctctggtt cagctgaaac agtcctggac tttcaaaaac | 2979 |
| cttgaataag tctcccacag ttgtataaat tggacaattt aggaatttta aactttagat | 3039 |
| gatcatttgg ttccattttt atttcatttt tattttttgtt aatgcaaaca ggacttaaat | 3099 |
| gaactttgat ctctgtttta aagattatta aaaaacattg tgtatctata catatggctc | 3159 |
| ttgaggactt agctttcact acactacagg atatgatctc catgtagtcc atataaacct | 3219 |
| gcagagtgat tttccagagt gctcgatact gttaattaca tctccattag ggctgaaaag | 3279 |
| aatgacctac gtttctgtat acagctgtgt tgcttttgat gttgtgttac tgtacacaga | 3339 |
| agtgtgtgca ctgaggctct gcgtgtggtc cgtatggaaa acctggtagc cctgcgagtt | 3399 |
| aagtactgct tccattcatt gtttacgctg gaatttttct ccccatggaa tgtaagtaaa | 3459 |
| acttaagtgt ttgtcatcaa taaatggtaa tactaaaaaa aaaaaaa | 3506 |

<210> SEQ ID NO 2
<211> LENGTH: 577
<212> TYPE: PRT
<213> ORGANISM: Homo sapiens

<400> SEQUENCE: 2

Met Ser Gln Val Gln Val Gln Val Gln Asn Pro Ser Ala Ala Leu Ser
1               5                   10                  15

Gly Ser Gln Ile Leu Asn Lys Asn Gln Ser Leu Leu Ser Gln Pro Leu
            20                  25                  30

Met Ser Ile Pro Ser Thr Thr Ser Ser Leu Pro Ser Glu Asn Ala Gly

-continued

```
                35                  40                  45
Arg Pro Ile Gln Asn Ser Ala Leu Pro Ser Ala Ser Ile Thr Ser Thr
        50                  55                  60

Ser Ala Ala Glu Ser Ile Thr Pro Thr Val Glu Leu Asn Ala Leu
 65                  70                  75                  80

Cys Met Lys Leu Gly Lys Lys Pro Met Tyr Lys Pro Val Asp Pro Tyr
                    85                  90                  95

Ser Arg Met Gln Ser Thr Tyr Asn Tyr Asn Met Arg Gly Gly Ala Tyr
                100                 105                 110

Pro Pro Arg Tyr Phe Tyr Pro Phe Pro Val Pro Pro Leu Leu Tyr Gln
            115                 120                 125

Val Glu Leu Ser Val Gly Gly Gln Gln Phe Asn Gly Lys Gly Lys Thr
130                 135                 140

Arg Gln Ala Ala Lys His Asp Ala Ala Lys Ala Leu Arg Ile Leu
145                 150                 155                 160

Gln Asn Glu Pro Leu Pro Glu Arg Leu Glu Val Asn Gly Arg Glu Ser
                    165                 170                 175

Glu Glu Glu Asn Leu Asn Lys Ser Glu Ile Ser Gln Val Phe Glu Ile
                180                 185                 190

Ala Leu Lys Arg Asn Leu Pro Val Asn Phe Glu Val Ala Arg Glu Ser
            195                 200                 205

Gly Pro Pro His Met Lys Asn Phe Val Thr Lys Val Ser Val Gly Glu
        210                 215                 220

Phe Val Gly Glu Gly Glu Gly Lys Ser Lys Lys Ile Ser Lys Lys Asn
225                 230                 235                 240

Ala Ala Ile Ala Val Leu Glu Glu Leu Lys Lys Leu Pro Pro Leu Pro
                    245                 250                 255

Ala Val Glu Arg Val Lys Pro Arg Ile Lys Lys Thr Lys Pro Ile
                260                 265                 270

Val Lys Pro Gln Thr Ser Pro Glu Tyr Gly Gln Gly Ile Asn Pro Ile
            275                 280                 285

Ser Arg Leu Ala Gln Ile Gln Gln Ala Lys Lys Glu Lys Glu Pro Glu
290                 295                 300

Tyr Thr Leu Leu Thr Glu Arg Gly Leu Pro Arg Arg Arg Glu Phe Val
305                 310                 315                 320

Met Gln Val Lys Val Gly Asn His Thr Ala Glu Gly Thr Gly Thr Asn
                    325                 330                 335

Lys Lys Val Ala Lys Arg Asn Ala Ala Glu Asn Met Leu Glu Ile Leu
                340                 345                 350

Gly Phe Lys Val Pro Gln Arg Gln Pro Thr Lys Pro Ala Leu Lys Ser
            355                 360                 365

Glu Glu Lys Thr Pro Ile Lys Lys Pro Gly Asp Gly Arg Lys Val Thr
370                 375                 380

Phe Phe Glu Pro Gly Ser Gly Asp Glu Asn Gly Thr Ser Asn Lys Glu
385                 390                 395                 400

Asp Glu Phe Arg Met Pro Tyr Leu Ser His Gln Gln Leu Pro Ala Gly
                    405                 410                 415

Ile Leu Pro Met Val Pro Glu Val Ala Gln Ala Val Gly Val Ser Gln
                420                 425                 430

Gly His His Thr Lys Asp Phe Thr Arg Ala Ala Pro Asn Pro Ala Lys
            435                 440                 445

Ala Thr Val Thr Ala Met Ile Ala Arg Glu Leu Leu Tyr Gly Gly Thr
450                 455                 460
```

```
Ser Pro Thr Ala Glu Thr Ile Leu Lys Asn Asn Ile Ser Ser Gly His
465                 470                 475                 480

Val Pro His Gly Pro Leu Thr Arg Pro Ser Glu Gln Leu Asp Tyr Leu
                485                 490                 495

Ser Arg Val Gln Gly Phe Gln Val Glu Tyr Lys Asp Phe Pro Lys Asn
            500                 505                 510

Asn Lys Asn Glu Phe Val Ser Leu Ile Asn Cys Ser Ser Gln Pro Pro
        515                 520                 525

Leu Ile Ser His Gly Ile Gly Lys Asp Val Glu Ser Cys His Asp Met
    530                 535                 540

Ala Ala Leu Asn Ile Leu Lys Leu Leu Ser Glu Leu Asp Gln Gln Ser
545                 550                 555                 560

Thr Glu Met Pro Arg Thr Gly Asn Gly Pro Met Ser Val Cys Gly Arg
                565                 570                 575

Cys

<210> SEQ ID NO 3
<211> LENGTH: 3217
<212> TYPE: DNA
<213> ORGANISM: Homo sapiens
<220> FEATURE:
<221> NAME/KEY: CDS
<222> LOCATION: (363)..(1850)
<223> OTHER INFORMATION:

<400> SEQUENCE: 3
acttcctgcc gggctgcggg cgcctgagcg ctcttcagcg tttgcgcggc ggctgcgcgt      60
ctctctcggc tcccgcttcc tttgaccgcc tcccccccc ggcccggcgg cgcccgcctc     120
ctccacggcc actccgcctc ttccctccct tcgtcccttc ttcctctccc ttttttcctt     180
cttccttccc ctcctcgccg ccaccgccca ggaccgccgg ccgggggacg agtccggagc     240
agcagccaga gtttattaac cacttaacct ctcagaactg aacaaagaca acattgttcc     300
tggaacgccc tcttttttaaa aaagaaagca taaccctac tgtagaacta atgcactgt     360 gc atg aaa ctt gga aaa aaa cca atg tat aag cct gtt gac cct tac        407
   Met Lys Leu Gly Lys Lys Pro Met Tyr Lys Pro Val Asp Pro Tyr
   1               5                  10                  15 tct cgg atg cag tcc acc tat aac tac aac atg aga gga ggt gct tat       455
Ser Arg Met Gln Ser Thr Tyr Asn Tyr Asn Met Arg Gly Gly Ala Tyr
            20                  25                  30 ccc ccg agg tac ttt tac cca ttt cca gtt cca cct tta ctt tat caa       503
Pro Pro Arg Tyr Phe Tyr Pro Phe Pro Val Pro Pro Leu Leu Tyr Gln
        35                  40                  45 gtg gaa ctt tct gtg gga gga cag caa ttt aat ggc aaa gga aag aca       551
Val Glu Leu Ser Val Gly Gly Gln Gln Phe Asn Gly Lys Gly Lys Thr
    50                  55                  60 aga cag gct gcg aaa cac gat gct gct gcc aaa gcg ttg agg atc ctg       599
Arg Gln Ala Ala Lys His Asp Ala Ala Ala Lys Ala Leu Arg Ile Leu
65                  70                  75 cag aat gag ccc ctg cca gag agg ctg gag gtg aat gga aga gaa tcc       647
Gln Asn Glu Pro Leu Pro Glu Arg Leu Glu Val Asn Gly Arg Glu Ser
 80                  85                  90                  95 gaa gaa gaa aat ctc aat aaa tct gaa ata agt caa gtg ttt gag att       695
Glu Glu Glu Asn Leu Asn Lys Ser Glu Ile Ser Gln Val Phe Glu Ile
                100                 105                 110 gca ctt aaa cgg aac ttg cct gtg aat ttc gag gtg gcc cgg gag agt       743
Ala Leu Lys Arg Asn Leu Pro Val Asn Phe Glu Val Ala Arg Glu Ser
            115                 120                 125
```

-continued

| | | |
|---|---|---|
| ggc cca ccc cac atg aag aac ttt gtg acc aag gtt tcg gtt ggg gag<br>Gly Pro Pro His Met Lys Asn Phe Val Thr Lys Val Ser Val Gly Glu<br>130               135               140 | 791 |
| ttt gtg ggg gaa ggt gaa ggg aaa agc aag aag att tca aag aaa aat<br>Phe Val Gly Glu Gly Glu Gly Lys Ser Lys Lys Ile Ser Lys Lys Asn<br>145                150               155 | 839 |
| gcc gcc ata gct gtt ctt gag gag ctg aag aag tta ccg ccc ctg cct<br>Ala Ala Ile Ala Val Leu Glu Glu Leu Lys Lys Leu Pro Pro Leu Pro<br>160               165            170             175 | 887 |
| gca gtt gaa cga gta aag cct aga atc aaa aag aaa aca aaa ccc ata<br>Ala Val Glu Arg Val Lys Pro Arg Ile Lys Lys Thr Lys Pro Ile<br>                 180            185              190 | 935 |
| gtc aag cca cag aca agc cca gaa tat ggc cag ggg atc aat ccg att<br>Val Lys Pro Gln Thr Ser Pro Glu Tyr Gly Gln Gly Ile Asn Pro Ile<br>         195                200             205 | 983 |
| agc cga ctg gcc cag atc cag cag gca aaa aag gag aag gag cca gag<br>Ser Arg Leu Ala Gln Ile Gln Gln Ala Lys Lys Glu Lys Glu Pro Glu<br>             210              215             220 | 1031 |
| tac acg ctc ctc aca gag cga ggc ctc ccg cgc cgc agg gag ttt gtg<br>Tyr Thr Leu Leu Thr Glu Arg Gly Leu Pro Arg Arg Arg Glu Phe Val<br>225                230               235 | 1079 |
| atg cag gtg aag gtt gga aac cac act gca gaa gga acg ggc acc aac<br>Met Gln Val Lys Val Gly Asn His Thr Ala Glu Gly Thr Gly Thr Asn<br>240               245            250             255 | 1127 |
| aag aag gtg gcc aag cgc aat gca gcc gag aac atg ctg gag atc ctt<br>Lys Lys Val Ala Lys Arg Asn Ala Ala Glu Asn Met Leu Glu Ile Leu<br>             260              265             270 | 1175 |
| ggt ttc aaa gtc ccg cag cgg cag ccc acc aaa ccc gca ctc aag tca<br>Gly Phe Lys Val Pro Gln Arg Gln Pro Thr Lys Pro Ala Leu Lys Ser<br>         275               280            285 | 1223 |
| gag gag aag aca ccc ata aag aaa cca ggg gat gga aga aaa gta acc<br>Glu Glu Lys Thr Pro Ile Lys Lys Pro Gly Asp Gly Arg Lys Val Thr<br>             290              295            300 | 1271 |
| ttt ttt gaa cct ggc tct ggg gat gaa aat ggg act agt aat aaa gag<br>Phe Phe Glu Pro Gly Ser Gly Asp Glu Asn Gly Thr Ser Asn Lys Glu<br>305                310               315 | 1319 |
| gat gag ttc agg atg cct tat cta agt cat cag cag ctg cct gct gga<br>Asp Glu Phe Arg Met Pro Tyr Leu Ser His Gln Gln Leu Pro Ala Gly<br>320                325            330             335 | 1367 |
| att ctt ccc atg gtg ccc gag gtc gcc cag gct gta gga gtt agt caa<br>Ile Leu Pro Met Val Pro Glu Val Ala Gln Ala Val Gly Val Ser Gln<br>                 340             345             350 | 1415 |
| gga cat cac acc aaa gat ttt acc agg gca gct ccg aat cct gcc aag<br>Gly His His Thr Lys Asp Phe Thr Arg Ala Ala Pro Asn Pro Ala Lys<br>         355               360            365 | 1463 |
| gcc acg gta act gcc atg ata gcc cga gag ttg ttg tat ggg ggc acc<br>Ala Thr Val Thr Ala Met Ile Ala Arg Glu Leu Leu Tyr Gly Gly Thr<br>             370              375             380 | 1511 |
| tcg ccc aca gcc gag acc att tta aag aat aac atc tct tca ggc cac<br>Ser Pro Thr Ala Glu Thr Ile Leu Lys Asn Asn Ile Ser Ser Gly His<br>385                390               395 | 1559 |
| gta ccc cat gga cct ctc acg aga ccc tct gag caa ctg gac tat ctt<br>Val Pro His Gly Pro Leu Thr Arg Pro Ser Glu Gln Leu Asp Tyr Leu<br>400                405            410             415 | 1607 |
| tcc aga gtc cag gga ttc cag gtt gaa tac aaa gac ttc ccc aaa aac<br>Ser Arg Val Gln Gly Phe Gln Val Glu Tyr Lys Asp Phe Pro Lys Asn<br>             420              425             430 | 1655 |
| aac aag aac gaa ttt gta tct ctt atc aat tgc tcc tct cag cca cct<br>Asn Lys Asn Glu Phe Val Ser Leu Ile Asn Cys Ser Ser Gln Pro Pro | 1703 |

```
                    435                 440                 445
ctg atc agc cat ggt atc ggc aag gat gtg gag tcc tgc cat gat atg        1751
Leu Ile Ser His Gly Ile Gly Lys Asp Val Glu Ser Cys His Asp Met
            450                 455                 460 gct gcg ctg aac atc tta aag ttg ctg tct gag ttg gac caa caa agt        1799
Ala Ala Leu Asn Ile Leu Lys Leu Leu Ser Glu Leu Asp Gln Gln Ser
        465                 470                 475 aca gag atg cca aga aca gga aac gga cca atg tct gtg tgt ggg agg        1847
Thr Glu Met Pro Arg Thr Gly Asn Gly Pro Met Ser Val Cys Gly Arg
480                 485                 490                 495 tgc tgaacctttt ctggccatga accattataa aatcccaaca tatatactga             1900
Cys aaatactgaa actgctttga aaatttggaa tttctgatac ctccagtggg ccgagagaca      1960
cggtgggtaa aggatgtggg cagcagcagg gaagacaaca gaaacacaag gaggcggctg      2020
tggccggctg gactgtgctg gggtttgttg tgatggccac tcggtgacct ggcggtccct      2080
acgcaatagc agctgcctgt ggggaagaag ggctgcccag ccagctggtt ctcccgggac      2140
accagcagat ccacccctg gcacctccg tgtttggtct tttttttccc ctgtgtgaaa        2200
gaagaaacgg cacgacccct tctcaagctg gctcactcag acacattggg acaaaccctg      2260
gacagccatg ccagagagag gcctttgacc ggccccagag ctaaaagcac cagagaaaat      2320
caaatgcttc ctactcagcg tgacccaact tttctagtgt gccacggccc caccacctcc      2380
tgcagtaccc acaccatcac cactgctttc tcttccaaca gtgatctgta ttcttagttt      2440
cattattttc ttttgattga tatgacacta tataaaattt tcatttgaga atttctcaat      2500
tgtatctagt taaatagcac agtttggaaa cttgtctgag actgacttta tcaataatct      2560
aaccgacaaa gatcatatcc atgtgtatgt ggttagacat ttttatttca ttgactaacc      2620
caggacagtt tcagtgatgc aaattgtgtg ccctctggtt cagctgaaac agtcctggac      2680
tttcaaaaac cttgaataag tctcccacag ttgtataaat tggacaattt aggaatttta      2740
aactttagat gatcattggg ttccattttt atttcatttt tattttgtt aatgcaaaca       2800
ggacttaaat gaactttgat ctctgtttta aagattatta aaaacattg tgtatctata       2860
catatggctc ttgaggactt agctttcact acactacagg atatgatctc catgtagtcc      2920
atataaacct gcagagtgat tttccagagt gctcgatact gttaattaca ctctccattag     2980
ggctgaaaag aatgacctac gtttctgtat acagctgtgt tgcttttgat gttgtgttac      3040
tgtacacaga agtgtgtgca ctgaggctct gcgtgtggtc cgtatggaaa acctggtagc      3100
cctgcgagtt aagtactgct tccattcatt gtttacgctg gaattttct ccccatggaa       3160
tgtaagtaaa acttaagtgt ttgtcatcaa taaatggtaa tactaaaaaa aaaaaaa        3217
```

<210> SEQ ID NO 4
<211> LENGTH: 496
<212> TYPE: PRT
<213> ORGANISM: Homo sapiens

<400> SEQUENCE: 4

```
Met Lys Leu Gly Lys Lys Pro Met Tyr Lys Pro Val Asp Pro Tyr Ser
 1               5                  10                  15

Arg Met Gln Ser Thr Tyr Asn Tyr Asn Met Arg Gly Gly Ala Tyr Pro
            20                  25                  30

Pro Arg Tyr Phe Tyr Pro Phe Pro Val Pro Pro Leu Leu Tyr Gln Val
        35                  40                  45

Glu Leu Ser Val Gly Gly Gln Gln Phe Asn Gly Lys Gly Lys Thr Arg
```

-continued

```
                50                  55                  60
Gln Ala Ala Lys His Asp Ala Ala Lys Ala Leu Arg Ile Leu Gln
 65                  70                  75                  80

Asn Glu Pro Leu Pro Glu Arg Leu Glu Val Asn Gly Arg Ser Glu
                 85                  90                  95

Glu Glu Asn Leu Asn Lys Ser Glu Ile Ser Gln Val Phe Glu Ile Ala
                100                 105                 110

Leu Lys Arg Asn Leu Pro Val Asn Phe Glu Val Ala Arg Glu Ser Gly
                115                 120                 125

Pro Pro His Met Lys Asn Phe Val Thr Lys Val Ser Val Gly Glu Phe
130                 135                 140

Val Gly Glu Gly Glu Gly Lys Ser Lys Lys Ile Ser Lys Lys Asn Ala
145                 150                 155                 160

Ala Ile Ala Val Leu Glu Glu Leu Lys Lys Leu Pro Pro Leu Pro Ala
                165                 170                 175

Val Glu Arg Val Lys Pro Arg Ile Lys Lys Thr Lys Pro Ile Val
                180                 185                 190

Lys Pro Gln Thr Ser Pro Glu Tyr Gly Gln Gly Ile Asn Pro Ile Ser
                195                 200                 205

Arg Leu Ala Gln Ile Gln Gln Ala Lys Lys Glu Lys Glu Pro Glu Tyr
                210                 215                 220

Thr Leu Leu Thr Glu Arg Gly Leu Pro Arg Arg Glu Phe Val Met
225                 230                 235                 240

Gln Val Lys Val Gly Asn His Thr Ala Glu Gly Thr Gly Thr Asn Lys
                245                 250                 255

Lys Val Ala Lys Arg Asn Ala Ala Glu Asn Met Leu Glu Ile Leu Gly
                260                 265                 270

Phe Lys Val Pro Gln Arg Gln Pro Thr Lys Pro Ala Leu Lys Ser Glu
                275                 280                 285

Glu Lys Thr Pro Ile Lys Lys Pro Gly Asp Gly Arg Lys Val Thr Phe
                290                 295                 300

Phe Glu Pro Gly Ser Gly Asp Glu Asn Gly Thr Ser Asn Lys Glu Asp
305                 310                 315                 320

Glu Phe Arg Met Pro Tyr Leu Ser His Gln Gln Leu Pro Ala Gly Ile
                325                 330                 335

Leu Pro Met Val Pro Glu Val Ala Gln Ala Val Gly Val Ser Gln Gly
                340                 345                 350

His His Thr Lys Asp Phe Thr Arg Ala Ala Pro Asn Pro Ala Lys Ala
                355                 360                 365

Thr Val Thr Ala Met Ile Ala Arg Glu Leu Leu Tyr Gly Gly Thr Ser
                370                 375                 380

Pro Thr Ala Glu Thr Ile Leu Lys Asn Asn Ile Ser Ser Gly His Val
385                 390                 395                 400

Pro His Gly Pro Leu Thr Arg Pro Ser Glu Gln Leu Asp Tyr Leu Ser
                405                 410                 415

Arg Val Gln Gly Phe Gln Val Glu Tyr Lys Asp Phe Pro Lys Asn Asn
                420                 425                 430

Lys Asn Glu Phe Val Ser Leu Ile Asn Cys Ser Ser Gln Pro Pro Leu
                435                 440                 445

Ile Ser His Gly Ile Gly Lys Asp Val Glu Ser Cys His Asp Met Ala
                450                 455                 460

Ala Leu Asn Ile Leu Lys Leu Leu Ser Glu Leu Asp Gln Gln Ser Thr
465                 470                 475                 480
```

```
                Glu Met Pro Arg Thr Gly Asn Gly Pro Met Ser Val Cys Gly Arg Cys
                            485                 490                 495

<210> SEQ ID NO 5
<211> LENGTH: 3142
<212> TYPE: DNA
<213> ORGANISM: Homo sapiens
<220> FEATURE:
<221> NAME/KEY: CDS
<222> LOCATION: (288)..(1775)
<223> OTHER INFORMATION:

<400> SEQUENCE: 5
acttcctgcc gggctgcggg cgcctgagcg ctcttcagcg tttgcgcggc ggctgcgcgt      60
ctctctcggc tcccgcttcc tttgaccgcc tcccccccc  ggcccggcgg cgcccgcctc     120
ctccacggcc actccgcctc ttccctccct tcgtcccttc ttcctctccc tttttccctt    180
cttccttccc ctcctcgccg ccaccgccca ggaccgccgg ccgggggacg agtccggagc    240
agcagccaga aagcataacc cctactgtag aactaaatgc actgtgc atg aaa ctt       296
                                                    Met Lys Leu
                                                      1 gga aaa aaa cca atg tat aag cct gtt gac cct tac tct cgg atg cag      344
Gly Lys Lys Pro Met Tyr Lys Pro Val Asp Pro Tyr Ser Arg Met Gln
    5                  10                  15 tcc acc tat aac tac aac atg aga gga ggt gct tat ccc ccg agg tac      392
Ser Thr Tyr Asn Tyr Asn Met Arg Gly Gly Ala Tyr Pro Pro Arg Tyr
 20                  25                  30                  35 ttt tac cca ttt cca gtt cca cct tta ctt tat caa gtg gaa ctt tct      440
Phe Tyr Pro Phe Pro Val Pro Pro Leu Leu Tyr Gln Val Glu Leu Ser
                40                  45                  50 gtg gga gga cag caa ttt aat ggc aaa gga aag aca aga cag gct gcg      488
Val Gly Gly Gln Gln Phe Asn Gly Lys Gly Lys Thr Arg Gln Ala Ala
            55                  60                  65 aaa cac gat gct gct gcc aaa gcg ttg agg atc ctg cag aat gag ccc      536
Lys His Asp Ala Ala Ala Lys Ala Leu Arg Ile Leu Gln Asn Glu Pro
        70                  75                  80 ctg cca gag agg ctg gag gtg aat gga aga gaa tcc gaa gaa gaa aat      584
Leu Pro Glu Arg Leu Glu Val Asn Gly Arg Glu Ser Glu Glu Glu Asn
    85                  90                  95 ctc aat aaa tct gaa ata agt caa gtg ttt gag att gca ctt aaa cgg      632
Leu Asn Lys Ser Glu Ile Ser Gln Val Phe Glu Ile Ala Leu Lys Arg
100                 105                 110                 115 aac ttg cct gtg aat ttc gag gtg gcc cgg gag agt ggc cca ccc cac      680
Asn Leu Pro Val Asn Phe Glu Val Ala Arg Glu Ser Gly Pro Pro His
                120                 125                 130 atg aag aac ttt gtg acc aag gtt tcg gtt ggg gag ttt gtg ggg gaa      728
Met Lys Asn Phe Val Thr Lys Val Ser Val Gly Glu Phe Val Gly Glu
            135                 140                 145 ggt gaa ggg aaa agc aag aag att tca aag aaa aat gcc gcc ata gct      776
Gly Glu Gly Lys Ser Lys Lys Ile Ser Lys Lys Asn Ala Ala Ile Ala
        150                 155                 160 gtt ctt gag gag ctg aag aag tta ccg ccc ctg cct gca gtt gaa cga      824
Val Leu Glu Glu Leu Lys Lys Leu Pro Pro Leu Pro Ala Val Glu Arg
    165                 170                 175 gta aag cct aga atc aaa aag aaa aca aaa ccc ata gtc aag cca cag      872
Val Lys Pro Arg Ile Lys Lys Lys Thr Lys Pro Ile Val Lys Pro Gln
180                 185                 190                 195 aca agc cca gaa tat ggc cag ggg atc aat ccg att agc cga ctg gcc      920
Thr Ser Pro Glu Tyr Gly Gln Gly Ile Asn Pro Ile Ser Arg Leu Ala
                200                 205                 210
```

-continued

| | | |
|---|---|---|
| cag atc cag cag gca aaa aag gag aag gag cca gag tac acg ctc ctc<br>Gln Ile Gln Gln Ala Lys Lys Glu Lys Glu Pro Glu Tyr Thr Leu Leu<br>        215                   220                225 | 968 | aca gag cga ggc ctc ccg cgc agg gag ttt gtg atg cag gtg aag    1016
Thr Glu Arg Gly Leu Pro Arg Arg Glu Phe Val Met Gln Val Lys
            230                 235                 240 gtt gga aac cac act gca gaa gga acg ggc acc aac aag aag gtg gcc    1064
Val Gly Asn His Thr Ala Glu Gly Thr Gly Thr Asn Lys Lys Val Ala
    245                 250                 255 aag cgc aat gca gcc gag aac atg ctg gag atc ctt ggt ttc aaa gtc    1112
Lys Arg Asn Ala Ala Glu Asn Met Leu Glu Ile Leu Gly Phe Lys Val
260                 265                 270                 275 ccg cag cgg cag ccc acc aaa ccc gca ctc aag tca gag gag aag aca    1160
Pro Gln Arg Gln Pro Thr Lys Pro Ala Leu Lys Ser Glu Glu Lys Thr
                280                 285                 290 ccc ata aag aaa cca ggg gat gga aga aaa gta acc ttt ttt gaa cct    1208
Pro Ile Lys Lys Pro Gly Asp Gly Arg Lys Val Thr Phe Phe Glu Pro
            295                 300                 305 ggc tct ggg gat gaa aat ggg act agt aat aaa gag gat gag ttc agg    1256
Gly Ser Gly Asp Glu Asn Gly Thr Ser Asn Lys Glu Asp Glu Phe Arg
        310                 315                 320 atg cct tat cta agt cat cag cag ctg cct gct gga att ctt ccc atg    1304
Met Pro Tyr Leu Ser His Gln Gln Leu Pro Ala Gly Ile Leu Pro Met
    325                 330                 335 gtg ccc gag gtc gcc cag gct gta gga gtt agt caa gga cat cac acc    1352
Val Pro Glu Val Ala Gln Ala Val Gly Val Ser Gln Gly His His Thr
340                 345                 350                 355 aaa gat ttt acc agg gca gct ccg aat cct gcc aag gcc acg gta act    1400
Lys Asp Phe Thr Arg Ala Ala Pro Asn Pro Ala Lys Ala Thr Val Thr
                360                 365                 370 gcc atg ata gcc cga gag ttg ttg tat ggg ggc acc tcg ccc aca gcc    1448
Ala Met Ile Ala Arg Glu Leu Leu Tyr Gly Gly Thr Ser Pro Thr Ala
            375                 380                 385 gag acc att tta aag aat aac atc tct tca ggc cac gta ccc cat gga    1496
Glu Thr Ile Leu Lys Asn Asn Ile Ser Ser Gly His Val Pro His Gly
        390                 395                 400 cct ctc acg aga ccc tct gag caa ctg gac tat ctt tcc aga gtc cag    1544
Pro Leu Thr Arg Pro Ser Glu Gln Leu Asp Tyr Leu Ser Arg Val Gln
    405                 410                 415 gga ttc cag gtt gaa tac aaa gac ttc ccc aaa aac aac aag aac gaa    1592
Gly Phe Gln Val Glu Tyr Lys Asp Phe Pro Lys Asn Asn Lys Asn Glu
420                 425                 430                 435 ttt gta tct ctt atc aat tgc tcc tct cag cca cct ctg atc agc cat    1640
Phe Val Ser Leu Ile Asn Cys Ser Ser Gln Pro Pro Leu Ile Ser His
                440                 445                 450 ggt atc ggc aag gat gtg gag tcc tgc cat gat atg gct gcg ctg aac    1688
Gly Ile Gly Lys Asp Val Glu Ser Cys His Asp Met Ala Ala Leu Asn
            455                 460                 465 atc tta aag ttg ctg tct gag ttg gac caa caa agt aca gag atg cca    1736
Ile Leu Lys Leu Leu Ser Glu Leu Asp Gln Gln Ser Thr Glu Met Pro
        470                 475                 480 aga aca gga aac gga cca atg tct gtg tgt ggg agg tgc tgaaccttt    1785
Arg Thr Gly Asn Gly Pro Met Ser Val Cys Gly Arg Cys
    485                 490                 495 ctggccatga accattataa aatcccaaca tatatactga aaatactgaa actgctttga    1845
aaatttggaa tttctgatac ctccagtggg ccgagagaca cggtgggtaa aggatgtggg    1905
cagcagcagg gaagacaaca gaaacacaag gaggcggctg tggccggctg gactgtgctg    1965

-continued

```
gggtttgttg tgatggccac tcggtgacct ggcggtccct acgcaatagc agctgcctgt    2025
ggggaagaag ggctgcccag ccagctggtt ctcccgggac accagcagat ccacaccctg    2085
ggcacctccg tgtttggtct ttttttttccc ctgtgtgaaa aagaaacgg cacgacccct    2145 tctcaagctg gctcactcag acacattggg acaaaccctg acagccatg ccagagagag    2205 gcctttgacc ggccccagag ctaaaagcac cagagaaaat caaatgcttc ctactcagcg    2265
tgacccaact tttctagtgt gccacggccc caccacctcc tgcagtaccc acaccatcac    2325
cactgctttc tcttccaaca gtgatctgta ttcttagttt cattattttc ttttgattga    2385 tatgcacacta tataaaattt tcatttgaga atttctcaat tgtatctagt taaatagcac    2445
agtttggaaa cttgtctgag actgacttta tcaataatct aaccgacaaa gatcatatcc    2505
atgtgtatgt ggttagacat tttttatttca ttgactaacc caggacagtt tcagtgatgc    2565
aaattgtgtg ccctctggtt cagctgaaac agtcctggac tttcaaaaac cttgaataag    2625
tctcccacag ttgtataaat tggacaattt aggaatttta aactttagat gatcatttgg    2685 ttccatttttt atttcatttt tattttttgtt aatgcaaaca ggacttaaat gaactttgat    2745
ctctgtttta aagattatta aaaaacattg tgtatctata catatggctc ttgaggactt    2805
agctttcact acactacagg atatgatctc catgtagtcc atataaacct gcagagtgat    2865
tttccagagt gctcgatact gttaattaca tctccattag ggctgaaaag aatgacctac    2925
gtttctgtat acagctgtgt tgcttttgat gttgtgttac tgtacacaga agtgtgtgca    2985
ctgaggctct gcgtgtggtc cgtatggaaa acctggtagc cctgcgagtt aagtactgct    3045
tccattcatt gtttacgctg gaattttttct ccccatgaaa tgtaagtaaa acttaagtgt    3105
ttgtcatcaa taaatggtaa tactaaaaaa aaaaaaa                             3142
```

<210> SEQ ID NO 6
<211> LENGTH: 3348
<212> TYPE: DNA
<213> ORGANISM: Homo sapiens
<220> FEATURE:
<221> NAME/KEY: CDS
<222> LOCATION: (494)..(1981)
<223> OTHER INFORMATION:

<400> SEQUENCE: 6

```
acttcctgcc gggctgcggg cgcctgagcg ctcttcagcg tttgcgcggc ggctgcgcgt      60
ctctctcggc tcccgcttcc tttgaccgcc tcccccccccc ggcccggcgg cgcccgcctc     120
ctccacggcc actccgcctc ttccctccct tcgtcccttc ttcctctccc tttttttcctt    180 cttccttccc ctcctcgccg ccaccgccca ggaccgccgg ccgggggacg agtccggagc     240
agcagccagc agcagccagg tggagttttg ctcttgtcgc ccaggctgga gtgcagtggc     300
gtgatctcgg ctcactgcaa cctccacctc ccaggtcagc gattttccca cttcagcctc     360
ccgataagct gagattacag agtttattaa ccacttaacc tctcagaact gaacaaagac     420
aacattgttc ctggaacgcc ctcttttttaa aaaagaaagc ataaccccta ctgtagaact     480
aaatgcactg tgc atg aaa ctt gga aaa aaa cca atg tat aag cct gtt        529
               Met Lys Leu Gly Lys Lys Pro Met Tyr Lys Pro Val
                 1               5                  10 gac cct tac tct cgg atg cag tcc acc tat aac tac aac atg aga gga       577
Asp Pro Tyr Ser Arg Met Gln Ser Thr Tyr Asn Tyr Asn Met Arg Gly
           15                  20                  25 ggt gct tat ccc ccg agg tac ttt tac cca ttt cca gtt cca cct tta       625
Gly Ala Tyr Pro Pro Arg Tyr Phe Tyr Pro Phe Pro Val Pro Pro Leu
       30                  35                  40
```

|     |     |
| --- | --- |
| ctt tat caa gtg gaa ctt tct gtg gga gga cag caa ttt aat ggc aaa<br>Leu Tyr Gln Val Glu Leu Ser Val Gly Gly Gln Gln Phe Asn Gly Lys<br>45                        50                   55                    60 | 673 |
| gga aag aca aga cag gct gcg aaa cac gat gct gct gcc aaa gcg ttg<br>Gly Lys Thr Arg Gln Ala Ala Lys His Asp Ala Ala Ala Lys Ala Leu<br>                    65                   70                    75 | 721 |
| agg atc ctg cag aat gag ccc ctg cca gag agg ctg gag gta aat gga<br>Arg Ile Leu Gln Asn Glu Pro Leu Pro Glu Arg Leu Glu Val Asn Gly<br>                80                   85                   90 | 769 |
| aga gaa tcc gaa gaa gaa aat ctc aat aaa tct gaa ata agt caa gtg<br>Arg Glu Ser Glu Glu Glu Asn Leu Asn Lys Ser Glu Ile Ser Gln Val<br>        95                   100                 105 | 817 |
| ttt gag att gca ctt aaa cgg aac ttg cct gtg aat ttc gag gtg gcc<br>Phe Glu Ile Ala Leu Lys Arg Asn Leu Pro Val Asn Phe Glu Val Ala<br>110                     115                 120 | 865 |
| cgg gag agt ggc cca ccc cac atg aag aac ttt gtg acc aag gtt tcg<br>Arg Glu Ser Gly Pro Pro His Met Lys Asn Phe Val Thr Lys Val Ser<br>125                     130                 135                 140 | 913 |
| gtt ggg gag ttt gtg ggg gaa ggt gaa ggg aaa agc aag aag att tca<br>Val Gly Glu Phe Val Gly Glu Gly Glu Gly Lys Ser Lys Lys Ile Ser<br>                       145                 150                 155 | 961 |
| aag aaa aat gcc gcc ata gct gtt ctt gag gag ctg aag aag tta ccg<br>Lys Lys Asn Ala Ala Ile Ala Val Leu Glu Glu Leu Lys Lys Leu Pro<br>160                     165                 170 | 1009 |
| ccc ctg cct gca gtt gaa cga gta aag cct aga atc aaa aag aaa aca<br>Pro Leu Pro Ala Val Glu Arg Val Lys Pro Arg Ile Lys Lys Lys Thr<br>                175                 180                 185 | 1057 |
| aaa ccc ata gtc aag cca cag aca agc cca gaa tat ggc cag ggg atc<br>Lys Pro Ile Val Lys Pro Gln Thr Ser Pro Glu Tyr Gly Gln Gly Ile<br>190                     195                 200 | 1105 |
| aat ccg att agc cga ctg gcc cag atc cag cag gca aaa aag gag aag<br>Asn Pro Ile Ser Arg Leu Ala Gln Ile Gln Gln Ala Lys Lys Glu Lys<br>205                     210                 215                 220 | 1153 |
| gag cca gag tac acg ctc ctc aca gag cga ggc ctc ccg cgc cgc agg<br>Glu Pro Glu Tyr Thr Leu Leu Thr Glu Arg Gly Leu Pro Arg Arg Arg<br>                       225                 230                 235 | 1201 |
| gag ttt gtg atg cag gtg aag gtt gga aac cac act gca gaa gga acg<br>Glu Phe Val Met Gln Val Lys Val Gly Asn His Thr Ala Glu Gly Thr<br>240                     245                 250 | 1249 |
| ggc acc aac aag aag gtg gcc aag cgc aat gca gcc gag aac atg ctg<br>Gly Thr Asn Lys Lys Val Ala Lys Arg Asn Ala Ala Glu Asn Met Leu<br>255                     260                 265 | 1297 |
| gag atc ctt ggt ttc aaa gtc ccg cag cgg cag ccc acc aaa ccc gca<br>Glu Ile Leu Gly Phe Lys Val Pro Gln Arg Gln Pro Thr Lys Pro Ala<br>270                     275                 280 | 1345 |
| ctc aag tca gag gag aag aca ccc ata aag aaa cca ggg gat gga aga<br>Leu Lys Ser Glu Glu Lys Thr Pro Ile Lys Lys Pro Gly Asp Gly Arg<br>285                     290                 295                 300 | 1393 |
| aaa gta acc ttt ttt gaa cct ggc tct ggg gat gaa aat ggg act agt<br>Lys Val Thr Phe Phe Glu Pro Gly Ser Gly Asp Glu Asn Gly Thr Ser<br>                       305                 310                 315 | 1441 |
| aat aaa gag gat gag ttc agg atg cct tat cta agt cat cag cag ctg<br>Asn Lys Glu Asp Glu Phe Arg Met Pro Tyr Leu Ser His Gln Gln Leu<br>320                     325                 330 | 1489 |
| cct gct gga att ctt ccc atg gtg ccc gag gtc gcc cag gct gta gga<br>Pro Ala Gly Ile Leu Pro Met Val Pro Glu Val Ala Gln Ala Val Gly<br>335                     340                 345 | 1537 |
| gtt agt caa gga cat cac acc aaa gat ttt acc agg gca gct ccg aat<br>Val Ser Gln Gly His His Thr Lys Asp Phe Thr Arg Ala Ala Pro Asn | 1585 |

```
                                                  -continued 350                 355                 360
cct gcc aag gcc acg gta act gcc atg ata gcc cga gag ttg ttg tat      1633
Pro Ala Lys Ala Thr Val Thr Ala Met Ile Ala Arg Glu Leu Leu Tyr
365                 370                 375                 380 ggg ggc acc tcg ccc aca gcc gag acc att tta aag aat aac atc tct      1681
Gly Gly Thr Ser Pro Thr Ala Glu Thr Ile Leu Lys Asn Asn Ile Ser
                385                 390                 395 tca ggc cac gta ccc cat gga cct ctc acg aga ccc tct gag caa ctg      1729
Ser Gly His Val Pro His Gly Pro Leu Thr Arg Pro Ser Glu Gln Leu
            400                 405                 410 gac tat ctt tcc aga gtc cag gga ttc cag gtt gaa tac aaa gac ttc      1777
Asp Tyr Leu Ser Arg Val Gln Gly Phe Gln Val Glu Tyr Lys Asp Phe
        415                 420                 425 ccc aaa aac aac aag aac gaa ttt gta tct ctt atc aat tgc tcc tct      1825
Pro Lys Asn Asn Lys Asn Glu Phe Val Ser Leu Ile Asn Cys Ser Ser
    430                 435                 440 cag cca cct ctg atc agc cat ggt atc ggc aag gat gtg gag tcc tgc      1873
Gln Pro Pro Leu Ile Ser His Gly Ile Gly Lys Asp Val Glu Ser Cys
445                 450                 455                 460 cat gat atg gct gcg ctg aac atc tta aag ttg ctg tct gag ttg gac      1921
His Asp Met Ala Ala Leu Asn Ile Leu Lys Leu Leu Ser Glu Leu Asp
                465                 470                 475 caa caa agt aca gag atg cca aga aca gga aac gga cca atg tct gtg      1969
Gln Gln Ser Thr Glu Met Pro Arg Thr Gly Asn Gly Pro Met Ser Val
            480                 485                 490 tgt ggg agg tgc tgaacctttt ctggccatga accattataa atcccaaca           2021
Cys Gly Arg Cys
        495 tatatactga aaatactgaa actgctttga aaatttggaa tttctgatac ctccagtggg    2081 ccgagagaca cggtgggtaa aggatgtggg cagcagcagg gaagacaaca gaaacacaag    2141 gaggcggctg tggccggctg gactgtgctg gggtttgttg tgatggccac tcggtgacct    2201 ggcggtccct acgcaatagc agctgcctgt ggggaagaag ggctgcccag ccagctggtt    2261 ctcccgggac accagcagat ccacaccctg gcacctccg tgtttggtct ttttttttccc    2321 ctgtgtgaaa gaagaaacgg cacgacccct tctcaagctg gctcactcag acacattggg    2381 acaaaccctg gacagccatg ccagagagag gcctttgacc ggccccagag ctaaaagcac    2441 cagagaaaat caaatgcttc ctactcagcg tgacccaact tttctagtgt gccacggccc    2501 caccacctcc tgcagtaccc acaccatcac cactgctttc tcttccaaca gtgatctgta    2561 ttcttagttt cattatttc ttttgattga tatgacacta tataaattt tcatttgaga      2621 atttctcaat tgtatctagt aaatagcac agttttggaaa cttgtctgag actgacttta   2681 tcaataatct aaccgacaaa gatcatatcc atgtgtatgt ggttagacat ttttatttca    2741 ttgactaacc caggacagtt tcagtgatgc aaattgtgtg ccctctggtt cagctgaaac    2801 agtcctggac tttcaaaaac cttgaataag tctcccacag ttgtataaat tggacaattt    2861 aggaattttta aactttagat gatcatttgg ttccattttt atttcattt tattttttgtt  2921 aatgcaaaca ggacttaaat gaactttgat ctctgtttta aagattatta aaaaacattg    2981 tgtatctata catatggctc ttgaggactt agctttcact acactacagg atatgatctc    3041 catgtagtcc atataaacct gcagagtgat tttccagagt gctcgatact gttaattaca    3101 tctccattag ggctgaaaag aatgacctac gtttctgtat acagctgtgt tgcttttgat    3161 gttgtgttac tgtacacaga agtgtgtgca ctgaggctct gcgtgtggtc cgtatgaaa    3221 acctggtagc cctgcgagtt aagtactgct tccattcatt gtttacgctg gaatttttct   3281
```

-continued

```
ccccatggaa tgtaagtaaa acttaagtgt ttgtcatcaa taaatggtaa tactaaaaaa      3341
aaaaaaa                                                                3348

<210> SEQ ID NO 7
<211> LENGTH: 2857
<212> TYPE: DNA
<213> ORGANISM: Mus musculus
<220> FEATURE:
<221> NAME/KEY: CDS
<222> LOCATION: (324)..(1784)
<223> OTHER INFORMATION:

<400> SEQUENCE: 7
cgggcgcggc ccctcccccg tcacttcctg ccaggctgcg ggccccgagc cgctcttcag        60
cgtttgcgct ggctgtcgtc gcgtctgtgt gcgctccccc ttcttctgag ccccggcctg       120
gcggcgcccg ccttcgcctc cgccactccg cctcttccct cctctggtcg gcccttttt       180 cctcgccgtc ttcacttgct tcttcacctc ctcgccgccg cccaagaccg ccggccccgg       240
gacgagctct ggggaagcag ccagaaagta tagcttctac cattgagctc aatgcactgt       300
gtgtgaaact ggaagaaaa cca atg tat aag ccc gtg gac cct cac tct cgg       353
                          Met Tyr Lys Pro Val Asp Pro His Ser Arg
                           1               5                  10 atg cag tcc acc tac agc tat ggc atg cgt gga ggt gcc tat ccc ccc        401
Met Gln Ser Thr Tyr Ser Tyr Gly Met Arg Gly Gly Ala Tyr Pro Pro
             15                  20                  25 aga tac ttt tac cca ttt cca gtc cca cct tta ctc tac caa gtt gag        449
Arg Tyr Phe Tyr Pro Phe Pro Val Pro Pro Leu Leu Tyr Gln Val Glu
         30                  35                  40 ctc tcc gtg ggc gga cag cag ttt aat ggg aaa gga aag atg aga cca        497
Leu Ser Val Gly Gly Gln Gln Phe Asn Gly Lys Gly Lys Met Arg Pro
     45                  50                  55 ccc gtg aaa cac gat gcc cct gcc cgt gcg ctg agg act ctg cag agt        545
Pro Val Lys His Asp Ala Pro Ala Arg Ala Leu Arg Thr Leu Gln Ser
 60                  65                  70 gaa ccc ctg cca gaa agg ttg gag gta aat gga aga gaa gca gag gaa        593
Glu Pro Leu Pro Glu Arg Leu Glu Val Asn Gly Arg Glu Ala Glu Glu
 75                  80                  85                  90 gaa aac ctc aat aaa tcg gaa ata agc caa gtg ttt gaa att gcg ctg        641
Glu Asn Leu Asn Lys Ser Glu Ile Ser Gln Val Phe Glu Ile Ala Leu
                 95                 100                 105 aag cgg aat ttg cct gtg aat ttt gag gtg gcc cgg gag agt ggc cca        689
Lys Arg Asn Leu Pro Val Asn Phe Glu Val Ala Arg Glu Ser Gly Pro
             110                 115                 120 cca cac atg aag aac ttt gtg acc agg gtt tca gtt ggg gaa ttt gta        737
Pro His Met Lys Asn Phe Val Thr Arg Val Ser Val Gly Glu Phe Val
         125                 130                 135 ggg gaa gga gaa ggg aaa agc aag aag atc tcc aag aag aat gcg gcc        785
Gly Glu Gly Glu Gly Lys Ser Lys Lys Ile Ser Lys Lys Asn Ala Ala
     140                 145                 150 agg gct gtt ctg gag cag ctt agg agg ctg cca ccc ctc cct gct gtg        833
Arg Ala Val Leu Glu Gln Leu Arg Arg Leu Pro Pro Leu Pro Ala Val
155                 160                 165                 170 gag cga gtg aag ccc aga atc aag aag aaa agt cag ccc acc tgc aag        881
Glu Arg Val Lys Pro Arg Ile Lys Lys Lys Ser Gln Pro Thr Cys Lys
                 175                 180                 185 aca gcc ccg gat tat ggc caa ggg atg aat cct att agt aga ctt gca        929
Thr Ala Pro Asp Tyr Gly Gln Gly Met Asn Pro Ile Ser Arg Leu Ala
             190                 195                 200
```

-continued

| | | | | | | | | | | | | | | | |
|---|---|---|---|---|---|---|---|---|---|---|---|---|---|---|---|
| cag | atc | cag | cag | gca | aaa | aag | gag | aag | gag | cca | gag | tac | atg | ctc | ctt | 977 |
| Gln | Ile | Gln | Gln | Ala | Lys | Lys | Glu | Lys | Glu | Pro | Glu | Tyr | Met | Leu | Leu | |
| | 205 | | | | | 210 | | | | | 215 | | | | | |

```
cag atc cag cag gca aaa aag gag aag gag cca gag tac atg ctc ctt    977
Gln Ile Gln Gln Ala Lys Lys Glu Lys Glu Pro Glu Tyr Met Leu Leu
    205                 210                 215 aca gaa cga ggt ctt cca cgt cgc agg gag ttt gtg atg cag gta aag    1025
Thr Glu Arg Gly Leu Pro Arg Arg Arg Glu Phe Val Met Gln Val Lys
220                 225                 230 gtt ggg cat cac act gca gaa gga gtg ggt acc aat aag aag gtg gcc    1073
Val Gly His His Thr Ala Glu Gly Val Gly Thr Asn Lys Lys Val Ala
235                 240                 245                 250 aag cgt aat gct gct gag aac atg ctg gag atc ctg ggg ttc aaa gtt    1121
Lys Arg Asn Ala Ala Glu Asn Met Leu Glu Ile Leu Gly Phe Lys Val
                255                 260                 265 ccc cag gcg cag cct gcc aag cca gca ctc aaa tca gaa gag aag act    1169
Pro Gln Ala Gln Pro Ala Lys Pro Ala Leu Lys Ser Glu Glu Lys Thr
        270                 275                 280 cca gta aag aaa cca gga gac gga agg aaa gta acg ttt ttt gaa cct    1217
Pro Val Lys Lys Pro Gly Asp Gly Arg Lys Val Thr Phe Phe Glu Pro
            285                 290                 295 agc cct ggg gat gaa aat gga act agt aac aag gac gag gag ttc agg    1265
Ser Pro Gly Asp Glu Asn Gly Thr Ser Asn Lys Asp Glu Glu Phe Arg
300                 305                 310 atg cct tat ctt agc cat cag cag ctg cca gct gga att ctc ccc atg    1313
Met Pro Tyr Leu Ser His Gln Gln Leu Pro Ala Gly Ile Leu Pro Met
315                 320                 325                 330 gtg ccg gaa gtt gcc cag gct gtc ggg gtt agt caa gga cac cac acc    1361
Val Pro Glu Val Ala Gln Ala Val Gly Val Ser Gln Gly His His Thr
                335                 340                 345 aaa gat ttc acc agg gca gct cca aat cct gcc aag gca acg gta act    1409
Lys Asp Phe Thr Arg Ala Ala Pro Asn Pro Ala Lys Ala Thr Val Thr
        350                 355                 360 gcc atg ata gcc cga gag ttg ttg tac ggg ggc acc tcg ccc aca gcc    1457
Ala Met Ile Ala Arg Glu Leu Leu Tyr Gly Gly Thr Ser Pro Thr Ala
            365                 370                 375 gag acc att tta aag agt aac atc tct tca ggc cac gta ccc cat gga    1505
Glu Thr Ile Leu Lys Ser Asn Ile Ser Ser Gly His Val Pro His Gly
380                 385                 390 cct cgc act aga ccc tct gag caa ctg tac tac ctt tcc aga gcc cag    1553
Pro Arg Thr Arg Pro Ser Glu Gln Leu Tyr Tyr Leu Ser Arg Ala Gln
395                 400                 405                 410 gga ttc cag gtt gaa tac aaa gat ttt ccc aag aac aac aag aac gag    1601
Gly Phe Gln Val Glu Tyr Lys Asp Phe Pro Lys Asn Asn Lys Asn Glu
                415                 420                 425 tgt gta tct ctc atc aac tgc tcc tca cag ccg cct ctc gtc agt cat    1649
Cys Val Ser Leu Ile Asn Cys Ser Ser Gln Pro Pro Leu Val Ser His
        430                 435                 440 ggc atc ggc aag gat gtg gag tcc tgt cat gat atg gct gca ctg aac    1697
Gly Ile Gly Lys Asp Val Glu Ser Cys His Asp Met Ala Ala Leu Asn
            445                 450                 455 att tta aag ctg ctg tct gag ttg gac caa cag agc aca gag atg cca    1745
Ile Leu Lys Leu Leu Ser Glu Leu Asp Gln Gln Ser Thr Glu Met Pro
460                 465                 470 aga aca gga aat gga cca gtt tca gcg tgc ggg agg tgc tgaacctttt    1794
Arg Thr Gly Asn Gly Pro Val Ser Ala Cys Gly Arg Cys
475                 480                 485 ctggccacaa accattataa aacccaacat atatactgaa aatactgaga actgctttga    1854
aaatttggaa tatctgataa ctccagtggg ccaagacatg gtggataaaa atgtggcaaa    1914
gacgacaaga aacttcaggt ggtagccctg gttgtgctgg cggctagtga tgatgctgtg    1974
ctctgccatc catccagaca gaaaccagcc ccaacgcctc cagttctgtt tttgcatcgt    2034
```

```
gacaaagaga gcacagccaa ttctcatgct ggcttcttca gatactttga aaaacccgga   2094
cagccacacc agagaggcct tatagcggcc ccggagctaa acggaccaga gaaaaggcca   2154
gtgcttccta ctgcacatga ctgactcagc tccgccacac gtagcaccac tgtaaccact   2214
gctttctctt cagtttcatt ttttccttt gattgataca acactataat tttcatttca    2274
gttccttagt cgtgtctact tacctagcag tttagaaact gtcagtcatg taactggcaa   2334
ggatcacagc ccggttgggt ggcattctgt gcctctggct tggctgaaca gttctggaat   2394
taccaccaga atccttgact ccctgcccct tgtataaatt ggacagctta ggacttttaa   2454
actttagatc aaaagatatg gtccttttta actttatttt taaggagcag actttaaaat   2514
gagccctgac ctttacccat tataacagaa tttgtcaaaa ggagtgtttc ttgaggaggt   2574 agctttttt taccacacta caggacatta cctgtaggcc cagaagacta caggctggtg    2634
tccctagagg gcccaataca gtcaattcca acctctaagt cggggaaagg tgacaggttt   2694
cctggtgctg gtgtgcacag ggcaggcag gtcagctggc ctggggaaga gcattgtggc    2754
tcctagtgca gccctgcttc cactcttggt ttagctggaa ccttcccact catggaatat   2814
aagtaaactc actttctttg tcaccaataa atggtaatac taa                     2857
```

<210> SEQ ID NO 8
<211> LENGTH: 487
<212> TYPE: PRT
<213> ORGANISM: Mus musculus

<400> SEQUENCE: 8

```
Met Tyr Lys Pro Val Asp Pro His Ser Arg Met Gln Ser Thr Tyr Ser
  1               5                  10                  15

Tyr Gly Met Arg Gly Ala Tyr Pro Pro Arg Tyr Phe Tyr Pro Phe
             20                  25                  30

Pro Val Pro Leu Leu Tyr Gln Val Glu Leu Ser Val Gly Gly Gln
         35                  40                  45

Gln Phe Asn Gly Lys Gly Lys Met Arg Pro Val Lys His Asp Ala
     50                  55                  60

Pro Ala Arg Ala Leu Arg Thr Leu Gln Ser Glu Pro Leu Pro Glu Arg
 65                  70                  75                  80

Leu Glu Val Asn Gly Arg Glu Ala Glu Glu Asn Leu Asn Lys Ser
                 85                  90                  95

Glu Ile Ser Gln Val Phe Glu Ile Ala Leu Lys Arg Asn Leu Pro Val
            100                 105                 110

Asn Phe Glu Val Ala Arg Glu Ser Gly Pro Pro His Met Lys Asn Phe
        115                 120                 125

Val Thr Arg Val Ser Val Gly Glu Phe Val Gly Glu Gly Glu Gly Lys
    130                 135                 140

Ser Lys Lys Ile Ser Lys Lys Asn Ala Ala Arg Ala Val Leu Glu Gln
145                 150                 155                 160

Leu Arg Arg Leu Pro Pro Leu Pro Ala Val Glu Arg Val Lys Pro Arg
                165                 170                 175

Ile Lys Lys Lys Ser Gln Pro Thr Cys Lys Thr Ala Pro Asp Tyr Gly
            180                 185                 190

Gln Gly Met Asn Pro Ile Ser Arg Leu Ala Gln Ile Gln Gln Ala Lys
        195                 200                 205

Lys Glu Lys Glu Pro Glu Tyr Met Leu Leu Thr Glu Arg Gly Leu Pro
    210                 215                 220
```

-continued

```
Arg Arg Arg Glu Phe Val Met Gln Val Lys Val Gly His His Thr Ala
225                 230                 235                 240

Glu Gly Val Gly Thr Asn Lys Lys Val Ala Lys Arg Asn Ala Ala Glu
            245                 250                 255

Asn Met Leu Glu Ile Leu Gly Phe Lys Val Pro Gln Ala Gln Pro Ala
            260                 265                 270

Lys Pro Ala Leu Lys Ser Glu Glu Lys Thr Pro Val Lys Lys Pro Gly
            275                 280                 285

Asp Gly Arg Lys Val Thr Phe Phe Glu Pro Ser Pro Gly Asp Glu Asn
            290                 295                 300

Gly Thr Ser Asn Lys Asp Glu Glu Phe Arg Met Pro Tyr Leu Ser His
305                 310                 315                 320

Gln Gln Leu Pro Ala Gly Ile Leu Pro Met Val Pro Glu Val Ala Gln
            325                 330                 335

Ala Val Gly Val Ser Gln Gly His His Thr Lys Asp Phe Thr Arg Ala
            340                 345                 350

Ala Pro Asn Pro Ala Lys Ala Thr Val Thr Ala Met Ile Ala Arg Glu
            355                 360                 365

Leu Leu Tyr Gly Gly Thr Ser Pro Thr Ala Glu Thr Ile Leu Lys Ser
370                 375                 380

Asn Ile Ser Ser Gly His Val Pro His Gly Pro Arg Thr Arg Pro Ser
385                 390                 395                 400

Glu Gln Leu Tyr Tyr Leu Ser Arg Ala Gln Gly Phe Gln Val Glu Tyr
            405                 410                 415

Lys Asp Phe Pro Lys Asn Asn Lys Asn Glu Cys Val Ser Leu Ile Asn
            420                 425                 430

Cys Ser Ser Gln Pro Pro Leu Val Ser His Gly Ile Gly Lys Asp Val
            435                 440                 445

Glu Ser Cys His Asp Met Ala Ala Leu Asn Ile Leu Lys Leu Leu Ser
            450                 455                 460

Glu Leu Asp Gln Gln Ser Thr Glu Met Pro Arg Thr Gly Asn Gly Pro
465                 470                 475                 480

Val Ser Ala Cys Gly Arg Cys
            485

<210> SEQ ID NO 9
<211> LENGTH: 1026
<212> TYPE: PRT
<213> ORGANISM: Drosophila melanogaster

<400> SEQUENCE: 9

Met Gln His Asn Val His Ala Ala Arg Pro Ala Pro His Ile Arg Ala
1               5                   10                  15

Ala His His His Ser His Ser His Ala His Met His Leu His Pro Gly
            20                  25                  30

Met Glu Gln His Leu Gly Pro Ser Leu Gln Gln Gln Gln Gln Pro Pro
        35                  40                  45

Pro Pro Pro Gln Gln Pro Pro His Arg Asp Leu His Ala Arg Leu Asn
    50                  55                  60

His His His Leu His Ala Gln Gln Gln Gln Gln Gln Gln Thr Ser Ser
65                  70                  75                  80

Asn Gln Ala Ala Ala Val Ala Ala Ala Gly Ala Ala Tyr His His Gly
            85                  90                  95

Asn Ile Asn Ser Asn Ser Gly Ser Asn Ile Ser Ser Asn Ser Asn Gln
            100                 105                 110
```

-continued

```
Met Gln Lys Ile Arg Gln Gln His Gln His Leu Ser Ser Ser Asn Gly
            115                 120                 125
Leu Leu Gly Asn Gln Pro Pro Gly Pro Pro Gln Ala Phe Asn Pro
    130                 135                 140
Leu Ala Gly Asn Pro Ala Ala Leu Ala Tyr Asn Gln Leu Pro Pro His
145                 150                 155                 160
Pro Pro His His Met Ala Ala His Leu Gly Ser Tyr Ala Ala Pro Pro
                165                 170                 175
Pro His Tyr Tyr Met Ser Gln Ala Lys Pro Ala Lys Tyr Asn His Tyr
            180                 185                 190
Gly Ser Asn Ala Asn Ser Asn Ser Gly Ser Asn Asn Ser Asn Ser Asn
            195                 200                 205
Tyr Ala Pro Lys Ala Ile Leu Gln Asn Thr Tyr Arg Asn Gln Lys Val
    210                 215                 220
Val Val Pro Pro Val Val Gln Glu Val Thr Pro Val Pro Glu Pro Pro
225                 230                 235                 240
Val Thr Thr Asn Asn Ala Thr Thr Asn Ser Thr Ser Asn Ser Thr Val
                245                 250                 255
Ile Ala Ser Glu Pro Val Thr Gln Glu Asp Thr Ser Gln Lys Pro Glu
            260                 265                 270
Thr Arg Gln Glu Pro Ala Ser Ala Asp Asp His Val Ser Thr Gly Asn
    275                 280                 285
Ile Asp Ala Thr Gly Ala Leu Ser Asn Glu Asp Thr Ser Ser Ser Gly
    290                 295                 300
Arg Gly Gly Lys Asp Lys Thr Pro Met Cys Leu Val Asn Glu Leu Ala
305                 310                 315                 320
Arg Tyr Asn Lys Ile Thr His Gln Tyr Arg Leu Thr Glu Glu Arg Gly
                325                 330                 335
Pro Ala His Cys Lys Thr Phe Thr Val Thr Leu Met Leu Gly Asp Glu
            340                 345                 350
Glu Tyr Ser Ala Asp Gly Phe Lys Ile Lys Lys Ala Gln His Leu Ala
    355                 360                 365
Ala Ser Lys Ala Ile Glu Glu Thr Met Tyr Lys His Pro Pro Pro Lys
370                 375                 380
Ile Arg Arg Ser Glu Glu Gly Gly Pro Met Arg Thr His Ile Thr Pro
385                 390                 395                 400
Thr Val Glu Leu Asn Ala Leu Ala Met Lys Leu Gly Gln Arg Thr Phe
                405                 410                 415
Tyr Leu Leu Asp Pro Thr Gln Ile Pro Pro Thr Asp Ser Ile Val Pro
            420                 425                 430
Pro Glu Phe Ala Gly Gly His Leu Leu Thr Ala Pro Gly Pro Gly Met
    435                 440                 445
Pro Gln Pro Pro Pro Pro Ala Tyr Ala Leu Arg Gln Arg Leu Gly
    450                 455                 460
Asn Gly Phe Val Pro Ile Pro Ser Gln Pro Met His Pro His Phe Phe
465                 470                 475                 480
His Gly Pro Gly Gln Arg Pro Phe Pro Lys Phe Pro Ser Arg Phe
                485                 490                 495
Ala Leu Pro Pro Pro Leu Gly Ala His Val His Gly Pro Asn Gly
            500                 505                 510
Pro Phe Pro Ser Val Pro Thr Pro Pro Ser Lys Ile Thr Leu Phe Val
            515                 520                 525
```

-continued

```
Gly Lys Gln Lys Phe Val Gly Ile Gly Arg Thr Leu Gln Gln Ala Lys
    530             535             540
His Asp Ala Ala Ala Arg Ala Leu Gln Val Leu Lys Thr Gln Ala Ile
545                 550             555                 560
Ser Ala Ser Glu Glu Ala Leu Glu Asp Ser Met Asp Glu Gly Asp Lys
                565             570             575
Lys Ser Pro Ile Ser Gln Val His Glu Ile Gly Ile Lys Arg Asn Met
            580             585             590
Thr Val His Phe Lys Val Leu Arg Glu Glu Pro Ala His Met Lys
        595             600             605
Asn Phe Ile Thr Ala Cys Ile Val Gly Ser Ile Val Thr Glu Gly Glu
610             615             620
Gly Asn Gly Lys Lys Val Ser Lys Arg Ala Ala Glu Lys Met Leu
625             630             635             640
Val Glu Leu Gln Lys Leu Pro Pro Leu Thr Pro Thr Lys Gln Thr Pro
                645             650             655
Leu Lys Arg Ile Lys Val Lys Thr Pro Gly Lys Ser Gly Ala Ala Ala
                660             665             670
Arg Glu Gly Ser Val Val Ser Gly Thr Asp Gly Thr Met Gln Thr Gly
            675             680             685
Lys Pro Glu Arg Arg Lys Arg Leu Asn Pro Pro Lys Asp Lys Leu Ile
    690             695             700
Asp Met Asp Asp Ala Asp Asn Pro Ile Thr Lys Leu Ile Gln Leu Gln
705             710             715             720
Gln Thr Arg Lys Glu Lys Glu Pro Ile Phe Glu Leu Ile Ala Lys Asn
                725             730             735
Gly Asn Glu Thr Ala Arg Arg Glu Phe Val Met Glu Val Ser Ala
            740             745             750
Ser Gly Ser Thr Ala Arg Gly Thr Gly Asn Ser Lys Lys Leu Ala Lys
        755             760             765
Arg Asn Ala Ala Gln Ala Leu Phe Glu Leu Leu Glu Ala Val Gln Val
    770             775             780
Thr Pro Thr Asn Glu Thr Gln Ser Ser Glu Glu Cys Cys Thr Ser Ala
785                 790             795                 800
Thr Met Ser Ala Val Thr Ala Pro Ala Val Glu Ala Thr Ala Glu Gly
                805             810             815
Lys Val Pro Met Val Ala Thr Pro Val Gly Pro Met Pro Gly Ile Leu
            820             825             830
Ile Leu Arg Gln Asn Lys Lys Pro Ala Lys Lys Arg Asp Gln Ile Val
        835             840             845
Ile Val Lys Ser Asn Val Glu Ser Lys Glu Glu Ala Asn Lys Glu
    850             855             860
Val Ala Val Ala Ala Glu Glu Asn Ser Asn Asn Ser Ala Asn Ser Gly
865                 870             875                 880
Asp Ser Ser Asn Ser Ser Ser Gly Asp Ser Gln Ala Thr Glu Ala Ala
                885             890             895
Ser Glu Ser Ala Leu Asn Thr Ser Gly Ser Asn Thr Ser Gly Val
                900             905             910
Ser Ser Asn Ser Ser Asn Val Gly Ala Asn Thr Asp Gly Asn His
            915             920             925
Ala Glu Ser Lys Asn Asn Thr Glu Ser Ser Ser Asn Ser Thr Ser Asn
    930             935             940
Thr Gln Ser Ala Gly Val His Met Lys Glu Gln Leu Leu Tyr Leu Ser
```

-continued

```
             945                 950                 955                 960
Lys Leu Leu Asp Phe Glu Val Asn Phe Ser Asp Tyr Pro Lys Gly Asn
                 965                 970                 975

His Asn Glu Phe Leu Thr Ile Val Thr Leu Ser Thr His Pro Pro Gln
             980                 985                 990

Ile Cys His Gly Val Gly Lys Ser  Ser Glu Glu Ser Gln  Asn Asp Ala
         995                 1000                1005

Ala Ser  Asn Ala Leu Lys Ile  Leu Ser Lys Leu Gly  Leu Asn Asn
    1010             1015                1020

Ala Met  Lys
    1025
```

<210> SEQ ID NO 10
<211> LENGTH: 705
<212> TYPE: PRT
<213> ORGANISM: Caenorhabditis elegans

<400> SEQUENCE: 10

```
Met Gln Ala Val Phe Glu Thr Thr Leu Thr Gln Lys Met Asp Gly Val
  1               5                  10                  15

Met Ile Val Gln Glu Thr Thr Thr Asp Leu Ala Asp Thr Leu Glu Asn
                 20                  25                  30

Ala Ser Ile Ser Ala Glu Lys Ser Glu Gln Lys Pro Glu Arg Leu His
             35                  40                  45

Pro Gln His Trp Cys Gly Gln His Lys Phe Glu Ala Asp Ser Pro Thr
         50                  55                  60

Asn Phe Tyr Asp Tyr Thr Asn Ala Lys Glu Lys Glu Lys Ser Ala Met
 65                  70                  75                  80

Cys Arg Val Ala Glu Ile Ala Arg Phe Asn Lys Leu Arg His Val Tyr
                 85                  90                  95

Asn Leu Gln Asp Glu Ser Gly Pro Ala His Lys Lys Leu Phe Thr Val
            100                 105                 110

Lys Leu Val Leu Thr Glu Ala Glu Thr Phe Glu Gly Ser Gly Thr Ser
        115                 120                 125

Ile Lys Arg Ala Gln Gln Ala Ser Ala Glu Ala Ala Leu Lys Gly Thr
    130                 135                 140

Lys Leu Pro Leu Pro Thr Glu Lys Pro Thr Lys Lys Arg Ile Asn Asp
145                 150                 155                 160

Thr Thr Lys Pro His Arg Val Leu Gln Asn Val Cys Arg Thr Leu Gln
                165                 170                 175

Tyr Gln Met Pro Asn Tyr Ile Ser Cys Asn Pro Pro Val Tyr Pro Asp
            180                 185                 190

Pro Gly Cys Pro Leu Pro Glu His Ile Leu Leu Pro Leu Glu Ser Met
        195                 200                 205

Ala Leu Tyr Ala Pro Pro Phe Pro Thr Leu Pro Ile Asp Pro Ala Arg
    210                 215                 220

Pro Gln Gly Pro Lys Leu Gln Ala Val Ile Val Asn Ile Asn Gly Lys
225                 230                 235                 240

Ser Ile Ala Thr Gly Ile Gly Glu Thr Tyr Pro Leu Ala Lys Gln Asp
                245                 250                 255

Ala Ala Ala Lys Ala Leu Ala Val Leu Ser Pro Leu Leu Arg Glu His
            260                 265                 270

Gln Asn Gly Ser Asp Asn Gly Phe Gly Lys Glu Asn Ile Pro Val His
        275                 280                 285
```

```
Lys Gln Lys Ser Val Ile Ser Asp Ile His Glu Lys Ala Tyr Gln Leu
    290                 295                 300
Lys Val Asn Val Val Phe Glu Val Leu Lys Glu Glu Gly Pro Pro His
305                 310                 315                 320
Asp Arg Gln Tyr Val Val Arg Cys Ala Phe Val Thr Ser Gly Asn Val
                325                 330                 335
Val Lys Ala Glu Ala Val Gly Lys Gly Lys Lys Lys Ser Ala Gln
                340                 345                 350
Gln Glu Ala Cys Thr Gln Leu Leu Ala Thr Val Glu His Leu Thr Pro
            355                 360                 365
Glu Asn Asn Pro Val Ala Leu Ala Thr Asn Val Cys Lys Thr Gln Lys
    370                 375                 380
Lys Leu Ala Ala Met Asn Arg Glu Pro Lys Arg Lys Thr Ile Val Lys
385                 390                 395                 400
Asp Lys Lys Met Asp Pro Leu Tyr Gly His Gln Ile Asn Pro Val Ser
                405                 410                 415
Arg Leu Ile Gln Val Thr Gln Ala Lys Ser Lys Glu His Pro Thr Phe
                420                 425                 430
Glu Leu Val Ala Glu His Gly Val Ser Lys Tyr Lys Glu Phe Ile Ile
            435                 440                 445
Gln Val Lys Tyr Gly Asp Asp Val Gln Glu Gly Lys Gly Pro Asn Lys
    450                 455                 460
Arg Leu Ala Lys Arg Ala Ala Ala Glu Ala Met Leu Glu Ser Ile Gly
465                 470                 475                 480
Phe Val Lys Pro Leu Pro Pro Gly Lys Ser Leu Leu Lys Lys Met
                485                 490                 495
Ile Asp Cys Asp Pro Ser Leu Pro Glu Ile Ser His Trp Thr Gly Pro
                500                 505                 510
Pro Pro Thr Ala Val Ser Val Ser Thr Ser Glu Pro Asp Thr Ser Glu
            515                 520                 525
Ala Ala Gln Leu Ser Pro Glu Gln Thr Asp Ile Ser Glu Lys Arg Glu
    530                 535                 540
Leu Ser Pro Asp Thr Glu Lys Arg Arg Val Thr Phe Asn Ser Gln Val
545                 550                 555                 560
His Ala Cys Pro Pro Pro Gly Asp Gln Asp Tyr Pro Asn Ser Ile Val
                565                 570                 575
Gln Ser Leu Lys Lys Asp Ala Ile Val Glu Gly Lys Ile Arg Arg Leu
            580                 585                 590
Lys Arg Ser Lys Glu Asn Arg Arg Ala Leu Thr Ala Glu Gln Ile Val
    595                 600                 605
Glu Leu Ser Glu Arg Ala Gln Ser Tyr Leu Gln Thr Lys Asn Thr Thr
    610                 615                 620
Ile Gln Ser Ser Gln Ser Ser Ala His His Leu Glu Gln Leu
625                 630                 635                 640
Ser Asp Phe Phe Lys Phe Ser Leu Gln Tyr Thr Ser Phe Pro Gln Val
                645                 650                 655
Gly Ile Asp Gln His Phe Thr Ile Val Ser Ile Gly Leu Glu Ala Pro
                660                 665                 670
Leu Val Gly His Gly Thr Gly Cys Ser Thr Thr Glu Ala Asp Glu Asn
            675                 680                 685
Ala Ala Leu Asp Ala Ile Ala Lys Leu Lys Glu Leu Ser Ala Ser Lys
    690                 695                 700
Thr
```

705

<210> SEQ ID NO 11
<211> LENGTH: 101
<212> TYPE: PRT
<213> ORGANISM: Homo sapiens

<400> SEQUENCE: 11

Gly Phe Lys Val Pro Gln Arg Gln Pro Thr Lys Pro Ala Leu Lys Ser
 1               5                  10                  15

Glu Glu Lys Thr Pro Ile Lys Lys Pro Gly Asp Gly Arg Lys Val Thr
             20                  25                  30

Phe Phe Asp Pro Gly Ser Gly Asp Glu Asn Gly Thr Ser Asn Lys Glu
         35                  40                  45

Asp Glu Phe Arg Leu Pro Tyr Leu Ser His Gln Leu Pro Ala Gly
     50                  55                  60

Ile Leu Pro Met Val Pro Glu Val Ala Gln Ala Val Gly Val Ser Gln
 65                  70                  75                  80

Gly His His Thr Lys Asp Phe Thr Arg Ala Ala Pro Asn Pro Ala Lys
                 85                  90                  95

Ala Thr Val Thr Ala
            100

<210> SEQ ID NO 12
<211> LENGTH: 98
<212> TYPE: PRT
<213> ORGANISM: Homo sapiens

<400> SEQUENCE: 12

Lys Glu Lys Thr Lys Thr Lys Lys Pro Gly Thr Lys Thr Lys Ser Ser
 1               5                  10                  15

Ser Pro Val Lys Lys Ser Asp Gly Lys Ser Lys Pro Leu Ala Ala Ser
             20                  25                  30

Pro Lys Pro Ala Gly Leu Lys Glu Ser Ser Asp Lys Val Ser Arg Val
         35                  40                  45

Ala Ser Pro Lys Lys Glu Ser Val Glu Lys Ala Ala Lys Pro Thr
     50                  55                  60

Thr Thr Pro Glu Val Lys Ala Ala Arg Gly Glu Glu Lys Asp Lys Glu
 65                  70                  75                  80

Thr Lys Asn Ala Ala Asn Ala Ser Ala Ser Lys Ser Ala Lys Thr Ala
                 85                  90                  95

Thr Ala

<210> SEQ ID NO 13
<211> LENGTH: 16
<212> TYPE: DNA
<213> ORGANISM: Artificial Sequence
<220> FEATURE:
<223> OTHER INFORMATION: oligonucleotide

<400> SEQUENCE: 13
agcttaatta gctgac                                               16

<210> SEQ ID NO 14
<211> LENGTH: 16
<212> TYPE: DNA
<213> ORGANISM: Artificial Sequence
<220> FEATURE:
<223> OTHER INFORMATION: oligonucleotide

```
<400> SEQUENCE: 14
agctgtcagc taatta                                               16

<210> SEQ ID NO 15
<211> LENGTH: 31
<212> TYPE: DNA
<213> ORGANISM: Artificial Sequence
<220> FEATURE:
<223> OTHER INFORMATION: oligonucleotide

<400> SEQUENCE: 15
cctggatccg aaagtatagc ttctaccatt g                              31

<210> SEQ ID NO 16
<211> LENGTH: 36
<212> TYPE: DNA
<213> ORGANISM: Artificial Sequence
<220> FEATURE:
<223> OTHER INFORMATION: oligonucleotide

<400> SEQUENCE: 16
tacataagct tctagatggc cagaaaaggt tcagca                         36

<210> SEQ ID NO 17
<211> LENGTH: 27
<212> TYPE: DNA
<213> ORGANISM: Artificial Sequence
<220> FEATURE:
<223> OTHER INFORMATION: oligonucleotide

<400> SEQUENCE: 17
ggatgaatcc tattagtaga cttgcac                                   27

<210> SEQ ID NO 18
<211> LENGTH: 29
<212> TYPE: DNA
<213> ORGANISM: Artificial Sequence
<220> FEATURE:
<223> OTHER INFORMATION: oligonucleotide

<400> SEQUENCE: 18
gctctagatt caaagttccc caggcgcag                                 29

<210> SEQ ID NO 19
<211> LENGTH: 29
<212> TYPE: DNA
<213> ORGANISM: Artificial Sequence
<220> FEATURE:
<223> OTHER INFORMATION: oligonucleotide

<400> SEQUENCE: 19
tttaagcttc tcagagggtc tagtgcgag                                 29

<210> SEQ ID NO 20
<211> LENGTH: 22
<212> TYPE: DNA
<213> ORGANISM: Artificial Sequence
<220> FEATURE:
<223> OTHER INFORMATION: oligonucleotide

<400> SEQUENCE: 20
caatgtataa gcccgtggac cc                                        22

<210> SEQ ID NO 21
<211> LENGTH: 36
```

```
<212> TYPE: DNA
<213> ORGANISM: Artificial Sequence
<220> FEATURE:
<223> OTHER INFORMATION: oligonucleotide

<400> SEQUENCE: 21
aaaaagcttg tgcaagtcta ctaataggat tcatcc                              36

<210> SEQ ID NO 22
<211> LENGTH: 18
<212> TYPE: DNA
<213> ORGANISM: Artificial Sequence
<220> FEATURE:
<223> OTHER INFORMATION: oligonucleotide

<400> SEQUENCE: 22
atagcccgag agttgttg                                                  18

<210> SEQ ID NO 23
<211> LENGTH: 36
<212> TYPE: DNA
<213> ORGANISM: Artificial Sequence
<220> FEATURE:
<223> OTHER INFORMATION: oligonucleotide

<400> SEQUENCE: 23
tacataagct tctagatggc cagaaaaggt tcagca                              36

<210> SEQ ID NO 24
<211> LENGTH: 29
<212> TYPE: DNA
<213> ORGANISM: Artificial Sequence
<220> FEATURE:
<223> OTHER INFORMATION: oligonucleotide

<400> SEQUENCE: 24
tacatgtcga cttcctgccr ggctgcggg                                      29

<210> SEQ ID NO 25
<211> LENGTH: 44
<212> TYPE: DNA
<213> ORGANISM: Artificial Sequence
<220> FEATURE:
<223> OTHER INFORMATION: oligonucleotide

<400> SEQUENCE: 25
tacaatctag attatcagcg gccgcacctc ccacacacag acat                     44

<210> SEQ ID NO 26
<211> LENGTH: 41
<212> TYPE: DNA
<213> ORGANISM: Artificial Sequence
<220> FEATURE:
<223> OTHER INFORMATION: oligonucleotide

<400> SEQUENCE: 26
tacataagct taagccacca tggtcaaagt tccccaggcg c                        41

<210> SEQ ID NO 27
<211> LENGTH: 40
<212> TYPE: DNA
<213> ORGANISM: Artificial Sequence
<220> FEATURE:
<223> OTHER INFORMATION: oligonucleotide
```

```
-continued
<400> SEQUENCE: 27
tacaatctag agcggccgcg ctcagagggt ctagtgcgag                                      40
```

MAMMALIAN STAUFFEN AND USE THEREOF

FIELD OF THE INVENTION

The present invention relates to mammalian staufen, a double-stranded RNA-binding protein involved in mRNA transport and localization. The invention further relates to the demonstration of the association of a RNA-binding protein with the rough endoplasmic reticulum (RER), implicating staufen and related proteins in the transport of RNA to its site of translation. Broadly, the invention therefore relates to transport and translation of RNA. More specifically, the present invention relates to human and mouse staufen proteins and to the modulation of transport of RNA to the RER by these proteins. The present invention also relates to isolated nucleic acid molecules encoding mammalian staufen, as well as vectors and host cells harboring same. In addition, the present invention relates to screening assays for identifying modulators of staufen activity and to the identification of mutants thereof which abrogate their interaction with RER. Furthermore, the present invention relates to the use of the double-stranded RNA binding activity of staufen as a means to target proteins into virions. The invention in addition relates to the incorporation of staufen into RNA viruses and the use of overexpression of staufen to significantly decrease the infectivity thereof. More particularly, the present invention relates to a novel and broad class of molecules which can be used as carriers to target molecules into virions of RNA viruses and to decrease infectivity of a wide variety of RNA viruses including retroviruses.

BACKGROUND OF THE INVENTION

It is now believed that the cytoskeleton is widely used to transport mRNAs between their transcription and processing sites in the nucleus and their translation and degradation sites in the cytoplasm (Pachter, 1992; Bassell and Singer, 1997; Nakielny et al., 1997). One consequence of the interaction between mRNAs and the cytoskeleton is to promote differential localization and/or transport of mRNAs in subcellular compartments. Indeed, examples of mRNA targeting were observed in both germinal and somatic cells throughout the animal kingdom (Wilhelm and Vale, 1993; St Johnson, 1995; Steward, 1997). The universal use of this mechanism is also apparent when we consider the nature of the proteins which are coded by the transported mRNAs; asymmetric localization involving mRNAs coding for cytosolic, secreted, membrane-associated or cytoskeletal proteins have all been reported. Localization of mRNAs in the cytoplasm is now considered an essential step in the regulation of gene expression and an efficient way to unevenly distribute proteins in polarized cells. In general, it is believed that mRNA localization is used to determine and/or regulate local sites of translation (Rings et al., 1994; St Johnston, 1995; Steward, 1997). Indeed, ribosomes and many translational cofactors were found in association with the cytoskeletal elements, preventing both mRNAs and translation factors from being diluted by the cellular fluid (Pachter, 1992). Transport and local translation of specific mRNAs has been shown to play an important role in processes such as learning and memory (Martin et al., 1997), synaptic transmission (Crino and Eberwine, 1996; Kang and Schuman, 1996; Gazzaley et al., 1997; Steward, 1997; Tongiorgi et al., 1997), axis formation during development (reviewed in St Johnston, 1995), cell motility (Kislauskis et al., 1997), and asymetric cell division (Li et al., 1997; Long et al., 1997; Takizawa et al., 1997; Broadus et al., 1998).

The mechanisms underlying mRNA localization are not yet fully understood, mainly because of the lack of information on the principal constituents of the ribonucleoprotein complexes involved in this process. Nevertheless, it is known to involve both cis-acting signals in mRNA and trans-acting RNA-binding proteins which bind to this signal (St Johnston, 1995). The signals that allow mRNAs to be recognized as a target for transport and then to be localized have been mapped within their 3'-untranslated regions (Wilhelm and Vale, 1993; St Johnston, 1995). In contrast, the nature of the RNA-binding proteins is still obscure. Recently, a 68 kDa protein which binds the β-actin mRNA zipcode localization domain was isolated and its transcript was cloned from chicken cDNA libraries (Ross et al., 1997). This protein, which binds to microfilaments, contains an RNA-binding domain which shares strong sequence similarity with the RNP1 and RNP2 motifs. In addition, 69 kDa and 78 kDa proteins in Xenopus oocyte extracts have been shown to bind to the localization signal of Vg1 mRNA (Schwartz et al., 1992; Deshler et al. 1997). While the 69 kDa protein was shown to bind microtubules (Elisha et al., 1995), the 78 kDa Vera protein co-localized with a subdomain of the smooth endoplasmic reticulum (Deshler et al., 1997). However, since these proteins have not yet been characterized, their nature and function in localization remain unclear.

Genetic and molecular studies have shown that the activity of the staufen gene product in *Drosophila* is necessary for the proper localization of bicoid and oskar mRNAs to the anterior and posterior cytoplasm of oocytes, respectively, and of prospero mRNA in neuroblasts (St Johnston et al., 1989; Ephrussi et al., 1991; Kim-Ha et al., 1991; St Johnston et al., 1991; Broadus et al., 1997; Li et al., 1997). Staufen is a member of the double-stranded RNA-binding protein family, and contains three copies of a domain consisting of a 65- to 68-amino acid consensus sequence which is required to bind RNAs having double-stranded secondary structures, and two copies of a short-domain, which retains the last 21 amino acids at the C-terminal end of the complete motif (St Johnston et al., 1991; St Johnston et al., 1992). In vitro, it has been demonstrated that staufen binds directly to bicoid and prospero mRNAs (St Johnston et al., 1992; Li et al., 1997). However, since staufen seems to bind to any dsRNA in vitro, it is not clear whether or not it binds directly to these RNAs in vivo, or needs cellular co-factors which make up part of a larger ribonucleoprotein complex to localize each mRNA. Many experiments have demonstrated that the localization of oskar, prospero and bicoid mRNAs occurs through a multistep mechanism of active transport that is dependent on elements of the cytoskeleton (Erdelyi et al., 1995; Pokrywka and Stephenson, 1995; St Johnston, 1995; Tetzlaff et al., 1996; Broadus et al., 1997).

There thus remains a need to understand the mechanisms of mRNA transport in mammals and determine the nature of both the RNAs and proteins in the RNA/protein complexes. Recently, both Southern blot analysis of human DNA and fluorescent in situ hybridization (FISH) on human chromosomes in metaphase showed that the human gene is present as a single copy in the human genome and is localized in the middle of the long arm of chromosome 20 (DesGroseillers and Lemieux, 1996). The identification and characterization of human (or another mammalian) staufen is desired as it could provide critical information in the transport, and proper localisation of mRNAs in subcellular compartments.

Staufen (Stau) was originally described as a dsRNA-binding protein in *Drosophila melanogaster* (1). It was further shown to specifically bind the 3' untranslated region of the mRNA for bicoid (2), a morphogen responsible for anterior body pattern formation in the early embryo. In *Drosophila*, Stau's principle function is to target mRNAs for localized translation (2, 3): it serves to localize oskar mRNA posteriorally (3) and anchors bicoid mRNA anteriorally in oocytes, and recently has been shown to localize prospero mRNA in neuroblasts (4). The human homologue (hStau) is hereinbelow further characterized and is shown to have several structural and functional domain similarities to its *Drosophila* counterpart (5).

A more thorough understanding of the structure-function relationship of mammalian staufen is needed to better understand its function in mammalian cells. There also remains a need to better understand the dsRNA-binding activity of mammalian staufen and to analyze the function and application thereof in cellular homoeostasy. In addition, this understanding could help characterize the important molecular determinants of staufen from lower eukaryotes.

It would be highly desirable to be provided with means to target molecules to RNA viruses, including retroviruses, such as HIV virions. It would also be desirable to be provided wth means to target molecules into such viruses and affect their structural organization and/or functional integrity and/or morphogenesis.

It would also be highly desirable to be provided with a protein, fragment or derivative thereof which permits the development of chimeric molecules that can be specifically targeted into RNA viruses in general, and more particularly retroviruses, including antiviruses such as HIV. Such chimeric molecules could be used for the treatment of RNA virus infections, retroviral infections and lentiviral infections.

It would also be highly desirable to be provided with a therapeutic agent which permits targeting of chimeric molecules into RNA virions, as a treatment for diseases caused by such virions.

It would also be highly desirable to be provided with the identification of novel molecular determinants responsible for the incorporation of proteins into virions via their interaction with genomic RNA, for RNA genome incorporation into RNA viruses, as well as the identification of molecular determinants involved in the targeting of RNA molecules to the RER.

It would also be highly desirable to be provided with means to target RNA molecules to the RER.

It would also be very desirable to be provided with therapeutic agent molecules which interfere with the molecular determinant responsible for RNA genome incorporation into RNA virions as well as agents which interfere with the targeting of RNA molecules to the RER as such agents could have therapeutic utility for the treatment of diseases including viral diseases.

It would further be highly desirable to be provided with an assay which enables the screening and identification of molecules which modulate the interaction between the molecular determinant responsible for RNA genome incorporation into RNA virions. As well, it would be highly desirable to be provided with an assay which enables the screening and identification of molecules which modulate the targeting of RNA molecules to the RER.

It would in addition be highly desirable to be provided with a method for screening and identifying molecules which act as modulating agents of RNA genome incorporation into RNA virions and as well as a method for screening and identifying molecules which act as modulating agents for the targeting of RNA molecules to RER.

The present invention seeks to meet these and other needs.

The present description refers to a number of documents, the content of which is herein incorporated by reference.

SUMMARY OF THE INVENTION

The human homologue of the double-stranded RNA (dsRNA)-binding protein, Staufen, is shown herein to be incorporated into HIV-1 virions, and this correlates with HIV-1 genomic RNA encapsidation. hStau is incorporated into clinical isolates of HIV-1, and several other retroviruses including HIV-2 and murine leukemia virus, and non-retroviral RNA viruses such as Reovirus, but is not detectable in DNA viruses. When hStau is overexpressed, a corresponding increase of hStau in virions is observed. Strikingly, this increase in hStau incorporation into HIV-1 is accompanied by a dramatic impairment of HIV-1 infectivity. This is the first demonstration of a dsRNA-binding protein within HIV-1 particles. This novel and unexpected finding may have important implications not only in retroviral genome sorting, assembly and infectivity, but also in RNA virus therapy in general, retrovirus therapy and more particularly HIV-1 therapy.

The invention concerns in general mammalian staufen and more particularly the sequence of the human and mouse staufen proteins and nucleic acid molecules encoding same.

The present invention further relates to the demonstration that staufen binds both dsRNA and tubulin in vitro via specific binding domains. Further, the invention relates to the localization of staufen in the cytoplasm in association with the rough endoplasmic reticulum, implicating this protein in the targeting of RNA to its site of translation.

More particularly, the present invention provides isolated polypeptides having the amino acid sequences shown in FIGS. 1A, 1B, 1C, 1D and FIG. 1'.

The present invention further relates to isolated nucleic acid molecules comprising polynucleotides which encode a staufen polypeptide and more particularly a mammalian staufen polypeptide. More paticularly, the present invention relates to isolated nucleic acid molecules encoding the staufen polypeptides having the amino acid sequences shown in FIGS. 1A, 1B, 1C and 1'.

The invention in addition relates to recombinant vectors harboring the isolated nucleic acid molecules of the present invention. More particularly, the invention relates to expression vectors which express the staufen polypeptides of the present invention and more particularly mammalian staufen. The present invention further relates to host cells containing such recombinant vectors or expression vectors, to methods of making such host cells, and to methods of making such vectors.

Further, the present invention provides screening assays and methods for identifying modulators of staufen activity and especially of mammalian staufen activity. More particularly, the present invention relates to assays and methods for screening and identifying compounds which can enhance or inhibit the RNA virion incorporation ability of staufen and especially mammalian staufen. In one particular embodiment of the present invention, the screening assay for identifying modulators of staufen's incorporation ability comprises contacting cells or extracts containing staufen and a candidate compound, assaying a cellular response or biological function of staufen such as virion incorporation or RER targeting, for example, wherein the potential modulating compound is selected when the cellular response or staufen's biological activity in the presence of the candidate compound is measurably different than in the absence thereof.

In addition, the present invention relates to methods for treating an animal (such as a human) infected with a RNA virus, which comprises administration thereto of a composition comprising a therapeutically effective amount of staufen (such as mammalian staufen) polypeptide, and/or staufen nucleic acid molecule encoding same, and/or modulators of staufen activity. In one embodiment, the present invention relates to an administration of a recombinant staufen molecule having an additional antiviral activity (i.e. RNAse or protease activity).

The invention further relates to the use of polypeptides and nucleic acid molecules encoding same of the present invention to target molecules into virions of RNA viruses. In a particular embodiment, such targeting finds utility for example, in packaging cell lines. In a particular embodiment, staufen is used as a carrier for virion targeting and is part of a fusion protein.

In accordance with the present invention, there is therefore provided, an isolated mammalian staufen protein exhibiting homology to mammalian staufen as well as lower eukaryotic staufen.

In accordance with the present invention, there is also provided, an isolated nucleic acid molecule comprising a polynucleotide sequence encoding mammalian staufen.

In accordance with another aspect of the present invention, there is provided, an isolated nucleic acid molecule comprising a polynucleotide sequence which hybridizes under stringent conditions to a polynucleotide sequence encoding mammalian staufen or to a sequence which is complementary thereto.

In accordance with yet another aspect of the present invention, there is provided a method of constructing a recombinant vector which comprises inserting an isolated nucleic acid molecule encoding mammalian staufen (or a derivative thereof) into a vector. In addition, there is also provided a recombinant vector harboring an isolated nucleic acid molecule encoding a *C. elegans* staufen or fragments or derivatives thereof. In addition, there is provided recombinant vectors harboring an isolated nucleic acid molecule encoding the molecular determinant of a mammalian or lower eukaryotic staufen, which is responsible for incorporation into RNA virions.

In accordance with a further aspect of the present invention, there is provided a method for making a recombinant cell comprising introducing thereinto a recombinant vector harboring a nucleic acid sequence encoding a staufen of the present invention.

In accordance with an additional aspect of the present invention, there is provided an antibody which recognizes specifically a staufen polypeptide or derivative thereof of the present invention.

The mammalian staufen polypeptides and nucleic acid molecules of the instant invention have been isolated from human and mouse. Nevertheless, it will be clear to the person of ordinary skill that the present invention should not be so limited. Indeed, using the teachings of the present invention and those of the art, homologues of hStau and mStau can be identified and isolated from other animal species. Non-limiting examples thereof include monkey, mouse, rat, rabbit, and frog. The significant identity between the human and mouse Staufen protein validates this contention.

The conservation of staufen between mammals and lower eukaryotes (*Drosphila* and *C. elegans*) further supports this notion. In addition, it suggests that certain embodiments of the present invention could be carried out using lower eukaryotic staufen or fragments or derivatives thereof.

The invention further relates to the morphogenesis RNA virions and more particularly of HIV virions and especially to the packaging of RNA genomes into RNA viruses.

The present invention further provides means to target molecules to RNA virions. In one particular embodiment, the present invention relates to such means to affect the morphogenesis of such RNA virions, thereby reducing infectivity thereof. In a particularly preferred embodiment, the present invention relates to a mammalian staufen protein which upon incorporation into HIV-1 virions significantly decreases the infectivity thereof.

BRIEF DESCRIPTION OF THE DRAWINGS

Having thus generally described the invention, reference will now be made to the accompanying drawings, showing by way of illustration a preferred embodiment thereof, and in which:

Figure 1A:
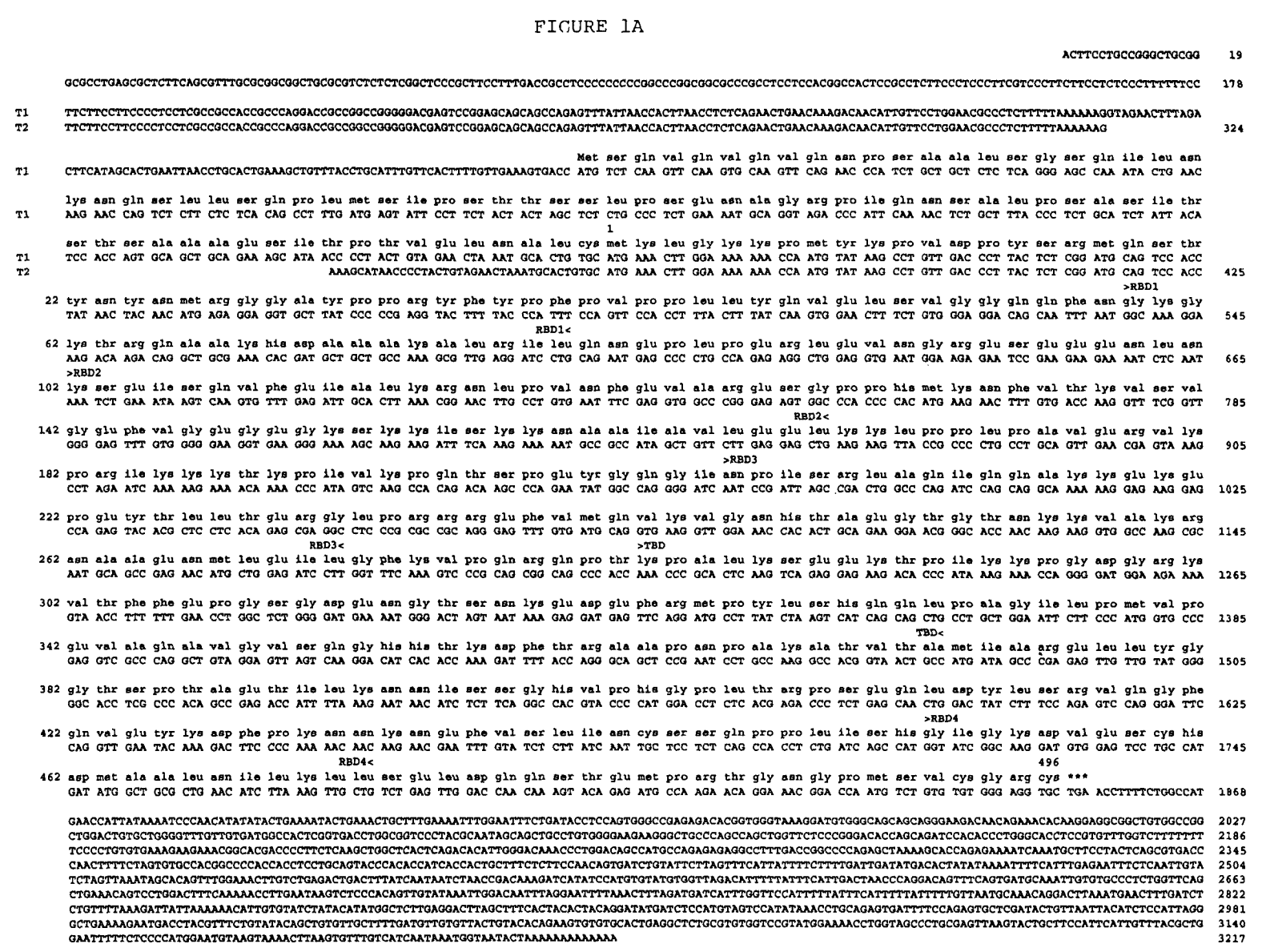
Figure 1B:
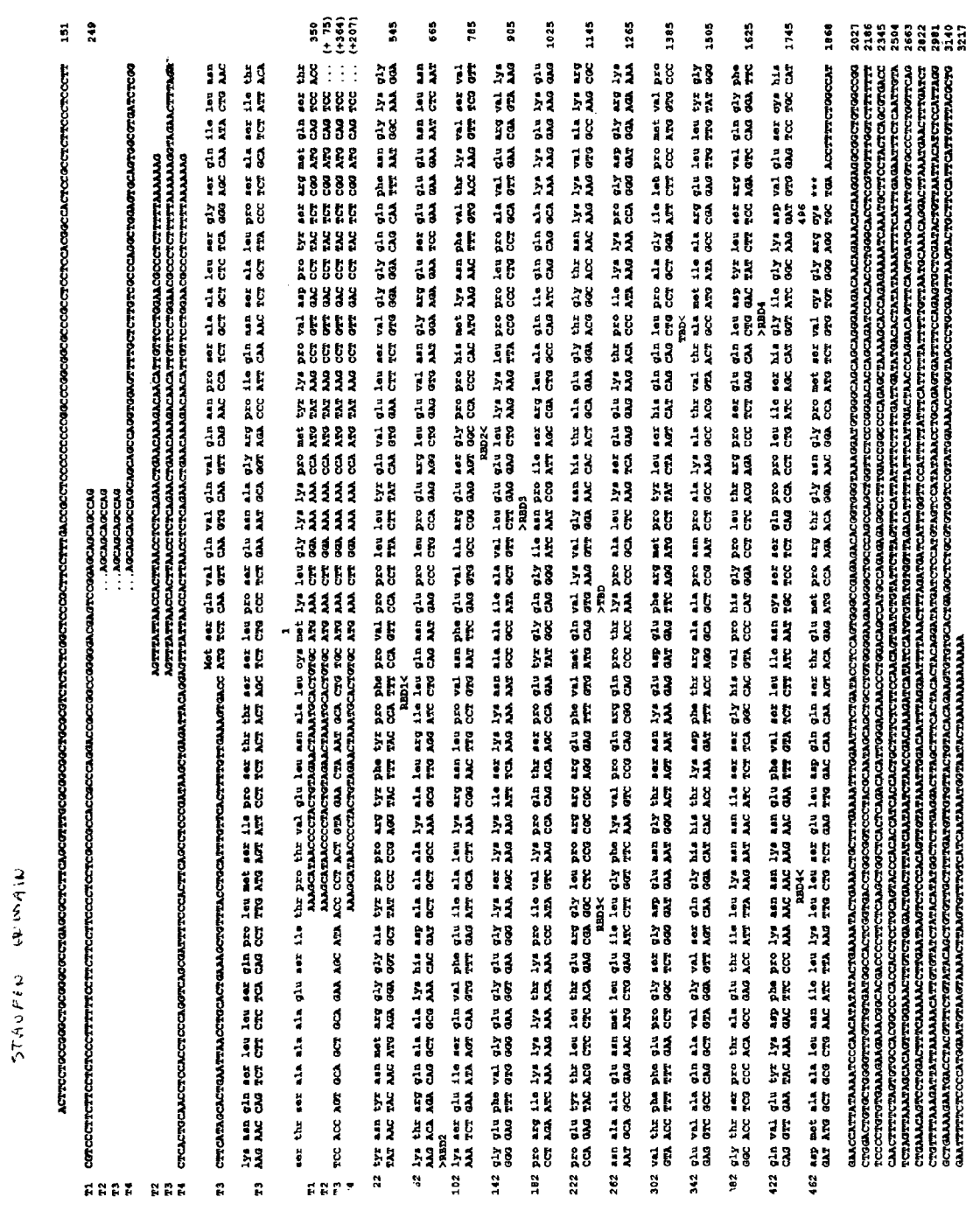
Figure 1C:
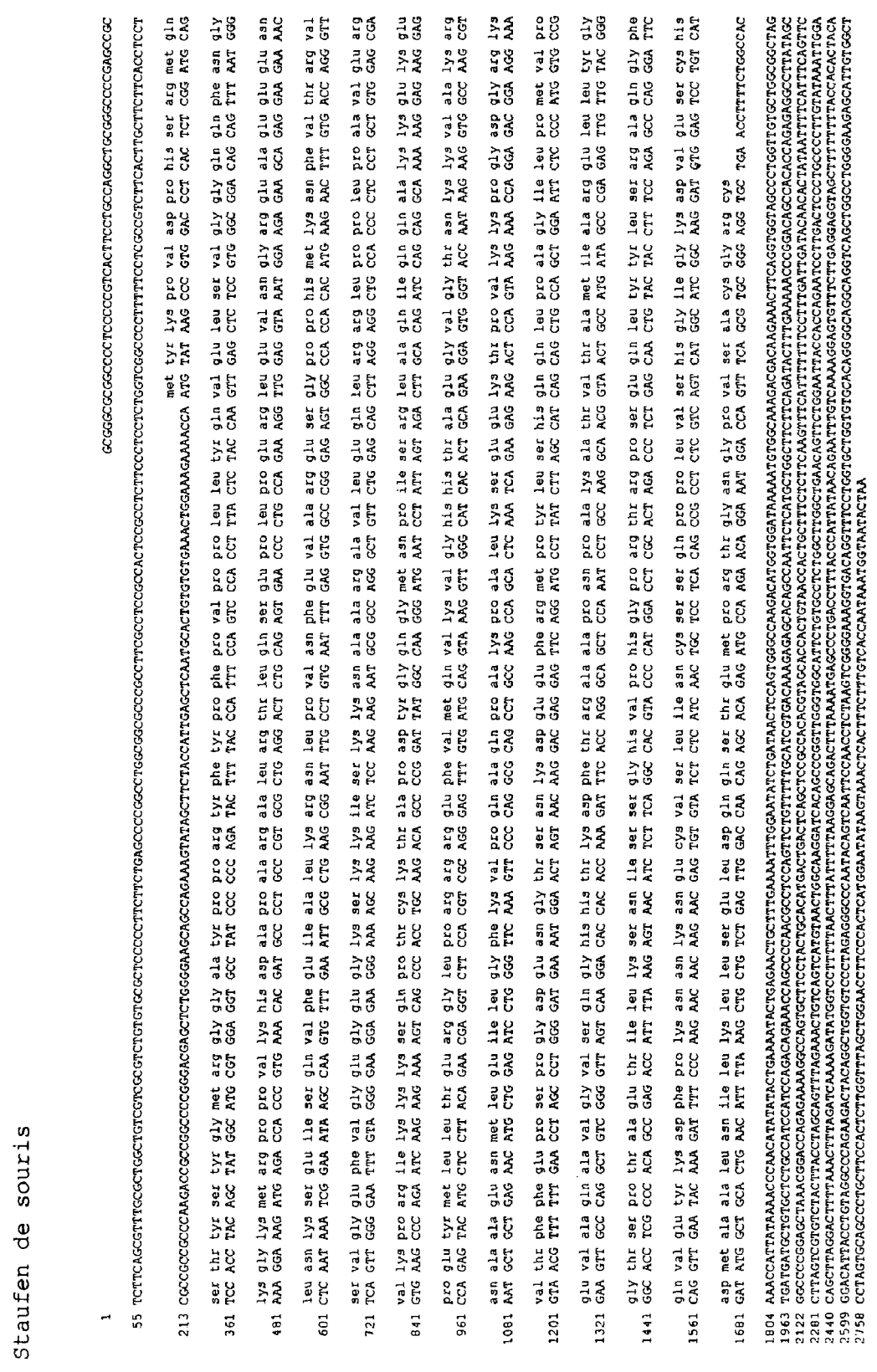

FIG. 1A shows an alignment of the two cDNAs of the human staufen cDNAs, designated T1 (SEQ ID NO: 1) and T2 (SEQ ID NO: 3) and the translation of the putative protein sequences thereof, starting at amino acid no. −81 and 1, respectively, and presented as the amino acid sequences in SEQ ID NO: 2 and SEQ ID NO: 4, respectively. The numbers refer to the sequence of the short cDNA. The positions of the 4 dsRNA-binding consensus domains (RBD1 to RBD4) and of the tubulin-binding domain (TBD) are indicated between brackets above the sequence. The sequences were deposited in the GenBank database under accession numbers AF061938 and AF061939.

FIG. 1B is similar to FIG. 1 but shows the alternative splicing which occurs in the human staufen gene and gives rise to 4 alternatively spliced transcripts, namely T1, a 3142 bp nucleotide sequence appearing in SEQ ID NO: 5 and encoding from nucleotide 288 to 1775 the protein appearing in SEQ ID NO: 4; T2, a 3217 bp nucleotide sequence discussed above and appearing in SEQ ID NO: 3 and also encoding from nucleotide 363 to 1850 the protein appearing in SEQ ID NO: 4; T3 (designated T1 in FIG. 1A), a 3506 bp nucleotide sequence appearing in SEQ ID NO: 1 and encoding from nucleotide 409 to 2139 the protein appearing in SEQ ID NO: 2; and T4, a 3348 bp nucleotide sequence appearing in SEQ ID NO: 6 and encoding from nucleotide 494 to 1981 the protein appearing in SEQ ID NO: 4. These 4 transcripts therefore give rise to the two proteins as described in FIG. 1 and in the text below.

FIG. 1C shows the nucleic acid (SEQ ID NO: 7) and predicted amino acid sequence (SEQ ID NO: 8) of mouse staufen.

FIG. 1D shows an alignment of the mouse (SEQ ID NO: 8) and human Staufen (SEQ ID NO: 4), highlighting the significant conservation of the protein during evolution. As per FIG. 1, the 4 dsRNA binding domains (RBD) and tubulin-binding domains are highlighted.

As shown in FIG. 1B, T1, T2 and T4 give rise to the short protein of 55 kDa (SEQ ID NO: 4) while T3 gives rise to the 63 kDa protein (SEQ ID NO: 2). FIG. 1'B shows an alignment between a region comprising the human Staufen tubulin-binding domain (SEQ ID NO: 11) and the human MAP1B microtubule-binding domain (SEQ ID NO: 12).

Figure 1:
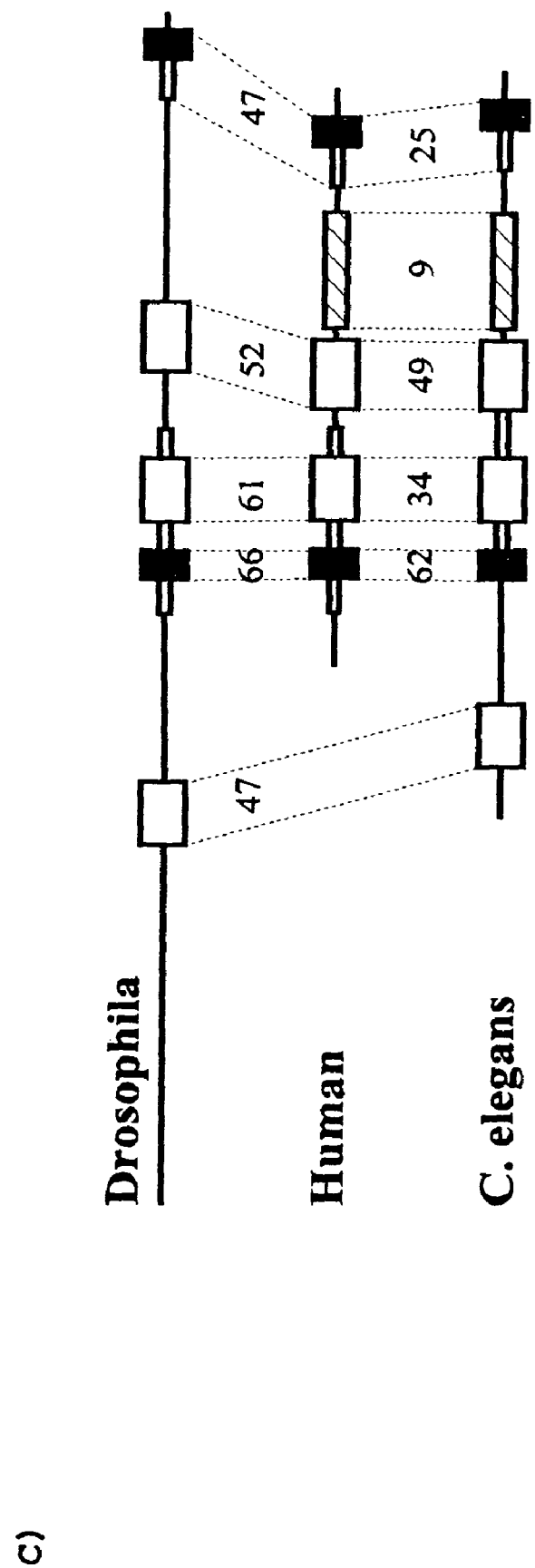
FIG. 1' shows an alignment between phylogenetically different Staufen proteins of *Drosophila* (SEQ ID NO: 9), *C. elegans* (SEQ ID NO: 10) and human (SEQ ID NO: 4). This alignment permits the elaboration of a consensus sequence for staufen.

Other objects, advantages and features of the present invention will become more apparent upon reading of the following non-restrictive description of preferred embodiments with reference to the accompanying drawing which is exemplary and should not be interpreted as limiting the scope of the present invention.

DESCRIPTION OF THE PREFERRED EMBODIMENT

The present invention therefore relates to staufen, a double-stranded RNA-binding protein which binds dsRNA via each of two full-length dsRNA-binding domains and tubulin via a region similar to the microtubule-binding domain of MAP1B. Immunofluorescent double-labeling of transfected mammalian cells revealed that Stau is localized to the rough endoplasmic reticulum (RER), implicating this RNA-binding protein in mRNA targeting to the RER. These results are the first demonstration of the association of an RNA-binding protein with the RER, implicating this class of proteins in the transport of RNA to its site of translation.

The human homologue of the double-stranded RNA (dsRNA)-binding protein, Staufen, is shown herein to be incorporated into HIV-1 virions, and this correlates with HIV-1 genomic RNA encapsidation. hStau is incorporated into clinical isolates of HIV-1, and several other retroviruses including HIV-2 and murine leukemia virus, and non-retroviral RNA viruses such as Reovirus, but is not detectable in DNA viruses. Experiments with poliovirus are underway and are expected to further demonstrate the role of staufen during the life cycle of RNA viruses in general. When hStau is overexpressed, a corresponding increase of hStau in virions is observed. Strikingly, however, this increase in hStau incorporation into HIV-1 is accompanied by a dramatic impairment of HIV-1 infectivity. This is the first demonstration of a dsRNA-binding protein within HIV-1 particles. This novel and unexpected finding may have important implications not only in retroviral genome sorting, assembly and infectivity, but also in RNA virus therapy in general and more in particularly HIV-1 therapy.

Nucleotide sequences are presented herein by single strand, in the 5' to 3' direction, from left to right, using the one letter nucleotide symbols as commonly used in the art and in accordance with the recommendations of the IUPAC-IUB Biochemical Nomenclature Commission.

Unless defined otherwise, the scientific and technological terms and nomenclature used herein have the same meaning as commonly understood by a person of ordinary skill to which this invention pertains. Generally, the procedures for cell cultures, infection, molecular biology methods and the like are common methods used in the art. Such standard techniques can be found in reference manuals such as for example Sambrook et al. (1989, Molecular Cloning—A Laboratory Manual, Cold Spring Harbor Laboratories) and Ausubel et al. (1994, Current Protocols in Molecular Biology, Wiley, N.Y.).

The present description refers to a number of routinely used recombinant DNA (rDNA) technology terms. Nevertheless, definitions of selected examples of such rDNA terms are provided for clarity and consistency.

As used herein, "nucleic acid molecule", refers to a polymer of nucleotides. Non-limiting examples thereof include DNA (i.e. genomic DNA, cDNA) and RNA molecules (i.e. mRNA). The nucleic acid molecule can be obtained by cloning techniques or synthesized. DNA can be double-stranded or single stranded (coding strand or non-coding strand [antisense]).

The term "isolated nucleic acid molecule" refers to a nucleic acid molecule purified from its natural environment. Non-limiting examples of an isolated nucleic acid molecule is a DNA sequence inserted into a vector, and a partially purified polynucleotide sequence in solution.

The term "recombinant DNA" as known in the art refers to a DNA molecule resulting from the joining of DNA segments. This is often referred to as genetic engineering.

The term "DNA segment", is used herein, to refer to a DNA molecule comprising a linear stretch or sequence of nucleotides. This sequence when read in accordance with the genetic code, can encode a linear stretch or sequence of amino acids which can be referred to as a polypeptide, protein, protein fragment and the like.

The terminology "amplification pair" refers herein to a pair of oligonucleotides (oligos) of the present invention, which are selected to be used together in amplifying a selected nucleic acid sequence by one of a number of types of amplification processes, preferably a polymerase chain reaction. Other types of amplification processes include ligase chain reaction, strand displacement amplification, or nucleic acid sequence-based amplification, as explained in greater detail below. As commonly known in the art, the oligos are designed to bind to a complementary sequence under selected conditions. For example, homologs of human or mouse staufen could be isolated using an amplification method such as PCR with an amplification pair designed by comparing the homology of the human and mouse sequences.

The nucleic acid (i.e. DNA or RNA) for practicing the present invention may be obtained according to well known methods.

As used herein, the term "physiologically relevant" is meant to describe interactions which can modulate transcription of a gene in its natural setting.

Oligonucleotide probes or primers of the present invention may be of any suitable length, depending on the particular assay format and the particular needs and targeted genomes employed. In general, the oligonucleotide probes or primers are at least 12 nucleotides in length, preferably between 15 and 24 molecules, and they may be adapted to be especially suited to a chosen nucleic acid amplification system. As commonly known in the art, the oligonucleotide probes and primers can be designed by taking into consideration the melting point of hydrizidation thereof with its targeted sequence (see below and in Sambrook et al., 1989, Molecular Cloning—A Laboratory Manual, 2nd Edition, CSH Laboratories; Ausubel et al., 1989, in Current Protocols in Molecular Biology, John Wiley & Sons Inc., N.Y.).

The terms "DNA oligonucleotide", or "DNA molecule" or "DNA sequence" refer to a molecule comprised of the deoxyribonucleotides adenine (A), guanine (G), thymine (T) and/or cytosine (C). Oligonucleotide or DNA can be found in linear DNA molecules or fragments, viruses, plasmids, vectors, chromosomes or synthetically derived DNA.

"Nucleic acid hybridization" refers generally to the hybridization of two single-stranded nucleic acid molecules having complementary base sequences, which under appropriate conditions will form a thermodynamically favored double-stranded structure. Examples of hybridization conditions can be found in the two laboratory manuals referred above (Sambrook et al., 1989, supra and Ausubel et al., 1989, supra) and are commonly known in the art. In the case of a hybridization to a nitrocellulose filter, as for example in the well known Southern blotting procedure, a nitrocellulose filter can be incubated overnight at 65° C. with a labeled probe in a solution containing high salt (5×SSC or 5×SSPE), 5× Denhardt's solution, 1% SDS, and 100 µg/ml denatured carried DNA (i.e. salmon sperm DNA). The non-specifically binding probe can then be washed off the filter by several washes in 0.2×SSC/0.1% SDS at a temperature which is selected in view of the desired stringency: room temperature (low stringency), 42° C. (moderate stringency) or 65° C. (high stringency). The selected temperature is based on the melting temperature (Tm) of the DNA hybrid. Of course, RNA-DNA hybrids can also be formed and detected. In such cases, the conditions of hybridization and washing can be adapted according to well known methods by the person of ordinary skill. Stringent conditions will be preferably used (Sambrook et al., 1989, supra). As well known in the art other stringent hybridization conditions can be used (i.e. 42° C. in the presence of 50% of formamide).

Probes of the invention can be utilized with naturally occurring sugar-phosphate backbones as well as modified backbones including phosphorothioates, dithionates, alkyl phosphonates and α-nucleotides and the like. Modified sugar-phosphate backbones are generally taught by Miller, 1988 (Ann. Reports Med. Chem. 23:295) and Moran et al., 1987 (Nucl. Acids Res., 14:5019). Probes of the invention can be constructed of either ribonucleic acid (RNA) or deoxyribonucleic acid (DNA), and preferably of DNA.

The types of detection methods in which probes can be used include Southern blots (DNA detection), dot or slot blots (DNA, RNA), and Northern blots (RNA detection). labeled proteins could also be used to detect a particular nucleic acid sequence to which it binds. Other detection methods include kits containing probes on a dipstick setup and the like.

Although the present invention is not specifically dependent on the use of a label for the detection of a particular nucleic acid sequence, such a label might be beneficial, by increasing the sensitivity of the detection. Furthermore, it enables automation. Probes can be labeled according to numerous well known methods (Sambrook et al., 1989, supra). Non-limiting examples of labels include $^3$H, $^{14}$C, $^{32}$P, and $^{35}$S. Non-limiting examples of detectable markers include ligands, fluorophores, chemiluminescent agents, enzymes, and antibodies. Other detectable markers for use with probes, which can enable an increase in sensitivity of the method of the invention, include biotin and radionucleotides. It will become evident to the person of ordinary skill that the choice of a particular label dictates the manner in which it is bound to the probe.

As commonly known, radioactive nucleotides can be incorporated into probes of the invention by several methods. Non-limiting examples thereof include kinasing the 5' ends of the probes using gamma $^{32}$P ATP and polynucleotide kinase, using the Klenow fragment of Pol I of *E. coli* in the presence of radioactive dNTP (i.e. uniformly labeled DNA probe using random oligonucleotide primers in low-melt gels), using the SP6/T7 system to transcribe a DNA segment in the presence of one or more radioactive NTP, and the like.

As used herein, "oligonucleotides" or "oligos" define a molecule having two or more nucleotides (ribo or deoxyribonucleotides). The size of the oligo will be dictated by the particular situation and ultimately on the particular use thereof and adapted accordingly by the person of ordinary skill. An oligonucleotide can be synthetised chemically or derived by cloning according to well known methods.

As used herein, a "primer" defines an oligonucleotide which is capable of annealing to a target sequence, thereby creating a double stranded region which can serve as an initiation point for DNA synthesis under suitable conditions.

Amplification of a selected, or target, nucleic acid sequence may be carried out by a number of suitable methods. See generally Kwoh et al., 1990, Am. Biotechnol. Lab. 8:14–25. Numerous amplification techniques have been described and can be readily adapted to suit particular needs of a person of ordinary skill. Non-limiting examples of amplification techniques include polymerase chain reaction (PCR), ligase chain reaction (LCR), strand displacement amplification (SDA), transcription-based amplification, the Qβ replicase system and NASBA (Kwoh et al., 1989, Proc. Natl. Acad. Sci. USA 86, 1173–1177; Lizardi et al., 1988, BioTechnology 6:1197–1202; Malek et al., 1994, Methods Mol. Biol., 28:253–260; and Sambrook et al., 1989, supra). Preferably, amplification will be carried out using PCR.

Polymerase chain reaction (PCR) is carried out in accordance with known techniques. See, e.g., U.S. Pat. Nos. 4,683,195; 4,683,202; 4,800,159; and 4,965,188 (the disclosures of all three U.S. patent are incorporated herein by reference). In general, PCR involves, a treatment of a nucleic acid sample (e.g., in the presence of a heat stable DNA polymerase) under hybridizing conditions, with one oligonucleotide primer for each strand of the specific sequence to be detected. An extension product of each primer which is synthesized is complementary to each of the two nucleic acid strands, with the primers sufficiently complementary to each strand of the specific sequence to hybridize therewith. The extension product synthesized from each primer can also serve as a template for further synthesis of extension products using the same primers. Following a sufficient number of rounds of synthesis of extension products, the sample is analysed to assess whether the sequence or sequences to be detected are present. Detection of the amplified sequence may be carried out by visualization following EtBr staining of the DNA following gel electrophores, or using a detectable label in accordance with known techniques, and the like. For a review on PCR techniques (see PCR Protocols, A Guide to Methods and Amplifications, Michael et al. Eds, Acad. Press, 1990).

Ligase chain reaction (LCR) is carried out in accordance with known techniques (Weiss, 1991, Science 254:1292). Adaptation of the protocol to meet the desired needs can be carried out by a person of ordinary skill. Strand displacement amplification (SDA) is also carried out in accordance with known techniques or adaptations thereof to meet the particular needs (Walker et al., 1992, Proc. Natl. Acad. Sci. USA 89:392–396; and ibid., 1992, Nucleic Acids Res. 20:1691–1696.

As used herein, the term "gene" is well known in the art and relates to a nucleic acid sequence defining a single protein or polypeptide. A "structural gene" defines a DNA sequence which is transcribed into RNA and translated into a protein having a specific amino acid sequence thereby giving rise the a specific polypeptide or protein. It will readily recognized by the person of ordinary skill, that the nucleic acid sequence of the present invention can be incorporated into anyone of numerous established kit formats which are well known in the art.

A "heterologous" (i.e. a heterologous gene) region of a DNA molecule is a subsegment segment of DNA within a larger segment that is not found in association therewith in nature. The term "heterologous" can be similarly used to define two polypeptidic segments not joined together in nature. Non-limiting examples of heterologous genes include reporter genes such as luciferase, chloramphenicol acetyl transferase, β-galactosidase, and the like which can be juxtaposed or joined to heterologous control regions or to heterologous polypeptides.

The term "vector" is commonly known in the art and defines a plasmid DNA, phage DNA, viral DNA and the like, which can serve as a DNA vehicle into which DNA of the present invention can be cloned. Numerous types of vectors exist and are well known in the art.

The term "expression" defines the process by which a structural gene is transcribed into mRNA (transcription), the mRNA is then being translated (translation) into one polypeptide (or protein) or more.

The terminology "expression vector" defines a vector or vehicle as described above but designed to enable the expression of an inserted sequence following transformation into a host. The cloned gene (inserted sequence) is usually placed under the control of control element sequences such as promoter sequences. The placing of a cloned gene under such control sequences is often refered to as being operably linked to control elements or sequences.

Operably linked sequences may also include two segments that are transcribed onto the same RNA transcript. Thus, two sequences, such as a promoter and a "reporter sequence" are operably linked if transcription commencing in the promoter will produce an RNA transcript of the reporter sequence. In order to be "operably linked" it is not necessary that two sequences be immediately adjacent to one another.

Expression control sequences will vary depending on whether the vector is designed to express the operably linked gene in a prokaryotic or eukaryotic host or both (shuttle vectors) and can additionally contain transcriptional elements such as enhancer elements, termination sequences, tissue-specificity elements, and/or translational initiation and termination sites. Typically, expression vectors are prokaryote specific or eukaryote specific although shuttle vectors are also widely available.

Prokaryotic expression are useful for the preparation of large quantities of the protein encoded by the DNA sequence of interest. This protein can be purified according to standard protocols that take advantage of the intrinsic properties thereof, such as size and charge (i.e. SDS gel electrophoresis, gel filtration, centrifugation, ion exchange chromatography . . . ). In addition, the protein of interest can be purified via affinity chromatography using polyclonal or monoclonal antibodies. The purified protein can be used for therapeutic applications.

The DNA construct can be a vector comprising a promoter that is operably linked to an oligonucleotide sequence of the present invention, which is in turn, operably linked to a heterologous gene, such as the gene for the luciferase reporter molecule. "Promoter" refers to a DNA regulatory region capable of binding directly or indirectly to RNA polymerase in a cell and initiating transcription of a downstream (3' direction) coding sequence. For purposes of the present invention, the promoter is bound at its 3' terminus by the transcription initiation site and extends upstream (5' direction) to include the minimum number of bases or elements necessary to initiate transcription at levels detectable above background. Within the promoter will be found a transcription initiation site (conveniently defined by mapping with S1 nuclease), as well as protein binding domains (consensus sequences) responsible for the binding of RNA polymerase. Eukaryotic promoters will often, but not always, contain "TATA" boxes and "CCAT" boxes. Prokaryotic promoters contain Shine-Dalgarno sequences in addition to the −10 and −35 consensus sequences.

As used herein, the designation "functional derivative" denotes, in the context of a functional derivative of a sequence whether an nucleic acid or amino acid sequence, a molecule that retains a biological activity (either function or structural) that is substantially similar to that of the original sequence. This functional derivative or equivalent may be a natural derivatives or may be prepared synthetically. Such derivatives include amino acid sequences having substitutions, deletions, or additions of one or more amino acids, provided that the biological activity of the protein is conserved. The same applies to derivatives of nucleic acid sequences which can have substitutions, deletions, or additions of one or more nucleotides, provided that the biological activity of the sequence is generally maintained. When relating to a protein sequence, the substituting amino acid as chemico-physical properties which are similar to that of the substituted amino acid. The similar chemico-physical properties include, similarities in charge, bulkiness, hydrophobicity, hydrophylicity and the like. The term "functional derivatives" is intended to include "functional fragments", "functional segments", "functional variants", "functional analogs" or "functional chemical derivatives" of the subject matter of the present invention. "Fragments" of the nucleic acid molecules according to the present invention refer to such molecules having at least 12 nt, more particularly at least 18 nt, and even more preferably at least 24 nt which have utility as diagnostic probes and/or primers. It will become apparent to the person of ordinary skill that larger fragments of 100 nt, 1000 nt, 2000 nt and more also find utility in accordance with the present invention.

The term "at least 24 nt" is meant to refer to 24 contiguous nt of a chosen sequence such as shown for example in FIGS. 1A, 1B, 1C, 1D and 1'.

The term "functional variant" refers herein to a protein or nucleic acid molecule which is substantially similar in structure and biological activity to the protein or nucleic acid of the present invention.

The functional derivatives of the present invention can be synthesized chemically or produced through recombinant DNA technology, all these methods are well known in the art.

The term "molecule" is used herein in a broad sense and is intended to include natural molecules, synthetic molecules, and mixture of natural and synthetic molecules. The term "molecule" is also meant to cover a mixture of more than one molecule such as for example pools or libraries of molecules. Non-limiting examples of molecules include chemicals, biological macromolecules, cell extracts and the like. The term "compound" is used herein interchangeably with molecule and is similarly defined.

Nucleic acid fragments in accordance with the present invention include epitope-encoding portions of the polypeptides of the invention. Such portions can be identified by the person of ordinary skill using the nucleic acid sequences of the present invention in accordance with well known methods. Such epitopes are useful in raising antibodies that are specific to the polypeptides of the present invention. The invention also provides nucleic acid molecules which comprise polynucleotide sequences capable of hybridizing under stringent conditions to the polynucleotide sequences of the present invention or to portions thereof.

The term hybridizing to a "portion of a polynucleotide sequence" refers to a polynucleotide which hybridizes to at least 12 nt, more preferably at least 18 nt, even more preferably at least 24 nt and especially to about 50 nt of a polynucleotide sequence of the present invention.

The present invention further provides isolated nucleic acid molecules comprising a polynucleotide sequences which is at least 95% identical, and preferably from 96% to 99% identical to the polynucleic acid sequence encoding the full length staufen polypeptides (i.e. 55 and 63 kDa hStau) or fragments and/or derivatives thereof. Methods to compare sequences and determine their homology/identity are well known in the art and exemplified herein.

As used herein, "chemical derivatives" is meant to cover additional chemical moieties not normally part of the subject matter of the invention. Such moieties could affect the physico-chemical characteristic of the derivative (i.e. solubility, absorption, half life and the like, decrease of toxicity). Such moieties are exemplified in Remington's Pharmaceutical Sciences (1980). Methods of coupling these chemical-physical moieties to a polypeptide are well known in the art.

The term "allele" defines an alternative form of a gene which occupies a given locus on a chromosome.

As commonly known, a "mutation" is a detectable change in the genetic material which can be transmitted to a daughter cell. As well known, a mutation can be, for example, a detectable change in one or more deoxyribonucleotide. For example, nucleotides can be added, deleted, substituted for, inverted, or transposed to a new position. Spontaneous mutations and experimentally induced mutations exist. The result of a mutations of nucleic acid molecule is a mutant nucleic acid molecule. A mutant polypeptide can be encoded from this mutant nucleic acid molecule.

As used herein, the term "purified" refers to a molecule having been separated from a cellular component. Thus, for example, a "purified protein" has been purified to a level not found in nature. A "substantially pure" molecule is a molecule that is lacking in all other cellular components.

The term "isolated polypeptide" refers to a polypeptide removed from its natural environment. Non-limiting examples of isolated polypeptides include a polypeptide produced recombinantly in a host cell and partially or substantially purified polypeptides from such host cells. The polypeptides of the present invention comprise polypeptides encoded by the nucleic acid molecules of the present invention, as shown for example in FIGS. 1A, 1B, 1C, 1D and 1'. The present invention also provides polypeptides comprising amino acids sequences which are at least 95% homologous, preferably from 96–99% homologous, even more preferably at least 95% identical and especially preferably from 96% to 99% identical to the full length staufen polypeptide sequence or fragments or derivatives thereof.

As used herein, the terms "molecule", "compound" or "ligand" are used interchangeably and broadly to refer to natural, synthetic or semi-synthetic molecules or compounds. The term "molecule" therefore denotes for examples chemicals, macromolecules, cell or tissue extracts (from plants or animals) and the like. Non-limiting examples of molecules include nucleic acid molecules, peptides, antibodies, carbohydrates and pharmaceutical agents. The agents can be selected and screened by a variety of means including random screening, rational selection and by rational design using for example protein or ligand modelling methods such as computer modelling. The terms "rationally selected" or "rationally designed" are meant to define compounds which have been chosen based on the configuration of the interaction domains of the present invention. As will be understood by the person of ordinary skill, macromolecules having non-naturally occurring modifications are also within the scope of the term "molecule". For example, peptidomimetics, well known in the pharmaceutical industry and generally referred to as peptide analogs can be generated by modelling as mentioned above. Similarly, in a preferred embodiment, the polypeptides of the present invention are modified to enhance their stability. It should be understood that in most cases this modification should not alter the biological activity of the interaction domain. The molecules identified in accordance with the teachings of the present invention have a therapeutic value is diseases or conditions in which the physiology or homeastasis of the cell and/or tissue is compromised by a defect in in modulating gene expression and/or translation. Alternatively, the molecules identified in accordance with the teachings of the present invention find utility in the development of more efficient cell lines or cell extracts for translating mRNAs. Non-limiting examples of diseases and/or conditions in which the protein and/or nucleic acid molecules of the present invention find utility include cancer, apoptosis and aberrant proliferation of cells.

As used herein, agonists and antagonists of translation activity also include potentiators of known compounds with such agonist or antagonist properties. In one embodiment, agonists can be detected by contacting the indicator cell with a compound or mixture or library of molecules, for a fixed period of time, and then determining the effect of the compound on the cell.

The level of gene expression of the reporter gene (e.g. the level of luciferase, or β-gal, produced) within the treated cells can be compared to that of the reporter gene in the absence of the molecule(s). The difference between the levels of gene expression indicates whether the molecule(s) of interest agonizes the aforementioned interaction. The magnitude of the level of reporter gene product expressed (treated vs. untreated cells) provides a relative indication of the strength of that molecule(s) as an agonist. The same type of approach can also be used in the presence of an antagonist(s).

Alternatively, an indicator cell in accordance with the present invention can be used to identify antagonists. For example, the test molecule or molecules are incubated with the host cell in conjunction with one or more agonists held at a fixed concentration. An indication and relative strength of the antagonistic properties of the molecule(s) can be provided by comparing the level of gene expression in the indicator cell in the presence of the agonist, in the absence of test molecules vs in the presence thereof. Of course, the antagonistic effect of a molecule can also be determined in the absence of agonist, simply by comparing the level of expression of the reporter gene product in the presence and absence of the test molecule(s).

It shall be understood that the "in vivo" experimental model can also be used to carry out an "in vitro" assay. For example, cellular extracts from the indicator cells can be prepared and used in one of the aforementioned "in vitro" tests (such as binding assays or in vitro translations).

As used herein the recitation "indicator cells" refers to cells wherein an interaction between staufen and dsRNA and/or staufen and tubulin for example is coupled to an identifiable or selectable phenotype or characteristic such that it provides an assessment of the interaction between these domains. Such indicator cells can be used in the screening assays of the present invention. In certain embodiments, the indicator cells have been engineered so as to express a chosen derivative, fragment, homolog, or mutant of staufen. The cells can be yeast cells or higher eukaryotic cells such as mammalian cells (WO 96/41169). In one particular embodiment, the indicator cell is a yeast cell harboring vectors enabling the use of the two hybrid system technology, as well known in the art (Ausubel et al., 1994, supra) and can be used to test a compound or a library thereof. In one embodiment, a reporter gene encoding a selectable marker or an assayable protein can be operably linked to a control element such that expression of the selectable marker or assayable protein is dependent on the interaction of the a staufen domain with a binding partner (i.e. tubulin). Such an indicator cell could be used to rapidly screen at high-throughput a vast array of test molecules. In a particular embodiment, the reporter gene is luciferase or β-Gal.

As exemplified herein below in one embodiment, at least one staufen domain may be provided as a fusion protein. The design of constructs therefor and the expression and production of fusion proteins are exemplified herein (i.e. Example 2) and are well known in the art (Sambrook et al., 1989, supra; and Ausubel et al., 1994, supra). In a particular embodiment, both the binding partner of staufen and staufen are part of fusion proteins.

Non-limiting examples of such fusion proteins include a hemaglutinin A (HA) fusions and Gluthione-S-transferase (GST) fusions, HIS fusions, FLAG fusions, and Maltose binding protein (MBP) fusions. In certain embodiments, it might be beneficial to introduce a protease cleavage site between the two polypeptide sequences which have been fused. Such protease cleavage sites between two heterologously fused polypeptides are well known in the art.

In certain embodiments, it might also be beneficial to fuse the interaction domains of the present invention to signal peptide sequences enabling a secretion of the fusion protein from the host cell. Signal peptides from diverse organisms are well known in the art. Bacterial OmpA and yeast Suc2 are two non-limiting examples of proteins containing signal sequences. In certain embodiments, it might also be beneficial to introduce a linker (commonly known) between the interaction domain and the heterologous polypeptide portion. Such fusion protein find utility in the assays of the present invention as well as for purification purposes, detection purposes and the like.

For certainty, the sequences and polypeptides useful to practice the invention include without being limited thereto mutants, homologs, subtypes, alleles and the like. It shall be understood that generally, the sequences of the present invention should encode a functional (albeit defective) interaction domain. It will be clear to the person of ordinary skill that whether an interaction domain of the present invention, variant, derivative, or fragment thereof retains its function in binding to its partner can be readily determined by using the teachings and assays of the present invention and the general teachings of the art.

As exemplified herein below, the interaction domains of the present invention can be modified, for example by in vitro mutagenesis, to dissect the structure-function relationship thereof and permit a better design and identification of modulating compounds. However, some derivative or analogs having lost their biological function of interacting with their respective interaction partner may still find utility, for example for raising antibodies. Such analogs or derivatives could be used for example to raise antibodies to the interaction domains of the present invention. These antibodies could be used for detection or purification purposes. In addition, these antibodies could also act as competitive or non-competitive inhibitor and be found to be modulators of staufen activity.

A host cell or indicator cell has been "transfected" by exogenous or heterologous DNA (e.g. a DNA construct) when such DNA has been introduced inside the cell. The transfecting DNA may or may not be integrated (covalently linked) into chromosomal DNA making up the genome of the cell. In prokaryotes, yeast, and mammalian cells for example, the transfecting DNA may be maintained on an episomal element such as a plasmid. With respect to eukaryotic cells, a stably transfected cell is one in which the transfecting DNA has become integrated into a chromosome so that it is inherited by daughter cells through chromosome replication. This stability is demonstrated by the ability of the eukaryotic cell to establish cell lines or clones comprised of a population of daughter cells containing the transfecting DNA. Transfection methods are well known in the art (Sambrook et al., 1989, supra; Ausubel et al., 1994, supra). It will be understood that extracts from animal cells or mammalian cells for example could be used in certain embodiments, to compensate for the lack of certain factors in lower eukaryotic indicator cells.

In general, techniques for preparing antibodies (including monoclonal antibodies and hybridomas) and for detecting antigens using antibodies are well known in the art (Campbell, 1984, In "Monoclonal Antibody Technology: Laboratory Techniques in Biochemistry and Molecular Biology", Elsevier Science Publisher, Amsterdam, The Netherlands) and in Harlow et al., 1988 (in: Antibody—A Laboratory Manual, CSH Laboratories). The present invention also provides polyclonal, monoclonal antibodies, or humanized versions thereof, chimeric antibodies and the like which inhibit or neutralize their respective interaction domains and/or are specific thereto.

The present invention also provides antisense nucleic acid molecules which can be used for example to decrease or abrogate the expression of staufen. An antisense nucleic acid molecule according to the present invention refers to a molecule capable of forming a stable duplex or triplex with a portion of its targeted nucleic acid sequence (DNA or RNA). The use of antisense nucleic acid molecules and the design and modification of such molecules is well known in the art as described for example in WO 96/32966, WO 96/11266, WO 94/15646, WO 93/08845, and U.S. Pat. No. 5,593,974. Antisense nucleic acid molecules according to the present invention can be derived from the nucleic acid sequences and modified in accordance to well known methods. For example, some antisense molecules can be designed to be more resistant to degradation to increase their affinity to their targeted sequence, to affect their transport to chosen cell types or cell compartments, and/or to enhance their lipid solubility by using nucleotide analogs and/or substituting chosen chemical fragments thereof, as commonly known in the art.

From the specification and appended claims, the term therapeutic agent should be taken in a broad sense so as to also include a combination of at least two such therapeutic agents. Further, the DNA segments or proteins according to the present invention can be introduced into individuals in a number of ways. For example, erythropoietic cells can be isolated from the afflicted individual, transformed with a DNA construct according to the invention and reintroduced to the afflicted individual in a number of ways, including intravenous injection. Alternatively, the DNA construct can be administered directly to the afflicted individual, for example, by injection in the bone marrow. The DNA construct can also be delivered through a vehicle such as a liposome, or nanoerythrosome which can be designed to be targeted to a specific cell type, and engineered to be administered through different routes.

For administration to humans, the prescribing medical professional will ultimately determine the appropriate form and dosage for a given patient, and this can be expected to vary according to the chosen therapeutic regimen (i.e DNA construct, protein, cells), the response and condition of the patient as well as the severity of the disease.

Composition within the scope of the present invention should contain the active agent (i.e. fusion protein, nucleic acid, and molecule) in an amount effective to achieve an inhibitory effect on HIV and related viruses while avoiding adverse side effects. Typically, the nucleic acids in accordance with the present invention can be administered to mammals (i.e. humans) in doses ranging from 0.005 to 1 mg per kg of body weight per day of the mammal which is treated. Pharmaceutically acceptable preparations and salts of the active agent are within the scope of the present invention and are well known in the art (Remington's Pharmaceutical Science, 16th Ed., Mack Ed.). For the administration of polypeptides, antagonists, agonists and the like, the amount administered should be chosen so as to avoid adverse side effects. The dosage will be adapted by the clinician in accordance with conventional factors such as the extent of the disease and different parameters from the patient. Typically, 0.001 to 50 mg/kg/day will be administered to the mammal.

As used herein, "RNA viruses" is used broadly to cover retroviruses and non-retroviruses (such as Reovirus and poliovirus).

As used herein, HIV is used loosely to refer to HIV-1, HIV-2 and to SIV and related viruses.

The present invention is illustrated in further detail by the following non-limiting examples.

EXAMPLE 1

Molecular Cloning and Sequencing of the cDNAs

In order to clone a human staufen homologue, the GenBank database was searched with *Drosophila* dsRNA-binding domain sequences to find consensus sequences and eventually design degenerate oligonucleotide primers for RT-PCR. However, searching in the expressed sequence tags (EST) database identified a partial sequence, clone HFBDQ83 (GenBank accession number T06248), with high homology to the *Drosophila* sequence. This clone was purchased from the American Type Culture Collection and used as a probe to screen both human brain (Clontech) and foetal total mouse (a generous gift from A. Royal) cDNA libraries as described previously (VVickham and DesGroseillers, 1991). DNA from the isolated λGT10 clones was subcloned into a Bluescript™ vector (Stratagene). Double-stranded DNA was sequenced by the dideoxynucleotide method, according to Sequenase™ protocols (United States Biochemical Corp.).

EXAMPLE 2

Construction of Fusion Proteins

The 1.2 kbp BamHI fragment of the human HFBDQ83 cDNA was subcloned in frame in either pQE32 (Qiagen) or pMAL-c (New England Biolabs) thus generating the protein fused to a hexahistidine tag or to the maltose-binding protein (MBP), respectively. The protein was expressed in bacteria by inducing with IPTG, as recommended by the manufacturer. Full-length and internal fragments of the mStau protein were PCR-amplified and cloned into pMaI-c to produce fusion proteins with the maltose-binding protein. For the expression of the internal domains, which do not contain an endogenous stop codon, the PCR fragments were cloned in a modified pMaI-c vector (pMaI-stop) in which stop codons were introduced at the HindIII site, by the ligation of the annealed complementary oligonucleotides 5'-AGCTTAATTAGCTGAC-3' (SEQ ID NO:13) and 5'-AGCTGTCAGCTAATTA-3' (SEQ ID NO:14). The MBP/mSTAU fusion protein, containing the full-length mStau sequence, was generated by PCR amplification with Vent DNA polymerase (New England BioLabs), using the primer pair 5'-CCTGGATCCGAAAG-TATAGCTTCTACCATTG-3' (SEQ ID NO:15) and 5'-TACATAAGCTTCTAGAT-GGC-CAGAAAAGGTTCAGCA-3' (SEQ ID NO:16). The resulting 1562 bp fragment was digested with HindIII and BamHI, and ligated in the pMaI-c vector. The C-terminal fragment (mSTAU-C) was amplified with the primer pair 5'-GGAT-GMTCCTATTAGTAGACTTGCAC-3' (SEQ ID NO:17) and 5'-TACATAAGC-TTCTAGATGGCCAGAAAAGGT-TCAG-CA-3' (SEQ ID NO:23), digested with HindIII and cloned in the EagI* and HndIII sites of pMaI-c. EagI* was created by filling in the cohesive ends of EagI* pMaI-c vector using the Klenow fragment of DNA polymerase I. This fusion vector was then digested with SacI and EcoRI and the resulting fragment was subcloned in the pMaI-stop vector to generate the mSTAU-RBD3 construct. The mSTAU-TBD construct was prepared by PCR using the primer pair 5'-GCTCTAGATTCAAAG-TTCCCCAGGC-GCAG-3' (SEQ ID NO:18) and 5'-TTTAAGCTTCTCAGA-GGGTCTAGT-GCGAG-3' (SEQ ID NO:19); the product was digested with XbaI and HindIII and cloned in the pMaI-stop vector. mSTAU-RBD2 and mSTAU-RBD1 were constructed by first amplifying a fragment using the primer pair 5'-CAATGTATAAGCCCGTGGACCC-3' (SEQ ID NO:20) and 5'-AAAAAGCTTGTGCAAGTCTACTAAT-AGGATTCACC-3' (SEQ ID NO:21). The resulting product was digested with HindIII and cloned in the EagI* and HindIII sites of the pMaI-stop vector. This vector was then used to purify the 398 bp PstI and HindIII fragment, which was subcloned in the pMAL-stop vector to generate the mSTAU-RBD2 construct. In the same way, the mSTAU-RBD1 vector was obtained by digestion with SmaI and StuI, followed by recircularization of the digestion product using T4 DNA ligase. The mSTAU-RBD4 was PCR amplified using the primer pair 5'-ATAGCCCGAGAGTTGTTG-3' (SEQ ID NO:22) and 5'-TACAT-AAGCTTCTAGATGGC-CAGAAAAGGTTCAGCA-3' (SEQ ID NO:23). HindIII and ligated in the pMaI-stop vector at the StuI and HindIII sites. All the MBP/staufen fusion plasmids were transformed in the BL-21 *E. coli* strain. The fusion proteins were obtained after induction with 1 mM IPTG for 2–3 hours. Cells were lysed in SDS-PAGE loading buffer for immediate use, or frozen at −80° C. for storage.

EXAMPLE 3

Antibody Production and Western Blotting

For the production of antibodies, a large amount of the his/hStau fusion protein was purified on Ni-NTA resin (Qiagen), as recommended by the manufacturers, and injected into rabbits, as done previously (Aloyz and Des-Groseillers, 1995). For western blotting, cells were lysed in 1% n-octylglucosid, 1 mM PMSF, 1 mg/ml aprotinin and 1 mg/ml pepstatin A in PBS. Protein extracts were quantified by the Bradford method (Bio-Rad), and similar amounts of proteins were separated on 10% SDS-polyacrylamide gels and transferred onto nitrocellulose membranes. Membranes were blocked for 30 min in TBS (Tris-buffered saline) plus 5% dry milk and incubated with primary antibodies in TBS plus 0.05% Tween™ for 1 hr at room temperature. Detection was accomplished by incubating the blots with peroxydase-conjugated anti-rabbit immunoglobulin antibodies (Dimension Labs) followed by Supersignal™ Substrate (Pierce), as recommended by the manufacturer.

EXAMPLE 4

RNA-Binding Assay

Bacterial extracts from IPTG-induced cultures were separated on 10% SDS-polyacrylamide gels and the proteins transferred onto nitrocellulose membranes. Membranes were incubated in the presence of [$^{32}$P]-labeled RNA probes in 50 mM NaCl, 10 mM MgCl2, 10 mM Hepes, pH 8.0, 0.1 mM EDTA, 1 mM DTT, 0.25% milk, for 2 hr at room temperature, washed in the same buffer for 30 min, and exposed for autoradiography. For competition assays, an excess of cold homopolymers (Pharmacia) was added to the hybridization mixture along with the labeled probe. The 3'-UTR of bicoid cDNA (position 4016 to 4972) which was PCR-amplified from *Drosophila* genomic DNA, and subcloned in the bluescript™ vector, was transcribed using T7 RNA polymerase in the presence of [$\alpha$-$^{32}$P]CTP. Synthetic RNAs (Pharmacia) were labeled with T4 polynucleotide kinase in the presence of [$\delta$-$^{32}$P]ATP.

EXAMPLE 5

Tubulin-Binding Assay

Bacterial extracts from IPTG-induced cultures were separated on 10% SDS-polyacrylamide gels and the MBP-tagged proteins were transferred onto nitrocellulose membranes. Membranes were incubated in 10 mM Tris, pH 8.0, 150 mM NaCl (TBS) and 1% Tween 20 for 45 min prior to an overnight overlay with 7 mg/ml tubulin (Sigma) in TBS plus 0.2% Tween 20. Blots were washed several times in TBS plus 0.2% Tween 20, and then incubated with a mixture of mouse monoclonal anti-$\alpha$- and anti-$\beta$-tubulin antibodies (ICN). Bound antibodies were detected with secondary peroxydase-conjugated anti-mouse immunoglobulin antibodies (Dimension Labs) and Supersignal Substrate (Pierce), as stated previously. Separate assays were performed with actin and anti-actin antibodies (both from Sigma).

EXAMPLE 6

Immunofluorescence

Hstau/HA and hStau/GFP were constructed by PCR-amplification of the full-length cDNA using the primer pair 5'-TACATGTCGACTTCCTGCCA/GGGCTGCGGG-3' (SEQ ID NO:24) and 5'-TACAATCTAGATTATCAGCG-GCCGCACCTCCCACACACAGACAT-3' (SEQ ID NO:25). The 3'-primer was synthesized with a NotI site just upstream from the stop codon allowing ligation of a NotI cassette containing either three copies of the HA-tag or the GFP sequence. The resulting fragment was cloned in Bluescript following digestion with SalI and XbaI. The KpnI/XbaI fragment was then subcloned in the pCDNA3/RSV vector (Jockers et al., 1996) and a NotI-cassette was introduced at the NotI site. For the TBD/GFP fusion protein, the TBD was PCR-amplified with oligonucleotides on each side of this region (SEQ ID NO:26 5'-TACATAAGCTTAAGC-CACCATGGTCAAAGTTCC-CCAGGCGC-3') and (SEQ ID NO:27 5'-TACAATC-TAGAGCGGCCGCGCTCA-GAGGGTCTAGTGCGA-G-3'). The sense primer contained an ATG initiation codon and the Kozak consensus sequence, upstream from the TBD sequence. The anti-sense primer contained a NotI site, just upstream from a stop codon. The resulting fragment was digested with HindIII and XbaI and cloned into the pCDNA3/RSV vector. The GFP NotI-cassette was then introduced at the NotI site.

Mammalian cells were transiently transfected with the cDNAs by the calcium/phosphate precipitation technique, fixed in 4% paraformaldehyde in phosphate buffered-saline (PBS) for 25 min at room temperature and permeabilized with 0.3% Triton X-100 in PBS containing 0.1% BSA. The cells were then blocked with 1% BSA in PBS, 0.3% Triton X-100 and incubated with mouse anti-HA, rabbit anti-calreticulin or rabbit anti-calnexin antibodies for 1 hr at room temperature, as indicated. Cells were washed in permeabilization buffer and incubated with fluorescein-conjugated or Texas-Red-conjugated species-specific secondary antibodies (Jackson Immunoresearch Laboratories, West Grove, Pa.) in blocking buffer for 1 hr. GFP and GFP fusion proteins were detected by autofluorescence. Mounting was done in ImmunoFluor Mounting Medium (ICN). For the analysis of cytoskeleton-associated proteins, transfected cells were first extracted in 0.3% Triton X-100, 130 mM HEPES (pH 6.8), 10 mM EGTA, 20 mM MgSO4 for 5 min at 4 C, as previously described (Davis et al., 1987). They were then fixed in 4% paraformaldehyde in PBS and processed for immunofluorescence as described above. Cells were visualized by immunofluorescence using the 63× planApochromat objective of a Zeiss Axioskop fluorescence microscope.

Confocal microscopy was performed with the 60× Nikon Plan Apochromat objective of a dual channel BioRad 600 laser scanning confocal microscope equipped with a krypton/argon laser and the corresponding dichroid reflectors to distinguish fluorescein and Texas Red labeling. No overlap was observed between the fluorescein and Texas Red channels. Confocal images were printed using a Polaroid TX1500 video printer.

EXAMPLE 7

Molecular Cloning of Mammalian Staufen cDNAs

In order to understand the mechanism of mRNA transport in mammalian cells, the human and mouse staufen homologues was cloned. Thirteen overlapping human cDNAs, ranging in size between 0.8 and 2.5 kb, were isolated from a human central nervous system cDNA library, using the expressed sequence tag (EST) HFBDQ83 cDNA as a probe (FIG. 1A). Purified human HeLa cell poly(A)+ RNAs were also reverse transcribed and PCR-amplified using different 5'-RACE protocols, allowing the cloning of the 5'-end of the transcript. Two different cDNAs of 3217 and 3506 nucleotides were identified from overlapping clones (see below). The presence of multiple transcripts in human cells was confirmed by RT-PCR experiments (not shown). One of the human cDNAs was then used to screen a foetal total mouse cDNA library under low stringency conditions, which led to the isolation of a full-length cDNA (mStau)(GB accession number: AF061942). The nucleic and amino acid sequences of mStau Is shown in FIG. 1C. The human and mouse proteins are 90% identical (98% similarity), as shown in the alignment of the sequences thereof (FIG. 1D).

Hybridization of a Human Multiple Tissues Northern Blot with a human cDNA reveals that hStau mRNA is found in every tested tissue (FIG. 2A), unlike the *Drosophila* staufen gene which is exclusively expressed in oocytes and in the CNS at the larval stage (St Johnston et al., 1991). The size of the cDNAs is close to that of the transcripts, which migrate on a Northern blot as an unresolved large band of around 3.6 kb.

EXAMPLE 8

A Differential Splicing Event Generates Two Human Staufen Proteins

Characterization of the human cDNAs revealed the presence of four types of transcripts which only differ by an insertion of 289 bp at position 324 (FIGS. 1A and 1B). Interestingly, this sequence introduces an ATG initiation codon upstream from the first one found in the short transcript (FIG. 1A). This suggests that two putative proteins of 63 and 55 kDa may be translated, with one protein exhibiting an 81 amino acid extension at its N-terminal extremity, as compared to the other protein. Using anti-hStau antibodies in western blot experiments, two protein bands of around 63 and 55 kDa in human cell extracts were observed (FIG. 2B). To determine whether the cDNAs could account for the presence of the two proteins, each of them was subcloned in an expression vector and expressed in mammalian cells. As seen in FIG. 2C, each cDNA gives rise to a single overexpressed protein which perfectly comigrates with the endogenous proteins.

To determine whether these transcripts are the products of differential splicing, genomic DNA was PCR-amplified with primers located on each side of the insert. The resulting fragments were cloned, and their extremities sequenced. Comparison of the genomic and cDNA sequences demonstrated that the DNA insert is carried on a single exon, and that typical splicing consensus sequences are present at each intron/exon junction (not shown).

Taken together, these results demonstrate that the human staufen gene produces two different transcripts by alternative splicing and exon skipping, and that the transcripts code for two highly homologous proteins which differ in their N-terminal extremities.

EXAMPLE 9

Comparison of the Mammalian and *Drosophila* Staufen Proteins

Figure 2:
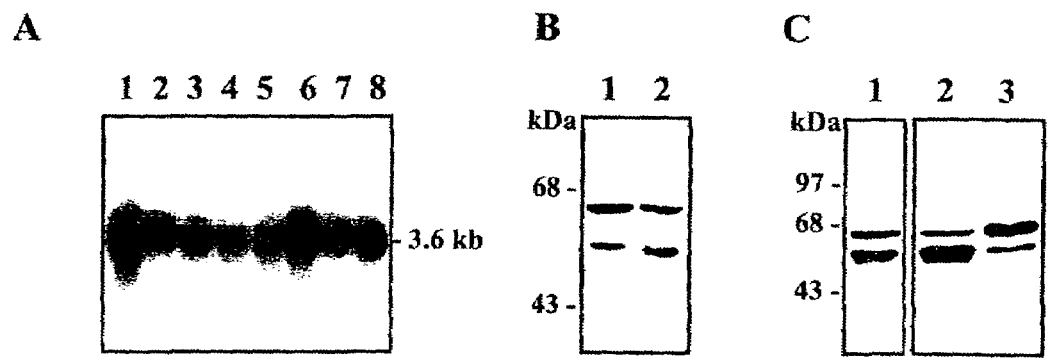
FIG. 2 shows the characterization of the hStau mRNA and proteins. A) Northern blot analysis of hStau expression in human tissues. A Human Multiple Tissues Northern Blot (Clontech) was hybridized with the 1.2 kbp BamHI fragment of hStau cDNA. Lane 1, brain; lane 2, pancreas; lane 3, heart; lane 4, skeletal muscles; lane 5, liver; lane 6, placenta; lane 7, lung; lane 8, kidney). B) Western blot experiment with anti-hStau antibodies. Lane 1, HeLa cell extracts; lane 2, HEK 293 cell extracts. C) HEK cells were transfected with cDNAs coding for either the short (lane 2) or the long (lane 3) hStau isoforms, lysed and analysed by western blotting using the anti-hStau antibodies. Mock-transfected cells are shown in lane 1. D) Schematic representation of the *Drosophila* (accession number M69111), mammalian and *C. elegans* (accession number U67949) staufen proteins. The human protein P1 has an insertion of 81 amino acids at its N-terminal extremity, as compared to protein P2. Large open and black boxes represent the full-length and short dsRNA-binding domains, respectively. Small boxes and lines are regions of high and low sequence similarity, respectively. The hatched boxes indicate the position of the region which is similar to the MAP1B microtubule-binding domain. The percentage of identity between the domains of the human and invertebrate proteins is indicated.
Figure 2:
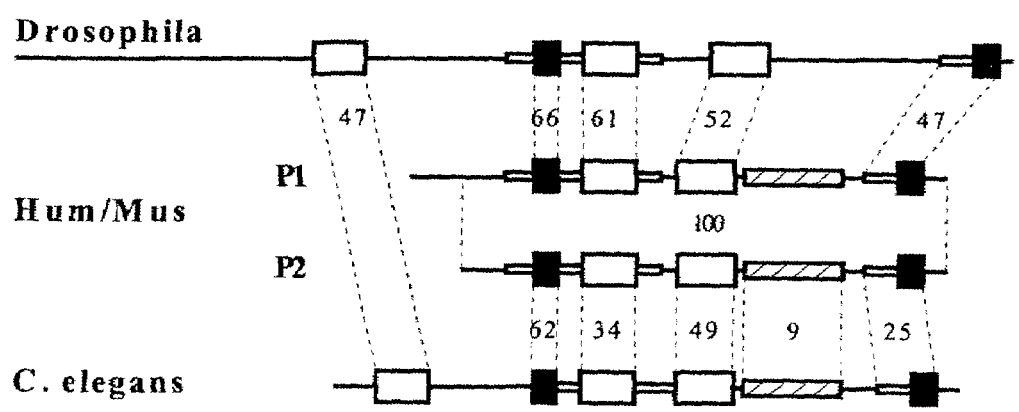

The amino acid sequences of the mammalian proteins are similar to that of the *Drosophila* staufen protein and of the product of an uncharacterized ORF on the X chromosome of *Caenorhabditis elegans* (FIG. 2D and FIG. 1'). The overall structure and relative position of the full-length and short-RBDs are well conserved and high sequence identity is found between corresponding dsRBDs. This is highly significant since an alignment of the domains found in the members of the dsRNA-binding protein family shows an average of only 29% amino acid identity to one another (St Johnston et al., 1992). In addition, domains 1 and 4 in the human sequence, which are short domains when compared to the consensus, are nevertheless highly similar to the corresponding fly sequences, even in the region that extends far beyond the N-terminal side of the consensus sequence, suggesting that they must play an essential role in staufen function.

Mammalian Stau does not contain the first dsRNA-binding domain nor the long N-terminal sequence of the *Drosophila* protein which was shown to bind to oskar protein (Breitwieser et al., 1996). In addition, a putative tubulin-binding domain located between the third and fourth dsRNA-binding domains of mammalian Stau is not found in the *Drosophila* protein, at least at the amino acid level. This region contains a stretch of 91 amino acids which show 25% amino acid identity (66% similarity) to a microtubule-binding domain of MAP1B (Zauner et al., 1992). It is meaningful that the sequence similarity covers the full microtubule-binding domain of MAP1B and that it is restricted to this domain.

EXAMPLE 10

The Human and Mouse Staufen Proteins Bind Double-Stranded RNAs

Figure 3:
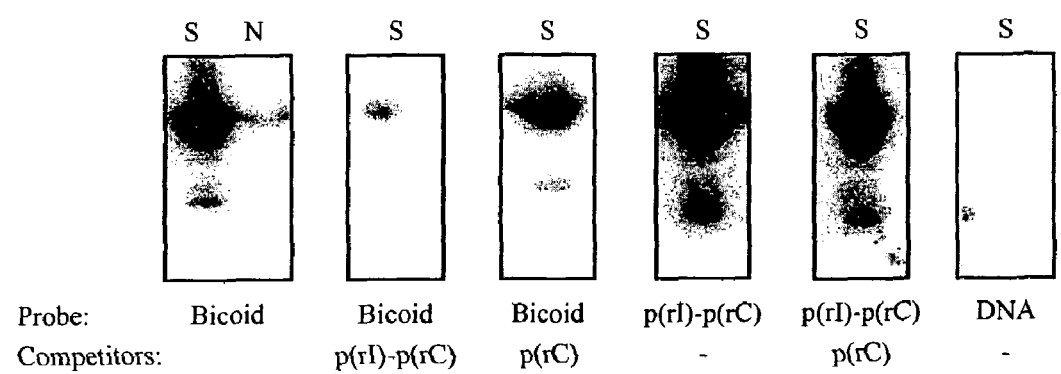
FIG. 3 shows an RNA-binding assay. A) Bacterially expressed his/hStau (lanes S) and his/NEP (lane N) fusion proteins or B) bacterially-expressed MBP/mStau (lanes S) or MBP/aminopeptidase fusion proteins (lane A), were electrophoresed on a polyacrylamide gel, transferred to nitrocellulose, and incubated with [32P]labeled nucleic acids, in the presence or absence of cold competitors, as indicated below each gel. After extensive washing, binding was detected by autoradiography.
Figure 3:
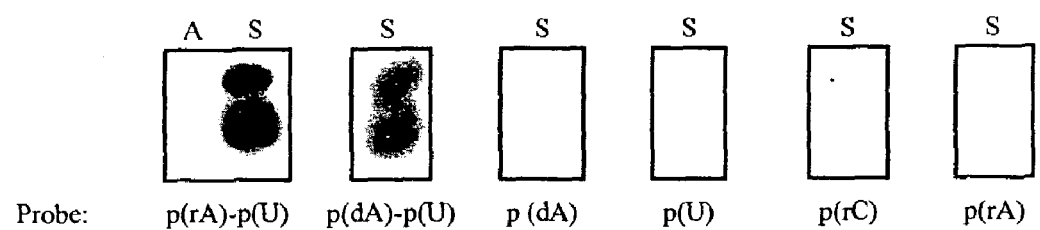

As seen in FIGS. 2D and 1', mammalian Stau proteins contain multiple dsRNA-binding domains. In order to determine whether Stau binds RNAs, two bacterially-expressed fusion proteins were used in an RNA-binding assay, his/hStau and MBP/mStau. The fusion proteins were probed with in vitro-labeled bicoid mRNA, which is known to adopt an extensive secondary structure and to strongly bind to the Drosophila staufen protein, both in vivo and in vitro (St Johnston et al., 1992; Ferrandon et al., 1994). Both fusion proteins strongly bind this RNA. The binding is competed by an excess of cold poly(rI)-poly(rC), but not by poly(rI), poly(rC), poly(rA) or poly(U), nor by tRNA or dsDNA (for example, see FIG. 3A), suggesting that mammalian Stau recognizes double-stranded structures in the RNA rather than a sequence-specific region. Both fusion proteins also directly bind labeled double-stranded RNAs and RNA/DNA hybrids, but not single-stranded RNA or DNA homopolymers (for example, see FIG. 3). As controls, a his/NEP (neutral endopeptidase) or MBP/aminopeptidase fusion proteins were also included on the blot; they did not bind any of these nucleic acids.

This demonstrates that both the human and mouse staufen proteins, regardless of the protein to which they are fused, are able to bind dsRNAs and RNA with extensive secondary structure, as reported for the Drosophila protein (St Johnston et al., 1992).

EXAMPLE 11

The Human and Mouse Staufen Proteins Bind Tubulin In Vitro

Figure 4:
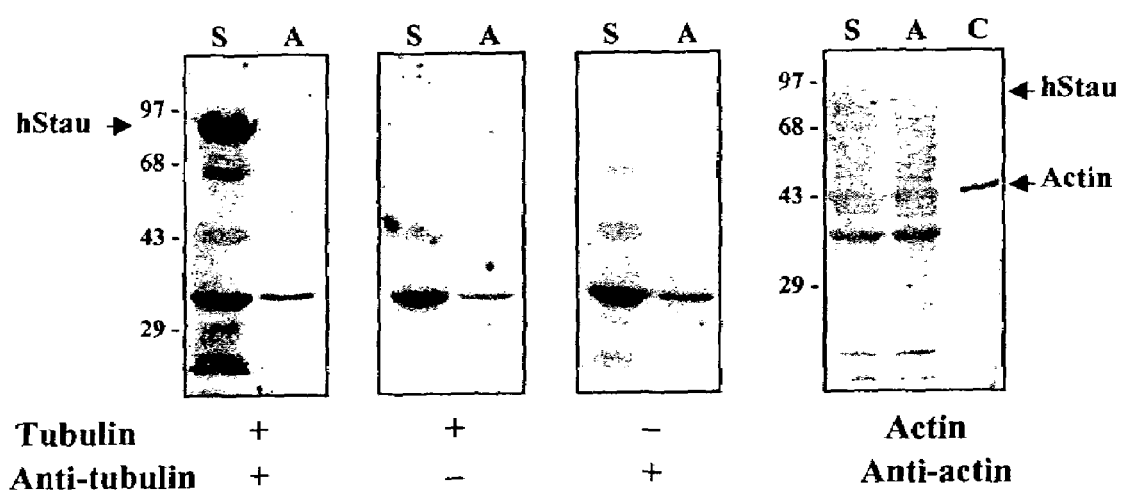
FIG. 4 shows a tubulin-binding assay. Bacterially expressed MBP/hStau (lanes S) or MBP/aminopeptidase (lanes A) fusion proteins were electrophoresed on SDS-polyacrylamide gels, transferred to nitrocellulose, and incubated with tubulin or actin. After extensive washing, tubulin and actin were detected with monoclonal anti-tubulin or anti-actin antibodies, respectively. As controls, the same experiments were also performed in the absence of either tubulin or anti-tubulin antibodies. Purified actin was also loaded on the gel as control (lane C).

As described above, Stau contains a region which is similar to the microtubule-binding domain of MAP-1B. To determine whether mammalian Stau can bind tubulin, bacterially-expressed MBP/Stau fusion proteins were used in a tubulin-binding assay. As shown in FIG. 4, hStau binds tubulin in vitro. As a control, the MBP/aminopeptidase fusion protein was also included on the blot; it did not show any tubulin-binding capability. Under the same conditions, hStau cannot bind actin (FIG. 4), which suggests that the binding of tubulin to staufen is specific. The same results were obtained with the MBP/mStau fusion protein (see FIG. 5B, lane 2). Binding to mRNAs and microtubules are two of the characteristics expected of localizing proteins, making hStau and mStau very good candidates for mRNA transport and localization in mammals.

EXAMPLE 12

Molecular Mapping of the RNA- and Tubulin-Binding Domains

Figure 5:
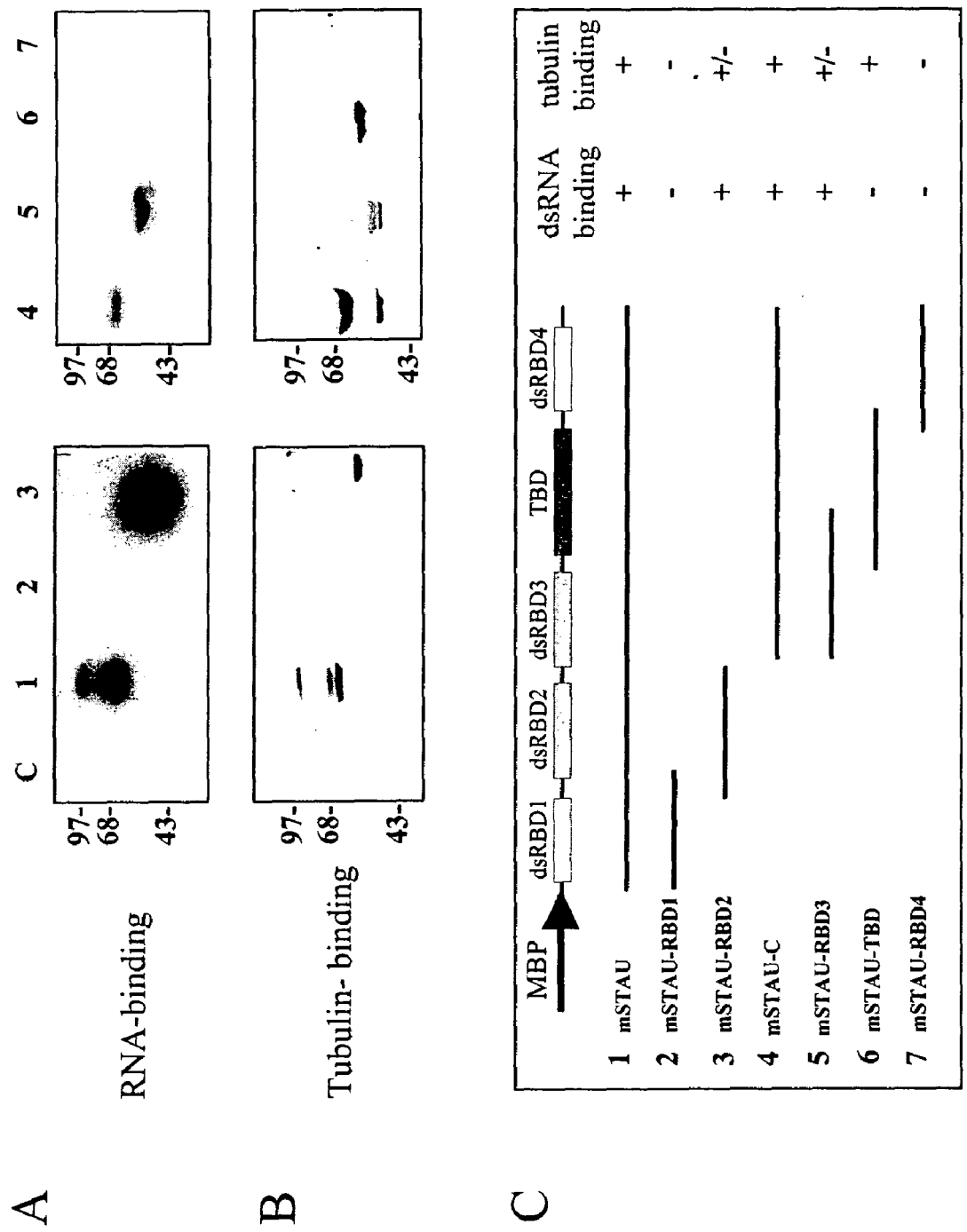
FIG. 5 shows a molecular mapping of the dsRNA- and tubulin-binding domains. Bacterially expressed MBP/mStau (lanes 1), MBP/mStau deletion mutants (lanes 2–7) or MBP/aminopeptidase (lanes C) fusion proteins were electrophoresed on a polyacrylamide gel, transferred to nitrocellulose, and incubated either with [32P]labeled 3'-UTR bicoid RNA (A) or tubulin and anti-tubulin antibodies (B), and revealed as described above. C) Schematic representation of the mutant proteins. Their RNA- and tubulin-binding responses are indicated.

To determine which staufen domain(s) is involved in RNA and/or tubulin binding, the MBP/mStau fusion protein was used to construct a series of deletion mutants (FIG. 5). The production and relative abundance of each fusion protein was first verified by Western blotting (not shown). Using the RNA-binding assay, it was demonstrated that both of the full-size dsRNA-binding domains (dsRBD2 and dsRBD3) are independently sufficient to bind bicoid RNA (FIG. 5A). In contrast, the two short-domains (dsRBD1 and dsRBD4) were unable to bind dsRNA in this assay. It was also demonstrated that the C-terminal half of mStau is able to bind tubulin (FIG. 5B, lane 4). More specifically, the region which is similar to the MAP1B-microtubule-binding domain is sufficient to bind tubulin (FIG. 5B, lane 6). The faint bands (FIG. 5B, lanes 3 and 5) were not reproducible.

These experiments confirm that the regions identified by sequence comparison as putative dsRNA- and tubulin-binding domains are biochemically functional.

EXAMPLE 13

Staufen is Associated with the Detergent-Insoluble Fraction In Vivo

Figure 6:
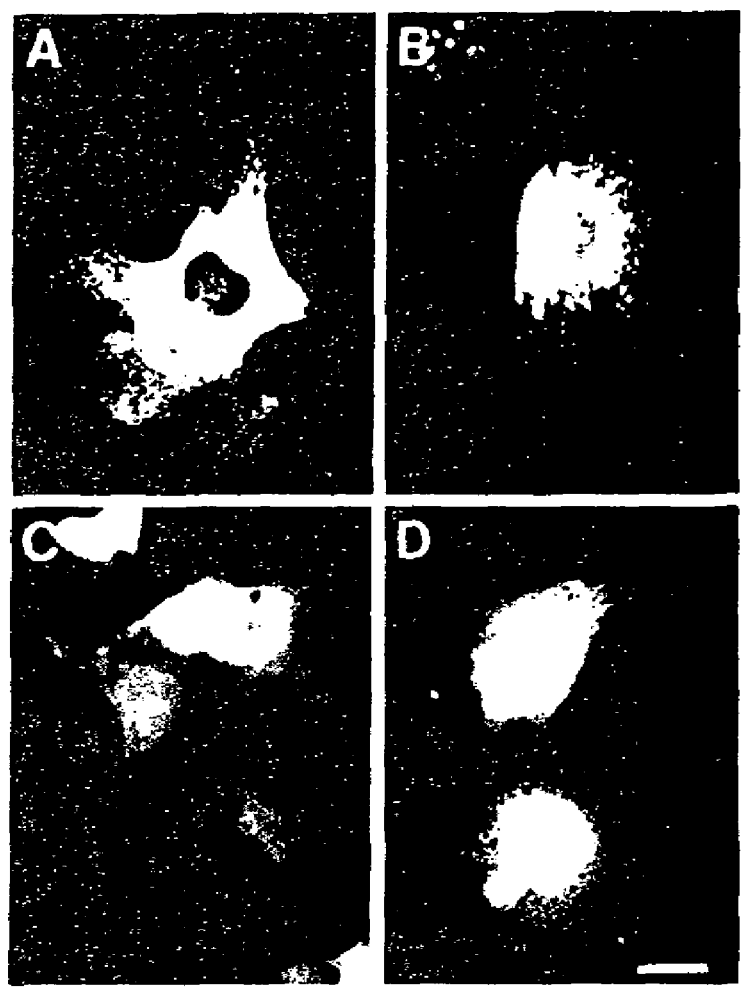
FIG. 6 shows a subcellular localization of the GFP/hStau fusion proteins. COS7 cells were transfected with cDNAs coding for either the hStau/GFP (A, B) or TBD/GFP(C) fusion proteins, or GFP alone (D). Untreated (A, C, D) or Triton X-100 treated (B) cells were fixed and visualized by autofluorescence. Bar=20 mm.

The cellular distribution and cytoskeletal association of the two human Stau proteins in vivo was then addressed. To do so, the Green Fluorescent Protein (GFP) or an HA-tag were fused to the 63 and 55 kDa hStau isoforms, respectively. Using confocal microscopy, it was first shown that the two fusion proteins co-localize when co-expressed in mammalian cells (not shown). Then, it was shown that they are non-homogeneously distributed throughout the cytoplasm and label numerous vesicular and tubular structures which concentrate in the perinuclear region (FIG. 6A). Minimal staining was found in the nucleus. When the cells were treated with Triton X-100 prior to fixing, allowing soluble proteins to be separated from the cytoskeleton and cytoskeleton-associated proteins (Pachter, 1992), the tubulovesicular labeling was still present, demonstrating that hStau is associated with the detergent-insoluble material in vivo (FIG. 6B). Labeled structures were also present in cell processes, suggesting that Stau may target mRNAs to peripheral ER elements. The same results were obtained following expression of the GFP/mStau protein (not shown). The association between hStau and the cytoskeletal-associated material was confirmed by in vitro cell fractionation in the presence of Triton X-100. In this assay, hStau partitioned mainly in the cytoskeleton-associated fractions, although a significant fraction was found in a soluble form, as judged by Western blotting (not shown).

To determine whether the tubulin-binding domain identified in vitro is truly involved in this function in vivo, mammalian cells were transfected with a cDNA coding for a fusion protein in which the minimal tubulin-binding domain was fused to GFP. In contrast to the full-length protein, the TBD/GFP fusion protein is randomly distributed in the cytoplasmic and nuclear domains of the cells (FIG. 6C), as is the GFP protein used as a control (FIG. 6D). This staining was completely extracted by the Triton X-100 treatment (not shown), suggesting that the minimal tubulin-binding domain found in vitro is not sufficient to render the protein insoluble and form a stable association with the microtubule network and/or the cytoskeleton-associated material.

EXAMPLE 14

Staufen Localizes to the Rough Endoplasmic Reticulum In Vivo

Figure 7:
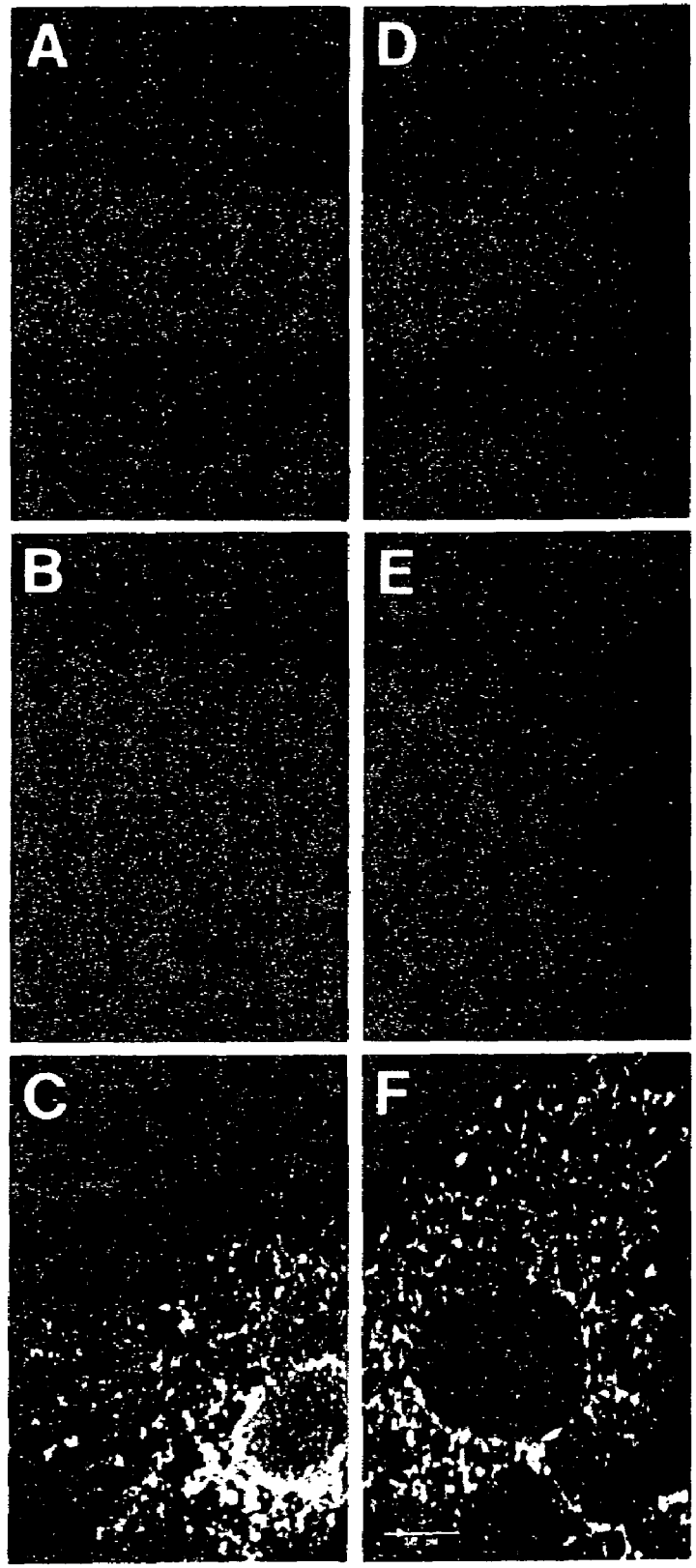
FIG. 7 shows a co-localization of hStau with markers of the rough endoplasmic reticulum (RER) using confocal microscopy. A cDNA coding for an hStau/HA fusion protein was transfected into COS7 cells. Triton X-100 treated cells were fixed and double-labeled with anti-HA (B) and anti-calreticulin (A) or anti-HA (E) and anti-calnexin (D). Anti-HA was detected with Texas Red-coupled anti-mouse IgG antibodies using the Texas Red channel, whereas anti-calreticulin and anti-calnexin were detected with fluorescein-conjugated anti-rabbit IgG antibodies, using the fluorescein channel. C and F are the superposition of A-B and D-E, respectively. No overlap was observed between the fluorescein and Texas Red channels. Bar=10 mm.

Interestingly, the pattern of localization of Stau resembles that of the endoplasmic reticulum. To test a putative localization of Stau to the ER, mammalian cells were transfected with a cDNA coding for a fusion protein in which a HA-tag was introduced at the C-terminal end of the short hStau protein. The cells were then double-labeled transfected with anti-HA, to recognize hStau, and with anti-calreticulin or anti-calnexin, two markers of the ER. Using a confocal microscope, it was shown that hStau completely co-localizes with anti-calreticulin, although HA-staining appears to be absent in some parts of the ER, in particular around the nucleus (FIGS. 7A–C). To confirm these results, the co-localization of staufen and calnexin, a specific marker for the RER (Hochstenback et al., 1992)(FIGS. 7D–F) was examined. The patterns of staining obtained with anti-hStau and anti-calnexin were identical, demonstrating that hStau co-localizes exclusively with the RER.

EXAMPLE 15

Implication of Staufen in mRNA Transport and Localization

The transport and localization of specific mRNAs have important functions in cell physiology. For example, mRNA targeting plays a key role in the formation of cytoskeletal filaments and in the establishment of morphogenetic gradients (St Johnston, 1995). However, the nature of the ribonucleoprotein complexes as well as the mechanisms involved in these processes are still largely uncharacterized. Herein, a novel RNA-binding protein which localizes to the rough endoplasmic reticulum in mammalian cells has been described. Although its precise role is still unclear, its biochemical and molecular properties strongly suggest that it is involved in mRNA transport and/or localization. Consistent with such a role, we recently demonstrated that hStau is involved in RNA virus encapsidation and more particularly in HIV-1 genomic RNA encapsidation (see below). Similarly, a mammalian staufen homologue was recently shown to be involved in the polarized transport of mRNAs in hippocampal neurons (Kiebler et al., submitted).

EXAMPLE 16

Structure/Function of Staufen

As is the case for all members of the dsRNA-binding protein family (St Johnston, 1995), it was observed that mammalian staufen can bind any dsRNA or RNAs forming extensive secondary structures in vitro, regardless of its primary sequence, as well as RNA/DNA hybrids. The latter adopt a conformation that is more closely related to that of dsRNA than dsDNA, which probably explains why they can bind to staufen. The fact that the full-length Stau protein, as observed with single dsRBD, binds to any dsRNA in vitro, suggests that the correspondence between the position of the dsRNA-binding domains and the arrangement of double-stranded stems in the folded RNAs may not be sufficient for specificity; post-translational modifications and/or essential co-factors capable of forming complex ribonucleoprotein structures along with mRNA molecules, could be necessary to discriminate between different RNA secondary structures. Packaging of mRNAs into ribonucleoprotein complexes (Ainger et al., 1993; Ferrandon et al., 1994; Forristall et al., 1995; Knowles et al., 1996), the intermolecular dimerization of the localization signal of bicoid mRNA (Ferrandon et al., 1997) and the involvement of untranslatable hnRNAs in mRNA transport (Tiedge et al., 1991; Tiedge et al., 1993; Kloc and Eskin, 1994), are consistent with this interpretation. Until now, specific mRNA/staufen interactions were only shown in vivo after injection of different RNAs into Drosophila embryos, but the mechanisms underlying the specificity are not known (Ferrandon et al., 1994). Since specific RNA binding cannot be obtained in vitro, it precludes the use of classic techniques to isolate and identify relevant RNAs which would bind staufen in vivo. Cross-linking of mRNA to staufen in vivo, and isolation of the resulting complexes will be necessary to identify the nature of bound RNAs.

Regardless of their limitations, the in vitro assays did allow a mapping of the molecular determinants which are necessary and sufficient to bind RNAs. The presence of two functional domains in the mammalian Stau contrasts with what has been reported for other members of the dsRNA-binding protein family, which contain multiple full-length dsRBDs, but only one that is biochemically functional (Gatignol et al., 1993; McCormack et al., 1994; Schmedt et al., 1995; Krovat and Jantsch, 1996). Interestingly, full-length dsRBDs incapable to bind dsRNA by themselves can do so when joined to another inactive full-length domain, suggesting that multiple domains present in a given protein exhibit cooperative binding effect (Schmedt et al., 1995; Krovat and Jantsch, 1996). Whether the two mStau dsRNA-binding domains exhibit similar or different affinities is not yet clear. However, the identification of the molecular determinants of staufen necessary and sufficient for RNA binding open the way to a wide variety of utilities. Non-limiting examples include viral therapy and prevention, targeting of molecules (comprising staufen's incorporation domain) into virions and gene therapy. In this respect, the PCT publication of Cohen et al. WO 96/07741 is of relevance, as it identified a new means for targeting molecules into HIV virions. The teachings of WO 96/07741, including vpr/vpr fusion proteins, vpr/vpr recombinant proteins and nucleic acid molecules encoding same can be applied to the present invention, now that staufen has been identified as a RNA-virus targeting protein and more particularly as a HIV targeting protein.

Tubulin-binding domain was mapped to a region which is similar to a microtubule-binding domain of MAP1B. Although this region can efficiently bind tubulin in vitro, it is not sufficient to bring a TBD/GFP fusion protein to the microtubule network. Binding of Stau to microtubules in vivo may involve more than one molecular determinant or the proper localization and folding of the TBD in the full-length protein. Indeed, in our in vitro assay, the fusion protein which contains the C-terminal region in addition to the TBD binds tubulin more efficiently than does the TBD, alone, suggesting that this region may be necessary for binding to microtubules in vivo. Interestingly, the corresponding region of the Drosophila staufen protein was shown to bind inscutable (Li et al., 1997), a protein with ankyrin domains which is believed to associate with the cytoskeleton (Kraut and Campos-Ortega, 1996), suggesting that corresponding regions of the mammalian and Drosophila proteins may have functional similarities. The characterization of the mammalian staufen can therefore provide a guidance for a broadering of the present teachings to lower eukaryotic staufen such as that of Drosophila and as of C. elegans.

Alternatively, binding may be weak and/or transitory in vivo, for example during the early steps of mRNA recruitment, during mRNA transport and/or at mitosis, as reported in Drosophila (Ferrandon et al., 1994; Pokrywka and Stephenson, 1995; St Johnston, 1995). These steps may be difficult to observe by immunofluorescence (Ferrandon et al., 1994), and/or be masked by the anchoring of the protein to the RER. These steps may nevertheless be necessary to allow efficient and flexible transport of RNA along the cytoskeleton. In Drosophila, there is no evidence that staufen directly binds to the microtubule network, although staufen-dependent mRNA transport was shown to rely on this structure (Pokrywka and Stephenson, 1995; St-Johnston, 1995). A similar conclusion was reached when binding of MAP1B to the microtubule network was studied (Zauner et al., 1992), suggesting that weak binding to the cytoskeleton may be a characteristic of proteins containing this type of tubulin-binding domain.

The present teachings demonstrate that Stau is anchored to the RER and that the putative TBD is not involved in this function. Indeed, preliminary results suggest that the binding of Stau to RER is carried out by one of the RNA-binding domains (data not shown). Similar domains in other members of the dsRNA-binding proteins were previously shown to be involved in protein dimerization and/or in protein/protein interactions (Cosentino et al., 1995; Benkirane et al., 1997). This also suggests that different Stau molecular determinants are necessary for binding to tubulin and anchoring to the RER. This is consistent with previous observations in *Xenopus* and *Drosophila* that demonstrated that mRNA localization was likely to occur via successive steps involving different elements of the cytoskeleton and overlapping molecular determinants (St Johnston, 1995).

EXAMPLE 17

Localization of Staufen to the RER

When expressed in mammalian cells, Stau isoforms show a tubulovesicular pattern of localization which is found more abundantly in the perinuclear region. Stau is the first RNA-binding protein shown to be associated with the RER in mammals. No signal peptide or putative hydrophobic transmembrane domains are present in either the long or short staufen proteins, indicating that they are cytosolic proteins and not residents of the RER and that their association to the RER is likely to reflect their mRNA transport function. Two recent papers also suggest that mRNA transport may be linked to the endoplasmic reticulum or ER-like structures. In *Xenopus* oocytes, vera, a Vg1 mRNA binding protein, was shown to co-sediment with TRAPa, a protein associated with the protein translocation machinery of the ER. However, in contrast to Stau, vera/Vg1 complexes were found associated only with a small subdomain of the ER, which was of the smooth variety (Deshler et al, 1997). Similarly, in *Drosophila*, at least some steps in mRNA transport in nurse cells and oocytes seem to occur within ER-like cisternae (Wilsch-Bräuninger et al., 1997). As observed for the Vg1 mRNA/SER interaction in *Xenopus*, this structure seems to exclude most ribosomes, suggesting that translation is not the major function of these associations.

Hstau and mStau represent new members of a large family of proteins involved in the transport and/or localization of mRNAs to different sub-cellular compartments and/or organelles. Stau, TRBP/Xlrbpa and Spnr were shown to co-localize with RER (see above), with ribosomes and heterogenous nuclear RNPs (Eckmann and Jantsch, 1997), and with the microtubular array of spermatids (Schumacher et al., 1995), respectively. The present results strongly suggest that staufen/mRNA ribonucleoprotein complexes are transported along the microtubule network and then anchored to the RER. It is well known that the ER is associated with the microtubule cytoskeleton (Terasaki et al., 1986). Therefore, a transient interaction between microtubules and Stau may facilitate the localization of Stau and the targeting of mRNA to the RER. One of the roles of Stau might be to transport and localize specific mRNAs to the RER, such as those coding for secreted or membrane proteins which have to be translocated to the RER. This would bring them in proximity to the signal recognition particles (SRP) and RER, thus facilitating translation and translocation. The presence of Stau in cell processes, in association with ER structures, may represent a first clue to understanding the role of many mRNAs coding for neuropeptides, receptors or ion channels which were found to be localized in neuronal processes (Steward, 1997). Stau may facilitate the transport of mRNAs to cell processes to ensure efficient local translation and translocation. In addition, the presence of multiple staufen-like proteins in mammals creates the possibility that different members of the family could target sub-classes of mRNAs to different sub-domains of the ER. This phenomenon has been described before, and is thought to be the first step in the differential targeting of proteins in polarized cells (Okita et al., 1994).

The possibility that staufen plays additional roles in mammals is not excluded; Stau may first be linked to the RER for storage, then a subset of molecules may be recruited by specific mRNAs and/or cofactors to form ribonucleoprotein complexes that will be transported along microtubules toward their final destination. Consistent with this possibility is the presence of large amounts of Stau in the perinuclear region, where it may await the nucleo-cytoplasmic transport of mRNAs. Alternatively, Stau may play key roles in the regulation of translation of localized mRNAs. The fact that *Drosophila* staufen is essential for the translation of oskar mRNA, once it is localized at the posterior pole, is consistent with this hypothesis (Kim-Ha et al., 1995). Characterization of mRNAs and putative cofactors which bind to staufen will be necessary to understand the process.

In vertebrates, the mechanisms which underly the transport of mRNAs have not yet been deciphered. Characterization of the RNAs and proteins involved in transport and localization is particularly important since understanding the mechanisms responsible for the transport of mRNAs is fundamental for learning more on the development of polarity in cells, both during mammalian development and in somatic cells, at a time where RNA-based gene therapy is being considered as a possible approach to cure different disorders.

The present invention therefore opens the way to a development of better strategies for RNA-based gene therapy.

EXAMPLE 18

Staufen is Incorporated into HIV-1 Virions

Figure 8:
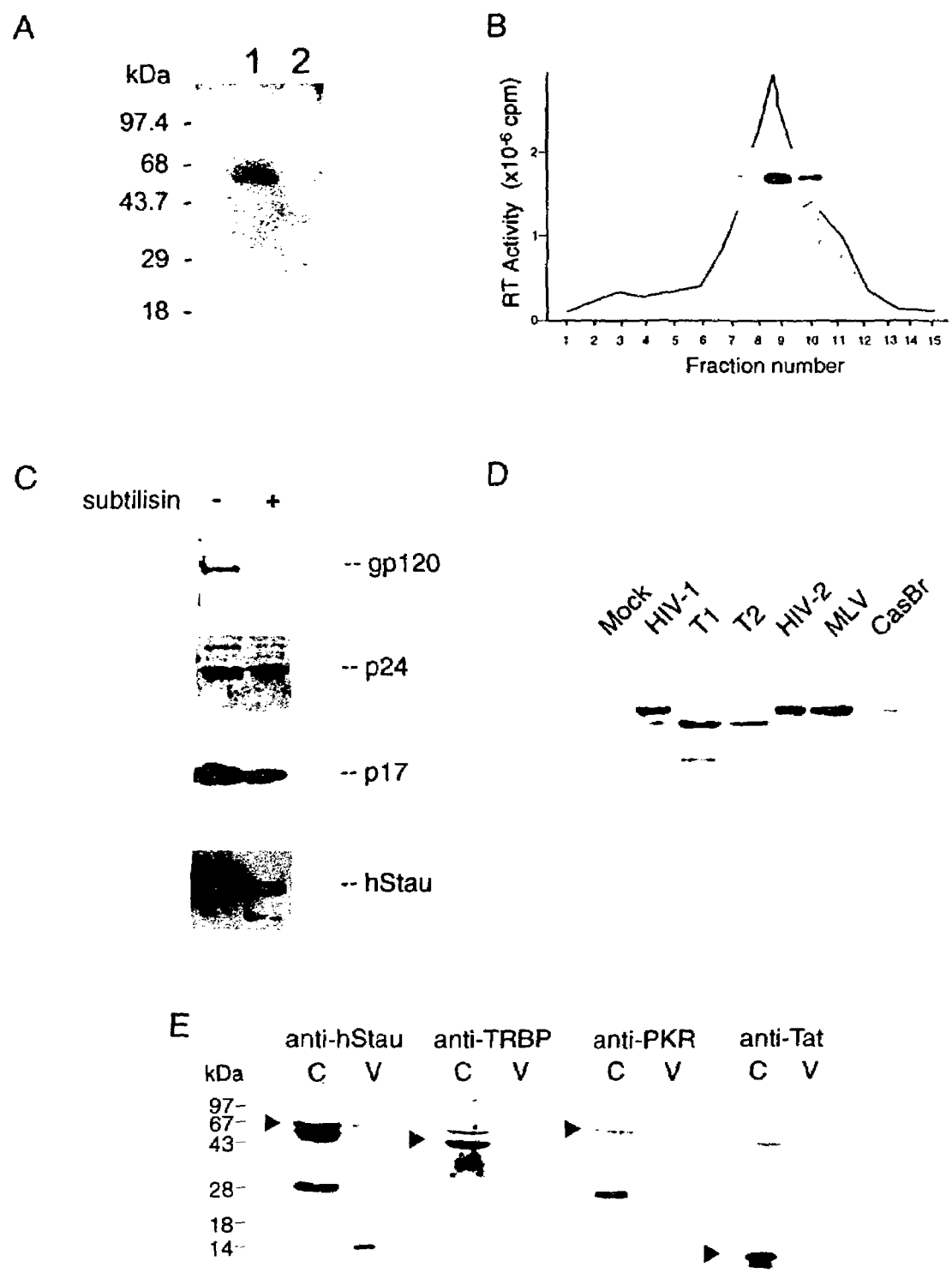
FIG. 8. A. Northwestern analysis of hStau TAR RNA-binding. Extracts of bacteria expressing either histidine(his)-tagged hStau (lane 1) or his-NEP (neutral endopeptidase, lane 2) fusion proteins were electrophoresed on a polyacrylamide gel (PAGE), transferred to nitrocellulose and incubated for 2 h with a uniformly [$^{32}$P]labelled TAR(1–80) RNA in 50 mM NaCl, 10 mM $MgCl_2$, 10 mM Hepes, pH 8.0, 0.1 mM EDTA, 1 mM DTT, 0.25% milk. After extensive washing, the membrane was exposed to autoradiographic film. B. Sucrose density gradient analysis of hStau in HIV-1. $50 \times 10^6$ cpm of microfiltered and ultracentrifuged virus HxBru was layered onto a continuous 20–60% sucrose gradient, ultracentrifuged at 136 000×g for 16 h. 16–0.7 mL fractions were collected and RT activity was measured by standard assay. Each fraction was subsequently diluted to 20% sucrose and centrifuged at 136 000×g for 1 hr to pellet virus particles. After rinsing, the virus pellet was resuspended in PBS and 2× Laemmli loading buffer was added before loading onto a 10% PAGE. The proteins were transferred to nitrocellulose and probed with a rabbit anti-hStau antibody. hStau was visualized using the enhanced chemiluminescence (ECL) kit (Amersham, Mississauga, ON). C. Subtilisin protease resistance assay. Subtilisin assays were performed essentially according to Ott et al., (9, 10) with minor modifications. $70 \times 10^6$ cpm of pelletted virus preparations were treated (+) or mock treated (−) with 1 mg/mL subtilisin (Boehringer Mannheim, Montreal, PQ) in 10 mM Tris-HCl, pH 8, 1 mM $CaCl_2$, containing 1.5 mg/mL bovine serum albumin (ICN Biochemicals, Montreal, PQ) for 24 h at 37° C. Virus was then pellefted as above and resuspended in PBS, and made to 1× Laemmli and then loaded onto PAGE followed by Western blotting. The blot was sequentially probed with anti-gp120 (32), a mouse monoclonal antibody #3H11-C1 to p17 (33), a human patient's serum (#162) to reveal p24, and anti-hStau. D. hStau incorporation into virus particles from clinical isolates and the retroviruses HIV-2, MLV, and CasBr. 293T cells were transfected with proviral constructs encoding HIV-1, HIV-2 (ROD), MLV (kindly provided by Dr. Guy Lemay, University of Montreal) and CasBr retroviruses (11). Virus (passage # 2) was also harvested following infection of MT4 cells with two T-tropic viral clinical isolates (T1 & T2; a kind gift from Dr. Mark Wainberg, McGill AIDS Center). $10 \times 10^6$ RT cpm (HIV-1, HIV-2 and MLV) were loaded onto gels and incorporated hStau was assessed by Western blotting. The 55 and 63 kDa hStau species are due to translation initiation from alternatively spliced transcripts (5). Longer exposures reveal both species in all lanes. E. hStau is the only TAR-binding protein to be virion incorporated. Three sets of 25 000 293T cell equivalents (C) and 50 ng p24 virus equivalents (V) were run in parallel on 10% PAGE and each of three blots was probed with antibodies to hStau, TRBP (kindly provided by Dr. Sundararajan Venkatesan, NIAID), and PKR (kindly provided by Dr. Antonis Koromilas, McGill University). For the assessment of Tat in virus particles, 293T cells were transfected with pNL4.3 and at 48 h postinfection (p.i.) cells were lysed in Laemmli buffer and 25 000 cell equivalents were run in parallel with 50 ng p24. An amino-terminal anti-peptide Tat antibody was used for Western blot analysis. Antigens were revealed by ECL and are indicated by bold arrowheads. TRBP, PKR and Tat were undetectable in virion preparations in longer exposures of Western blots.

In order to assess the functional significance of the dsRNA-binding activity of staufen in mammalian cells, the possibility of its binding to the TAR sequence in the HIV-1 RNA leader was investigated (FIG. 8A). Its association with HIV-1 was further investigated by determining whether hStau was incorporated into HIV-1 particles, a possible result of its double-stranded RNA binding capacity. Indeed, using a polyclonal antiserum generated to highly purified recombinant hStau, the corresponding 55 and 63 kDa species (5) of staufen were identified in purified viral preparations of laboratory strains of HIV-1 HxBc2 (HxBru, HxBH10) and pNL4.3, and in vesicular stomatitis virus G (VSVG) envelope pseudotyped HIV-1 particles (data not shown and FIG. 8) generated in human T lymphocyte (MT4 and Jurkat) or epithelial (293T) cell lines (data not shown).

To further substantiate hStau virion incorporation, sucrose gradient analyses were performed. First, microfiltered and ultracentrifuged HxBru virus was prepared in 293T cells. This cell type produces negligible amounts of contaminating microvesicles that contain cellular proteins (8). The virus was fractionated in a 20–60% sucrose gradient, and the presence of hStau in each fraction was evaluated by Western blot analysis. hStau was found to cosediment with reverse transcriptase (RT) activity, strongly indicating incorporation or strong association with viral particles (FIG. 8B). To further support virion incorporation, a subtilisin protease assay was performed on virus preparations (9). While envelope glycoprotein gp120 was completely degraded as expected after subtilisin treatment, viral proteins p24 and p17 remained in large part protected since they are found within the virus (FIG. 8C). hStau also remained intact (FIG. 8C), though there appeared to be some degradation by subtilisin treatment. This same phenomenon was recently observed in virus generated in H9 and CEM cells where an actin isoform was shown to be incorporated within HIV-1 particles while some of the protein was also sensitive to subtilisin treatment (10).

Incorporation of hStau in two T-tropic viral clinical isolates minimally passaged in MT4 cells, and in three other retroviruses, HIV-2, murine leukemia virus (MLV) and Casitas brain ecotropic MLV (CasBr; 11) was then examined. All of these vector viruses incorporated hStau (FIG. 8D) suggesting a common functional role. Of note, hStau was also shown to be incorporated into a non retrovirus RNA virus, Reovirus (data not shown). Purified cell-free preparations of the DNA viruses, adenovirus, Epstein Barr virus (EBV) and human herpesvirus 6 (HHV-6) did not contain hStau. The presence of hStau was evaluated in concentrated cell-free and cesium chloride-banded preparations of Adenovirus (kindly provided by Dr. Bernard Massie, Biotechnology Research Institute, Montreal, Quebec), EBV and HHV-6 (both kindly provided by Drs. Ali Ahmad and José Menezes, Department of Microbiology and Immunology, University of Montreal). hStau was assessed by Western blot analysis: there were no detectable bands corresponding to hStau in up to 20×10 viral particles.

While hStau is incorporated into virions, the dsRNA- and TAR RNA-binding proteins TAR RNA-binding protein (TRBP), dsRNA-activated protein kinase (PKR) and Tat, are not detectable in purified preparations of HIV-1 (FIG. 8E). Taken together, these data show that the TAR-binding activity is not sufficient to enable virion incorporation.

Figure 9:
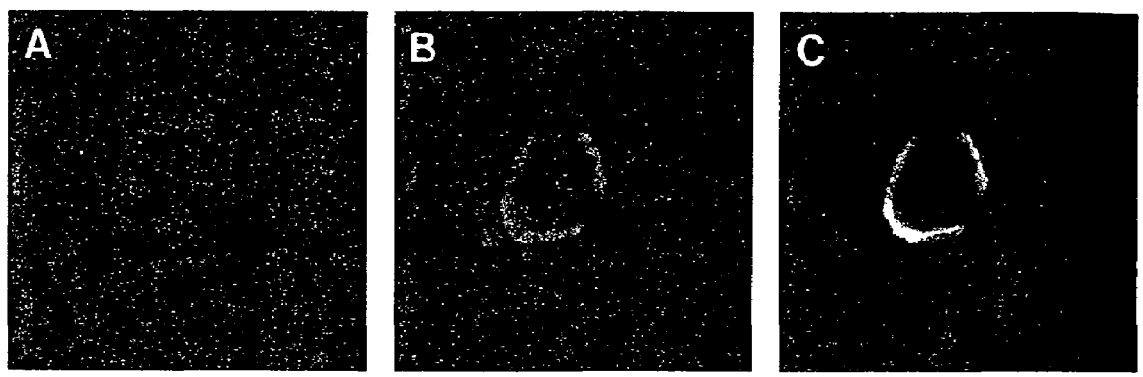
FIG. 9 shows a localization of hStau in cotransfected 293T cells by confocal laser scanning microscopy. 293T cells were cotransfected with pNL4.3 and a plasmid encoding a HA-tagged hStau (5). 36 h posttransfection, cells were trypsinized and plated on glass slides and allowed to grow for 12 h. After washing, cells were fixed with acetone: methanol (50:50) and allowed to dry. Indirect immunofluorescence was performed using a mouse anti-HA monoclonal (12CA5, Boehringer Mannheim) and a rabbit anti-p24 (34). Texas Red- and fluorescein-conjugated secondary antibodies were employed to reveal p24 and HA-hStau, respectively. Confocal laser scanning microscopy was performed using a Zeiss LSM410 microscope with excitation wavelengths of 488 nm and 568 nm for fluorescein and Texas Red, respectively. Emission filters for fluorescein and Texas Red were BP515-540, and BP575-640, respectively. p24 (A), hStau (B), and superimposed images (C) are presented. The yellow regions indicate colocalization of p24 and hStau (mostly at the cell periphery). A representative cell is shown.

Confocal laser scanning microscopy was employed to determine the precise localization of hStau in HIV-1-producing cells. pNL4.3 and a hemagglutinin (HA)-tagged hStau were coexpressed in 293T cells and p24 and hStau were visualized by Texas Red- and fluorescein-conjugated secondary antibodies, respectively, in indirect immunofluorecence analyses (FIG. 9). hStau showed a diffuse cytoplasmic staining (5) and a large proportion of hStau was found to be colocalized with p24 antigen at the cell periphery (FIG. 9C). This colocalization is suggestive that hStau is present at sites of virus assembly, consistent with its presence in virions.

EXAMPLE 19

Characterization of Molecule Determinants, Involved in Staufen Incorporation into HIV-1

Figure 10:
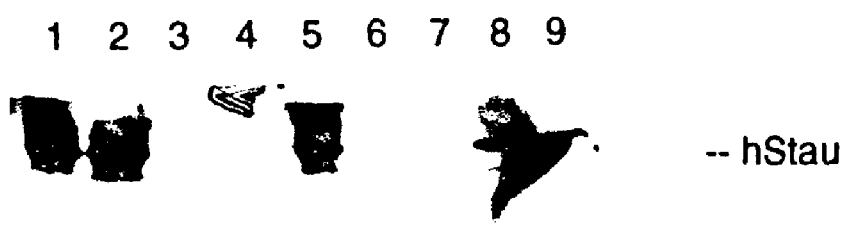
FIG. 10 shows hStau incorporation correlating with genomic RNA encapsidation in HIV-1 particles. Proviral DNAs [(wildtype, NC (14, 15), vpr− or vpr+ (6) and psi mutants (16)] were transfected into 293T cells and equal quantities of virus were loaded onto 12% PAGE and probed with anti-hStau (A) and anti-p17 (B; 33) antisera and antigens were revealed by ECL. In C, RNA was isolated from equal quantities of virus using an NP-40 lysis method (35) and probed with a [$^{32}$P]-labelled probe to the Gag mRNA leader (6). Lane 1, pNL4.3; lane 2, HxBru; lane 3, $^{28}$C/$^{49}$C-S NC; lane 4, $^{15}$C/$^{18}$C-S NC; lane 5, $^{36}$CP$^{39}$C-NC; lane 6 delta $^{14}$K-$^{50}$T NC; lane 7, psi signal mutant; lane 8, HxBru Vpr− provirus; lane 9, HxBru Vpr+ provirus.
Figure 10:
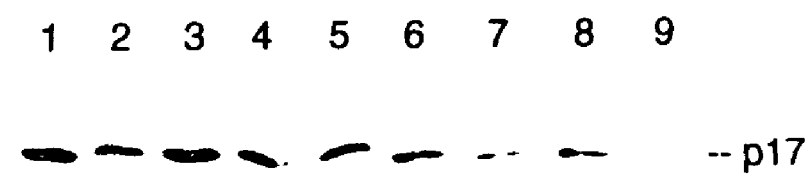
Figure 10:
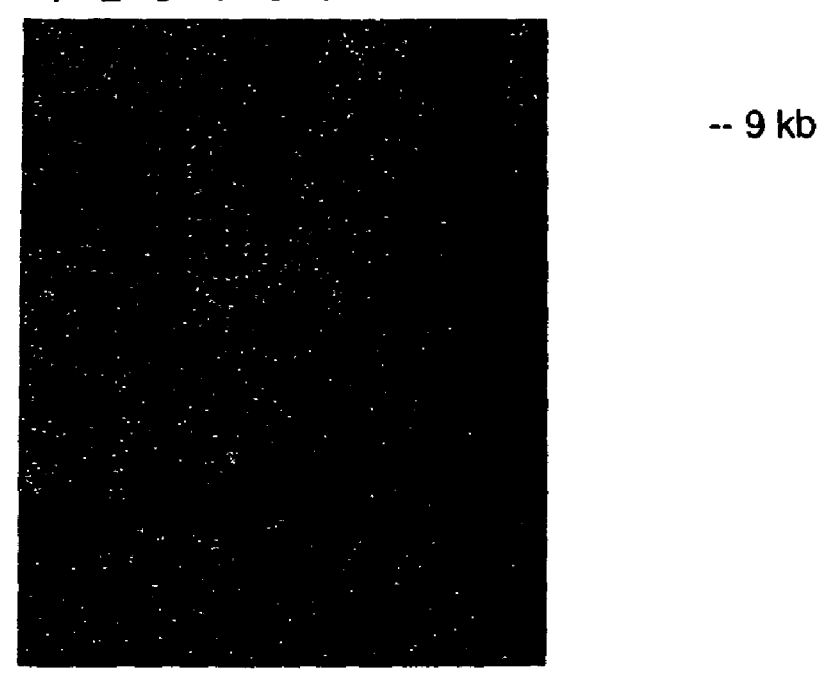

On the basis of hStau TAR RNA-binding and its virion incorporation, a role for hStau in virus assembly was investigated. It was therefore attempted to correlate genomic RNA encapsidation with hStau incorporation in HIV-1. Transfection of wildtype provirus DNAs yields virus particles containing comparable amounts of hStau (FIG. 10, lanes 1 & 2). Genomic RNA encapsidation in HIV-1 is primarily mediated through the association of the packaging (psi) domain in the 5' leader sequence with the nucleocapsid (NC) protein (13). Therefore, an HIV-1 molecular clone HxBru in which the $^{28}$Cys and $^{49}$Cys of NC were mutated to Ser ($^{28}$C/$^{49}$C-S; 14) was initially tested. It was found that hStau incorporation was drastically reduced in these virus preparations (cf. FIG. 10, lane 3). Several other HIV-1 proviruses with NC mutations and deletions (15), and a psi domain deletion mutant (16) were then tested, most of which generate noninfectious virus particles that are significantly impaired in RNA encapsidation. With the exception of the $^{35}$C/$^{39}$C-S NC mutant, transfection of all NC and psi mutant DNA proviral constructs generated virus particles that contained negligible amounts of hStau. Genomic RNA encapsidation was assessed in Northern blots and these analyses revealed that the psi and NC mutant constructs yielded virus with drastically reduced levels of genomic 9 kilobase pair (kb) RNA. In the $^{36}$C/$^{39}$C-S NC mutant virus preparation (FIG. 10, lane 5) hStau is present at approximately wildtype levels, and at the same time near wildtype levels of genomic RNA encapsidation are observed, consistent with several earlier observations (17). hStau incorporation into HIV-1 particles is thus strongly correlated with genomic RNA encapsidation. Consequently, hStau may indeed sort viral RNAs into a vicinity of an infected cell where Gag proteins are present, during assembly of virus particles. Alternatively, the data presented herein suggest that hStau incorporation is mediated through both the psi and NC domains; and with the recent structural characterization of NC-psi binding (18) it will be interesting to determine whether hStau is necessary for this conserved and critical association.

EXAMPLE 20

Incorporation of Staufen into HIV-1 Virions Decreases the Infectivity Thereof

Figure 11:
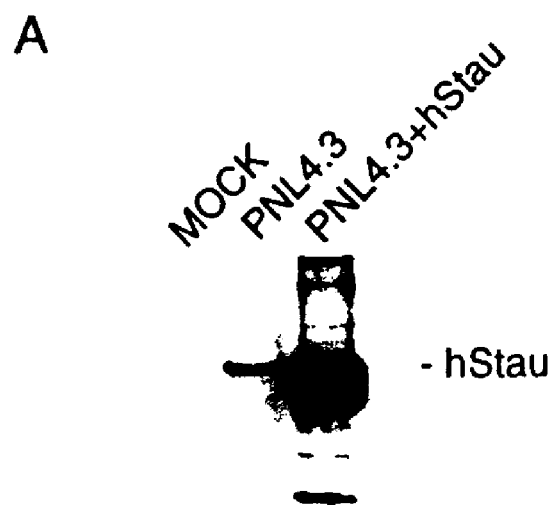
FIG. 11 shows overexpression of hStau causing a decrease of infectivity of HIV-1 particles. 10 µg pNL4.3 was transfected into 293T cells with or without an expression plasmid encoding HA-hStau at a 1:1.3 molar basis (or KS DNA carrier). A, Virus was prepared from mock, pNL4.3 and pNL4.3+hStau transfected cells and used in Western blot analysis using equal quantities of p24 in each lane. For infectivity assays, equal quantities of p24 were used to infect MAGI and BF-24 indicator cells and infectivity was quantitated at 48 h p.i. by colorimetric and CAT activity assays, respectively. B, BF-24 cells were washed extensively and lysed by freeze-thaw in 0.25 M Tris, pH 7.5, followed by heat inactivation. CAT activity in cells was determined by standard assay by thin layer chromatography (a representative result is shown here). C, The data shown are the means and standard errors of the means (S.E.M.) from three independent infectivity assays in BF-24 cells. Relative CAT activity (compared to the pNL4.3 lane which is set to 1) was calculated by phosphoimager analysis using the Molecular Dynamics ImageQuant software. MAGI assay results conferred with those from BF-24 assays revealing a 4-fold (±0.3, S.E.M.) reduction in the number of blue β-galactosidase-positve cells 48 h p.i. (7).
Figure 11:
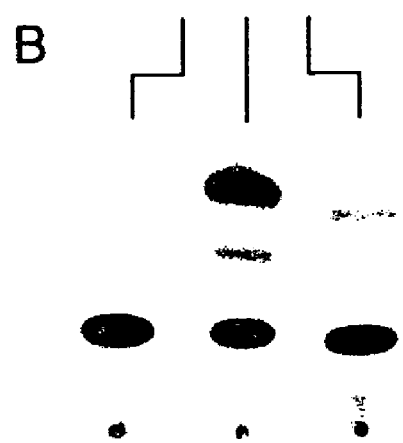
Figure 11:
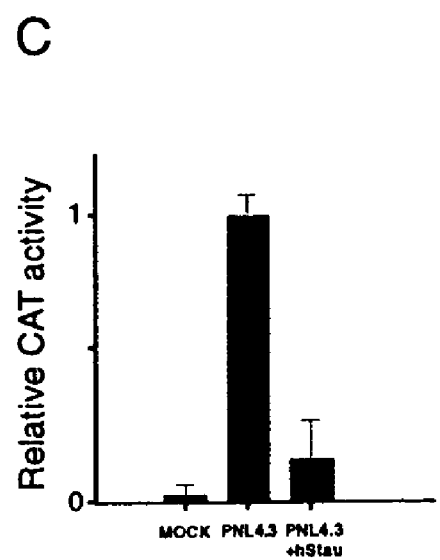

Whatever the particular mechanism of incorporation of hStau into HIV-1, the present invention clearly identifies a new HIV-targeting molecule. The effects of incorporated hStau on the infectivity of HIV-1 particles were investigated. hStau with pNL4.3 was overexpressed in 293T cells and a corresponding increase in hStau was found in purified virus preparations (FIG. 11A). Equal amounts of virus from pNL4.3- and pNL4.3/hStau-transfected cells were used to infect HeLa-CD4-βGal (MAGI; 19) and BF-24 (20) indicator cells. Both infectivity assays indicated that an excess amount of hStau in HIV-1 particles has a marked negative effect on virus infectivity [4- and a 6.7-fold decrease in MAGI and BF-24 assays, respectively; FIGS. 4B & C]. These data further support the contention that hStau plays an integral role in virus assembly and can contribute to the infectious potential.

EXAMPLE 21

Discussion and Implications of the Role of Staufen in RNA Encapsidation

Because all cells examined until now express hStau, its virion incorporation is indicative of a late role in viral assembly. hStau's ability to bind double-stranded and structured RNAs may result in virion incorporation which would be consistent with a role in the sorting of retroviral genomic RNAs to sites of virus assembly. While the other TAR RNAand dsRNA-binding proteins have important roles in HIV-1 gene expression and replication, hStau is shown here as the only member that is incorporated into virus particles. Moreover, hStau appears to be incorporated into several retroviruses as well as RNA viruses—and not DNA viruses—suggesting a common role for hStau in the assembly process of RNA viruses.

Overexpression of hStau leads to a marked increase in the amount of hStau in virus preparations (FIG. 11A). As a consequence, virus infectivity is negatively affected (FIGS. 11B & C). These results may be explained by steric hindrance or an inappropriate amount of encapsidated viral RNA. Nevertheless, the data herein presented demonstrate that an appropriate amount of incorporated hStau is required to generate infectious viral particles. Accordingly, our infection backcross experiments using MT4 and Jurkat cells show that the quantity of incorporated hStau is independent of the cell line, contrary to what was found for cellular proteins within the HIV-1 envelope. Briefly, backcross experiments were performed using MT4 and Jurkat T cells. 50 ng p24 pNL4.3 virus equivalents were used to infect Jurkat and MT4 cells. Cells were washed extensively and allowed to become productively infected. Virus was then harvested from each culture, purified, and the same amount was used to infect the other cell type. Virus was again harvested and hStau was evaluated in the all virus preparations by Western analysis using equal quantities of virus from each preparation. hStau levels per ng p24 were relatively constant in all virus preparations, in contrast to what was found for proteins embedded in the HIV-1 envelope [(cf. L. Bastiani, S. Laal, M. Kim, S. Zolia-Pazner, *J. Virol.* 71, 3444 (1997)]. Based on the role of staufen for HIV infectivity, it will be interesting to see the effect of the expression of a staufen antisense on HIV-1 replication and/or morphogenesis. It is tempting to speculate that such an antisense expression (or the expression of an antibody directed against staufen) will reduce the infectivity of HIV. Based on the apparent role of staufen in RNA viruses in general, such an approach might also be beneficial for other RNA viruses.

TAR RNA-binding in HIV-1 has a critical role in transcription (22), but has also been shown to regulate viral gene expression post-transcriptionally (23). All members of the dsRNA-binding protein family are associated with the translational machinery including xlrbpa which can bind to free ribosomal subunits and mRNAs in *Xenopus* oocytes (24), and PKR that was recently shown to be associated with 40S ribosomal subunits (25). Furthermore, TRBP can modulate PKR phosphorylation of eIF-2α to modulate HIV-1 gene expression (26). TRBP was also recently shown to interact with Tax of HTLV-1 (27) and this could modulate gene expression at transcriptional and/or post-transcriptional levels. Likewise, additional regulatory roles for hStau are expected to be uncovered. In support of this are preliminary studies that indicate that hStau can markedly relieve the TAR-mediated translational repression in vitro in reticulocyte lysates. Highly purified hStau (5) was incubated with a TAR-less RNA or a TAR-containing RNA generated by in vitro transcription of SP6CAT and SP6TARCAT plasmids [Parkin N. T. et al., *EMBO J.* 7, 2831 (1988)]. TAR dramatically reduced the amount of CAT protein produced in vitro translation as reported previously (ibid.). A dose-dependent derepression of CAT synthesis was observed when the TAR-CAT RNA was preincubated with recombinant hStau. There were no marked effects on CAT protein levels from the TAR-less RNA. This indicates that hStau has several functional parallels to its metazoan counterpart, and furthermore, its role in HIV-1 replication is likely to be multifaceted.

Herein, no attempt has been made to define the mechanism by which hStau is incorporated into HIV-1 particles but it is likely to require TAR-like and structured RNA domains characteristic of retrovirus leader sequences (29); although higher order structures may also be critical (18, 30). Virus incorporation of hStau may indeed be mediated by both viral and cellular proteins. It has recently been determined however that the HIV-1 vpr, env, vpu, pol (protease, RT, integrase), and nef genes are dispensable for Stau incorporation (data not shown). To evaluate the role of HIV-1 genes in hStau incorporation, proviral constructs containing a mutated ATG initiation codon (vpu), frameshift sequence (vpr), premature stop codon (nef), and sequence deletions (EcoRI/EcoRI for pol; and a BglII/BglII for env) in HxBru were tested. In addition, VSV G pseudotyped HIV-1 particles incorporated hStau, thus indicating again that env is not necessary for hStau incorporation. However, both NC and the psi RNA domain are not only critical for genomic RNA encapsidation, but they also appear to mediate hStau incorporation. In light of the negative impact of hStau overexpression on viral infectivity, hStau may be a suitable target for an anti-HIV-1 strategy. Furthermore, in light of the demonstration that hStau is incorporated into other retroviruses as well as Reovirus, staufen may be a suitable target for anti RNA-virus therapy in general.

REFERENCES

Ainger, K., Avossa, D., Morgan, F., Hill, S. J., Barry, C., Barbarese, E., and Carson, J. H. (1993). Transport and localization of exogenous myelin basic protein mRNA microinjected into oligodendrocytes. J. Cell. Biol. 123, 431–441.

Aloyz, R. S., and DesGroseillers, L. (1995). Processing of the L5-67 precursor peptide and characterization of LUQIN in the central nervous system of Aplysia californica. Peptides 16, 331–338.

Bassell, G., and Singer, R. H. (1997). mRNA and cytoskeletal filaments. Curr. Opin. Cell Biol. 9, 109–115.

Benkirane, M., Neuveut, C., Chun, R. F., Smith, S. M., Samuel, C. E., Gatignol, A., and Jeang, K.-T. (1997). Oncogenic potential of TAR RNA binding protein TRBP and its regulatory interaction with RNA-dependent protein kinase PKR. EMBO J. 16, 611–624.

Breitwieser, W., Markussen, F.-H., Horstmann, H., and Ephrussi, A. (1996). Oskar protein interaction with Vasa represents an essential step in polar granule assembly. Genes & Dev. 10, 2179–2188.

Broadus, J., Fuerstenberg, S., and Doe, C. Q. (1998). Staufen-dependent localization of prospero mRNA contributes to neuroblast daughter-cell fate. Nature 391, 792–795.

Cosentino, G. P., Venkatesan, S., Serluca, F. C., Green, S., Mathews, M. B., and Sonenberg, N. (1995). Double-stranded-RNA-dependent protein kinase and TAR RNA-binding protein form homo- and heterodimers in vivo. PNAS 92, 9445–9449.

Crino, P. B., and Eberwine, J. (1996). Molecular characterization of the dendritic growth cone: regulated mRNA transport and local protein synthesis. Neuron 17, 1173–1187.

Davis, L., Banker, G. A., and Steward, O. (1987). Selective dendritic transport of RNA in hippocampal neurons in culture. Nature 330, 477–479.

DesGroseillers, L., and Lemieux, N. (1996). Localization of a human double-stranded RNA-binding protein gene (STAU) to band 20q13.1 by fluorescence in situ hybridization. Genomics 36, 527–529.

Deshler, J. O., Highett, M. I., and Schnapp, B. J. 1997. Localization of *Xenopus* Vg1 mRNA by Vera protein and the endoplasmic reticulum. Science 276, 1128–1131.

Eckmann, C. R., and Jantsch, M. F. (1997). Xlrbpa, a double-stranded RNA-binding protein associated with ribosomes and heterogeneous nuclear RNPs. J. Cell Biol. 138, 239–253.

Elisha, Z., Havin, L., Ringel, I., and Yisraeli, J. K. (1995). Vg1 RNA binding protein mediates the association of Vg1 RNA with microtubules in *Xenopus* oocytes. EMBO J. 14, 5109–5114.

Ephrussi, A., Dickinson, L. K., and Lehamnn, R. (1991). Oskar organizes the germ plasm and directs localization of the posterior determinant nanos. Cell 66, 37–50.

Erdelyi, M., Michon, A. M., Guichet, A., Glotzer, J. B., and Ephrussi, A. (1995). Requirement for *Drosophila* cytoplasmic tropomyosin in oskar mRNA localization. Nature 377, 524–527.

Ferrandon, D., Elphick, L., N"sslein-Volhard, C., and St Johnston, D. (1994). Staufen protein associates with the 3'UTR of bicoid mRNA to form particles that move in a microtubule-dependent manner. Cell 79, 1221–1232.

Ferrandon, D., Koch, I., Westhof, E., and N"sslein-Volhard, C. (1997). RNA—RNA interaction is required for the formation of specific bicoid mRNA 3' UTR-staufen ribonucleoprotein particles. EMBO J. 16, 1751–1758.

Forristall, C., Pondel, M., and King, M. L. (1995). Patterns of localization and cytoskeletal association of two vegetally localized RNAs, Vg1 and Xcat-2. Development 121, 201–208.

Gatignol, A., Buckler, C., and Jeang, K.-T. (1993). Relatedness of an RNA-binding motif in human immunodeficiency virus type 1 TAR RNA-binding protein TRBP to human P1/dsI kinase and *Drosophila* staufen. Mol. Cell. Biol. 13, 2193–2202.

Gazzaley, A. H., Benson, D. L., Huntley, G. W., and Morrison, J. H. (1997). Differential subcellular regulation of NMDAR1 protein and mRNA in dendrites of dendate gyrus granule cells after perforant path transection. J. Neurosci. 17, 2006–2017.

Hochstenback, F., David, V., Watkins, S., and Brenner, M. B. (1992). Endoplasmic reticulum resident protein of 90 kilodaltons associates with the T- and B-cell antigen receptors and major histocompatibility complex antigens during assembly. PNAS 89, 4734–4738.

Jockers, R., Da Silva, A., Strosberg, A. D., Bouvier, M., and Marullo, S. (1996). New molecular and structural determinants involved in b2-adrenergic receptor desensitization and sequestration. J. Biol. Chem. 271, 9355–9362.

Kang, H., and Schuman, E. M. 1996. A requirement for local protein synthesis in neurotrophin-induced hippocampal synaptic plasticity. Science 273, 1402–1406.

Kim-Ha, J., Smith, J. L., and Macdonald, P. M. (1991). Oskar mRNA is localized to the posterior pole of the *Drosophila* oocyte. Cell 66, 23–35.

Kim-Ha, J., Kerr, K., and Macdonald, P. M. (1995). Translational regulation of oskar mRNA by Bruno, an ovarian RNA-binding protein, is essential. Cell 81, 403–412.

Kislauskis, E. H., Zhu, X., and Singer, R. H. (1997). b-actin messenger RNA localization and protien synthesis augment cell motility. J. Cell Biol. 136, 1263–1270.

Kloc, M., and Etkin, L. D. (1994). Delocalization of Vg1 mRNA from the vegetal cortex in *Xenopus* oocytes after destruction of Xlsirt RNA. Science 265, 1101–1103.

Knowles, R. B., Sabry, J. H., Martone, M. E., Deerinck, T. J., Ellisman, M. H., Bassell, G. J., and Kosik, K. S. 1996. Translocation of RNA granules in living neurons. J. Neurosci. 16, 7812–7820.

Kraut, R., and Campos-Ortega, J. A. (1996). Inscutable, a neural precursor gene of *Drosophila* encodes a candidate for a cytoskeletal adaptor protein. Dev. Biol. 174, 66–81.

Krovat, B. C., and Jantsch, M. F. (1996). Comparative mutational analysis of the double-stranded RNA binding domains of *Xenopus laevis* RNA-binding protein A. J. Biol. Chem. 271, 28112–28119.

Li, P., Yang, X., Wasser, M., Cai, Y., and Chia, W. 1997. Inscutable and staufen mediate asymmetric localization and segregation of prospero RNA during *Drosophila* neuroblast cell divisions. Cell 90, 437–447.

Long, R. M., Singer, R. H., Meng, X., Gonzalez, I., Nasmyth, K., and Jansen, R.-P. (1997). Mating type switching in yeast controlled by asymetric localization of ASH1 mRNA. Science 177, 383–387.

Martin, K. C., Casadio, A., Zhu, H., Yaping, E., Rose, J. C., Chen, M., Bailey, C. H., and Kandel, E. R. (1997). Synapse-specific, long-terme facilitation of Aplysia sensory to motor synapses: a function for local protein synthesis in memory storage. Cell 91, 927–938.

McCormack, S. J., Ortega, L. G., Doohan, J. P., and Samuel, C. E. (1994). Mechanism of interferon action: motif 1 of the interferon-induced, RNA-dependent protein kinase (PKR) is sufficient to mediate RNA-binding activity. Virology 198, 92–99.

Nakielny, S., Fischer, U., Michael, W. M., and Dreyfuss, G. (1997). RNA transport. Ann. Rev. Neurosci. 20, 269–301.

Okita, T. W., Li, X., and Roberts, M. W. (1994). Targeting of mRNAs to domains of the endoplasmic reticulum. TIBS 4, 91–96.

Pachter, J. S. (1992). Association of mRNA with the cytoskeletal framework: its role in the regulation of gene expression. Crit. Rev. Euk. Gene Exp. 2, 1–18.

Pokrywka, N. J., and Stephenson, E. C. (1995). Microtubules are a general component of mRNA localization systems in *Drosophila* oocytes. Dev. Biol. 167, 363–370.

Rings, E. H. H. M., B"lier, H. A., Neele, A. M., and Dekker, J. (1994). Protein sorting versus messenger RNA sorting?. Eur. J. Cell Biol. 63, 161–171.

Ross, A. F., Oleynikov, Y., Kisllauskis, E. H., Taneja, K. L., and Singer, R. H. 1997. Characterization of a b-actin mRNA zipcode-binding protein. Mol. Cell. Biol. 17, 2158–2165.

Schmedt, C., Green, S. R., Manche, L., Taylor, D. R., Ma, Y., and Mathews, M. B. (1995). Functional characterization of the RNA-binding domain and motif of the double-stranded RNA-dependent protein kinase DAI (PKR). J. Mol. Biol. 249, 29–44.

Schumacher, J. M., Lee, K., Edelhoff, S., and Braun, R. E. (1995). Spnr, a murine RNA-binding protein that is localized to cytoplasmic microtubules. J. Cell Biol. 129, 1023–1032.

Schwartz, S. P., Aisenthal, L., Elisha, Z., Oberman, F., and Yisraeli, J. K. (1992). A 69-kDa RNA-binding protein from *Xenopus* oocytes recognizes a common motif in two vegetally localized maternal mRNAs. PNAS 89, 11895–11899.

Steward, O. (1997). mRNA localization in neurons: a multipurpose mechanism? Neuron 18, 9–12.

St Johnston, D., Driever, W., Berleth, T., Richstein, S., and Nüsslein-Volhard, C. (1989). Multiple steps in th elocalization of bicoid RNA to the anterior pole of the Drosophila oocyte. Dev. (Suppl.) 107, 13–19.

St Johnston, D., Beuchle, D., and Nüsslein-Volhard, C. (1991). Staufen, a gene required to localize maternal RNAs in the Drosophila egg. Cell 66, 51–63.

St Johnston, D., Brown, N. H., Gall, J. G., and Jantsch, M. (1992). A conserved double-stranded RNA-binding domain. PNAS 89, 10979–10983.

St Johnston, D. (1995). The intracellular localization of messenger RNAs. Cell 81, 161–170.

Takizawa, P. A., Sil, A., Swedlow, J. R., Herskowitz, I., and Vale, R. D. (1997). Actin-dependent localization of an RNA encoding a cell-fate determinant in yeast. Nature 389, 90–93.

Terasaki, M., Chen, L. B., and Fujiwara, K. (1986). Microtubules and the endoplasmic reticulum are highly interdependent structures. J. Cell Biol. 103, 1557–1568.

Tetzlaff, M. T., Jäckle, H., and Pankratz, M. J. (1996). Lack of Drosophila cytoskeletal tropomyosin affects head morphogenesis and the accumulation of oskar mRNA required for germ cell formation. EMBO J. 15, 1247–1254.

Tiedge, H., Fremeau, R. T. Jr., Weinstock, P. H., Arancio, O., and Brosius, J. (1991). Dendritic localization of neural BC1 RNA. PNAS 88, 2093–2097.

Tiedge, H., Zhou, A., Thorn, N. A., and Brosius, J. (1993). Transport of BC1 RNA in hypothalamo-neurohypophyseal axons. J. Neurosci. 13, 4214–4219.

Tongiorgi, E., Righi, M., and Cattaneo, A. (1997). Activity-dependent dendritic targeting of BDNF and TrkB mRNAs in hippocampal neurons. J. Neurosci. 17, 9492–9505.

Wickham, L., and DesGroseillers, L. (1991). A bradykinin-like neuropeptide precursor gene is expressed in neuron L5 of Aplysia californica. DNA and Cell biology 10: 249–258.

Wilhelm, J. E., and Vale, R. D. (1993). RNA on the move: The mRNA localization pathway. J. Cell Biol. 123, 269–274.

Wilsch-Bräuninger, M., Schwarz, H., and Nüsslein-Volhard, C. (1997). A sponge-like structure involved in the association and transport of maternal products during Drosophila oogenesis. J. Cell Biol. 139, 817–829.

Zauner, W., Kratz, J., Staunton, J., Feick, P., and Wiche, G. (1992). Identification of two distinct microtubule binding domains on recombinant rat MAP1B. Eur. J. Cell Biol. 57, 66–74.

1. D. St. Johnston, D. Beuchle, C. Nüsslein-Volhard, Cell 66, 51 (1991).
2. D. Ferrandon, L. Elphick, C. Nüsslein-Volhard, D. St. Johnston, Cell 79, 1221 (1994).
3. J. Kim-Ha, K. Kerr, P. M. Macdonald, Cell 81:403 (1995).
4. P. Li, X. Yang, M. Wasser, Y. Cai, W. Chia, Cell 90, 437 (1997); J. Broadus and S. Fuerstenberg, C. Q. Doe, Nature 391, 792 (1998).
5. L. Wickham, T. Duchaine, M. Luo, I. R. Nabi, L. DesGroseillers, submitted; L. DesGroseillers and N. Lemieux, Genomics 36, 527 (1996).
8. J. F. Fortin, R. Cantin, M. J. Tremblay, J. Virol. 72, 2105 (1998).
9. D. E. Ott, L. V. Coren, D. G. Johnson, R. C. Sowder 2nd, L. O. Arthur, L. E. Henderson, AIDS Res. Hum. Retroviruses 11, 1003 (1995).
10. D. E. Ott, et al., J. Virol. 70, 7734 (1996).
11. D. Bergeron, L. Poliquin, C. A. Kozak, É. Rassart, J. Virol. 65, 7 (1991).
13. M. S. McBride, M. D. Schwartz, A. T. Panganiban, J. Virol. 71, 4544, (1997); A. M. L. Lever, H. G. Göttlinger, W. A. Haseltine, J. G. Sodroski, J. Virol. 63, 4085 (1989); R. D. Berkowitz, M.-L. Hammarskjold, C. Helga-Maria, D. Rekosh, S. P. Goff, Virology 212, 718 (1995); M. S. McBride, M. D. Schwartz, A. T. Panganiban, J. Virol. 71, 4544 (1997); D. T. K. Poon, G. Li, A. Aldovini, J. Virol. 72, 1983 (1998).
14. T. Dorfman, J. Luban, S. P. Goff, W. A. Haseltine, H. G. Göttlinger, J. Virol. 67, 6159 (1993).
15. Y. Huang et al., J. Virol. 71, 4378 (1997).
16. G. Miele, A. J. Mouland, G. P. Harrison, E. Cohen, A. M. L. Lever, J. Virol. 70, 944 (1996).
17. A. Mizuno et al., AIDS Res. Hum. Retrov. 12, 793 (1996); R. Gorelick, S. Nigida, J. Bess, L. Arthur, L. Henderson, A. Rein, J. Virol. 64, 3207 (1990); R. Gorelick, D. Chabot, L. Henderson, L. Arthur, ibid., 67, 4027 (1993); J. Dannull, A. Surovoy, G. Jung, K. Moelling, EMBO J. 13, 1525 (1994).
18. R. N. De Guzman et al., Science 279, 384 (1998).
19. J. Kimpton and M. Emerman, J. Virol. 66, 2232 (1992).
20. J. F. Fortin, R. Cantin, G. Lamontagne, M. Tremblay, J. Virol. 71, 3588 (1997).
22. A. Gatignol, A. Buckler-White, B. Berkhout, K. T. Jeang, Science 29, 1597 (1991); S. K. Arya, C. Gua, S. F. Josephs, F. Wong-Staal, Science 229, 69 (1985); A. Dayton, J. Sodroski, C. Rosen, W. Goh, W. Haseltine, Cell 44, 941 (1986).
23. D. Ferrandon, I. Koch, E. Westof, C. Nusslein-Volhard, EMBO. J 16, 1751 (1997); H. Park et al., Proc. Natl. Acad. Sci. U.S.A. 91, 4713 (1994).
24. C. R. Eckman and M. F. Jantsch, J. Cell. Biol. 138, 239 (1997).
25. S. Zhu, P. R. Romano, R. C. Wek, J. Biol. Chem. 272, 14434 (1997).
26. M. Benkirane et al., EMBO J. 16, 611 (1997).
27. M. Donzeau, E. L. Winnacker, M. Meisterernst, J. Virol. 71, 2628 (1997).
29. G. P. Harrison, E. Hunter, A. M. Lever, J. Virol. 69, 2175 (1995); C. Berlioz, J.-L. Darlix, ibid. 69, 2214 (1995).
30. D. A Circle, O. D. Neel, H. D. Robertson, P. A. Clarke, M. B. Mathews, RNA 3, 438 (1997); M. Laughrea et al., J. Virol. 71, 3397 (1997).
32. T. J. Palker et al., J. Immunol. 142, 3612 (1989); T. J. Palker et al., Proc. Natl. Acad. Sci. U.S.A. 85, 1932 (1988); T. J. Palker et al., Proc. Natl. Acad. Sci. U.S.A. 84, 2479 (1987).
33. J. Cogniaux et al., J. Immunol. Meth. 128, 165 (1990).
34. P. J. Barr et al., U.C.L.A. Symp. Mol. Cell. Biol. New Ser. 43, 205 (1987); K. S. Steimer et al., Virology 150, 283 (1986).
35. A. J. Mouland and G. N. Hendy, Mol. Endocrinol. 6, 1781 (1992).

Although the present invention has been described hereinabove by way of preferred embodiments thereof, it can be modified, without departing from the spirit and nature of the subject invention as defined in the appended claims.

What is claimed is:

1. An isolated nucleic acid molecule, comprising a polynucleotide sequence which encodes a Staufen polypeptide sequence, said polynucleotide sequence being selected from the group consisting of:
   (a) SEQ ID NO:6;
   (b) SEQ ID NO:3;
   (c) SEQ ID NO:1;
   (d) SEQ ID NO:6;
   (e) SEQ ID NO:7; and
   (f) a nucleotide sequence fully complementary to any of the nucleotide sequence encoding a Staufen polypeptide in (a), (b), (c), (d), or (e).

2. The isolated nucleic acid molecule of claim 1, wherein said polynucleotide sequence is selected from the group consisting of:
   (a) a polynucleotide sequence encoding a Staufen polypeptide comprising amino acids from 1 to 577 of SEQ ID NO:2;
   (b) a polynucleotide sequence encoding a Staufen polypeptide comprising the sequence of amino acids of SEQ ID NO:4;
   (c) a polynucleotide sequence encoding a Staufen polypeptide comprising amino acids from 2 to 577 of SEQ ID NO:2;
   (d) a polynucleotide sequence encoding a Staufen polypeptide comprising amino acids from 2 to 496 of SEQ ID NO:4;
   (e) a polynucleotide sequence encoding a Staufen polypeptide comprising the sequence of amino acids of SEQ ID NO:8;
   (f) a polynucleotide sequence encoding a Staufen polypeptide comprising amino acids from 2 to 487 of SEQ ID NO:4;
   (g) a polynucleotide sequence fully complementary to any of the polynucleotide sequence encoding a Staufen polypeptide in (a), (b), (c), (d), (e), or (f).

3. A recombinant vector comprising said isolated nucleic acid molecule of claim 2.

4. A method of making a recombinant host cell comprising introducing the recombinant vector of claim 3 into a host cell.

5. A recombinant host cell produced by the method of claim 4.

6. A recombinant method for producing a Staufen polypeptide, comprising culturing said host cell of claim 5 under conditions such that said polypeptide is expressed and recovering said Staufen polypeptide.

7. A recombinant vector comprising said isolated nucleic acid molecule of claim 1.

8. A method of making a recombinant host cell comprising introducing the recombinant vector of claim 7 into a host cell.

9. A recombinant host cell produced by the method of claim 8.

10. A recombinant method for producing a Staufen polypeptide, comprising culturing said host cell of claim 9 under conditions such that said polypeptide is expressed and recovering said Staufen polypeptide.

* * * * *